United States Patent
Park et al.

(10) Patent No.: US 10,752,697 B2
(45) Date of Patent: Aug. 25, 2020

(54) ANTI-GLYPICAN 3 ANTIBODY AND PHARMACEUTICAL COMPOSITION CONTAINING THE SAME

(71) Applicant: MOGAM INSTITUTE FOR BIOMEDICAL RESEARCH, Yongin-si, Gyeonggi-do (KR)

(72) Inventors: Jae Chan Park, Yongin-si (KR); Kisu Kim, Yongin-si (KR); Mijung Lee, Yongin-si (KR); Eun-Hee Lee, Yongin-si (KR); Dong-Sik Kim, Yongin-si (KR); Eun Jung Song, Yongin-si (KR); Sujeong Kim, Yongin-si (KR); Hyung-Kwon Lim, Yongin-si (KR); Kyuhyun Lee, Yongin-si (KR); Jongwha Won, Yongin-si (KR); Soongyu Choi, Yongin-si (KR); Young Seoub Park, Yongin-si (KR)

(73) Assignee: MOGAM INSTITUTE FOR BIOMEDICAL RESEARCH, Gyeonggi-Do (KR)

( * ) Notice: Subject to any disclaimer, the term of this patent is extended or adjusted under 35 U.S.C. 154(b) by 240 days.

(21) Appl. No.: 15/771,527

(22) PCT Filed: Oct. 27, 2016

(86) PCT No.: PCT/KR2016/012193
§ 371 (c)(1),
(2) Date: Apr. 27, 2018

(87) PCT Pub. No.: WO2017/074074
PCT Pub. Date: May 4, 2017

(65) Prior Publication Data
US 2018/0346592 A1 Dec. 6, 2018

(30) Foreign Application Priority Data
Oct. 29, 2015 (KR) .................. 10-2015-0150642

(51) Int. Cl.
*C07K 16/30* (2006.01)
*A61K 47/68* (2017.01)

(52) U.S. Cl.
CPC ........ *C07K 16/303* (2013.01); *A61K 47/6859* (2017.08); *C07K 2317/31* (2013.01); *C07K 2317/622* (2013.01)

(58) Field of Classification Search
CPC ...................... C07K 16/00–468; C07K 16/303
See application file for complete search history.

(56) References Cited

U.S. PATENT DOCUMENTS 7,919,086 B2  4/2011  Nakano et al.
8,680,247 B2  3/2014  Terrett et al.
2004/0236080 A1  11/2004  Aburatani et al.
2008/0124330 A1  5/2008  Nakano et al.
2015/0147330 A1  5/2015  Ho et al.
2017/0010270 A1*  1/2017  Ohtomo ............... C07K 16/303

FOREIGN PATENT DOCUMENTS

KR       100877176 B1    1/2009
KR    1020130014698 A    2/2013

OTHER PUBLICATIONS

Almagro & Fransson, Frontiers in Bioscience 2008; 13:1619-33 (Year: 2008).*
De Genst et al., Developmental and Comparative Immunology, 2006, 30:187-98 (Year: 2006).*
Ward et al., Nature, 1989, 341:544-546 (Year: 1989).*
Barthelemy et al. (Journal of Biological Chemistry, 2008, 283:3639-3654) (Year: 2008).*
Choi et al., 2011, Molecular BioSystems, 2011, 7:3327-334 (Year: 2011).*
Griffiths et al. (The EMBO Journal, 1993, 12:725-734) (Year: 1993).*
Klimka et al., British Journal of Cancer, 2000, 83:252-260 (Year: 2000).*
Beiboer et al., Journal of Molecular Biology, 2000, 296:833-849 (Year: 2000).*
Baruch D. Jakubovic et al., "Glypican-3: From the mutations of Simpson-Golabi-Behmel genetic syndrome to a tumor marker for hepatocellular carcinoma," Experimental and Molecular Pathology, 2007, pp. 184-189, vol. 82, Elsevier Inc.
Giuseppe Pilia et al., "Mutations in GPC3, a glypican gene, cause the Simpson-Golabi-Behmel overgrowth syndrome," Nature Genetics, Mar. 1996, pp. 241-247, vol. 12, Nature Publishing Group.
Hermann Lage et al., "Cloning and characterization of human cDNAs encoding a protein with high homology to rat intestinal development protein OCI-5," GENE, 1997, pp. 151-156, vol. 188, Elsevier Science B.V.
Hirofumi Hanaoka et al., "Glypican-3 Targeted Human Heavy Chain Antibody as a Drug Carrier for Hepatocellular Carcinoma Therapy," Molecular Pharmaceutics, May 8, 2015, pp. 2151-2157, vol. 12.

(Continued)

*Primary Examiner* — Jessica H Roark
(74) *Attorney, Agent, or Firm* — Cantor Colburn LLP

(57) ABSTRACT

The present invention relates to an antibody specifically binding to glypican 3 (GPC3), a nucleic acid encoding the antibody, a vector and a host cell containing the nucleic acid, a method of preparing the antibody, and a pharmaceutical composition for treating cancer or tumor, containing the antibody as an active ingredient. The antibody specifically binding to glypican 3 according to the present invention may be effectively used to treat cancer or tumor, particularly, hepatocellular carcinoma due to high affinity and specificity to glypican 3.

17 Claims, 9 Drawing Sheets
(9 of 9 Drawing Sheet(s) Filed in Color)
Specification includes a Sequence Listing.

(56) References Cited

OTHER PUBLICATIONS

J. Filmus et al., "Isolation of a cDNA Corresponding to a Developmentally Regulated Transcript in Rat Intestine," Molecular and Cellular Biology, Oct. 1988, pp. 4243-4249, vol. 8, No. 10, American Society for Microbiology.
Tetsuya Nakatsura et al., "Usefulness of the Novel Oncofetal Antigen Glypican-3 for Diagnosis of Hepatocellular Carcinoma and Melanoma," Biodrugs, 2005, pp. 71-77, vol. 19(2).
International Search Report for PCT/KR2016/012193, dated Jan. 31, 2017 (6 pages).

* cited by examiner

ANTI-GLYPICAN 3 ANTIBODY AND PHARMACEUTICAL COMPOSITION CONTAINING THE SAME

CROSS REFERENCE TO RELATED APPLICATIONS

This application is a National Stage application of International Application No. PCT/KR2016/012193, filed Oct. 27, 2016, which claims the benefit of Korean Patent Application No. 10-2015-0150642 filed on Oct. 29, 2015, each of which is incorporated by reference in its entirety herein.

TECHNICAL FIELD

The present invention relates to an antibody specifically binding to glypican 3 (GPC3), a nucleic acid encoding the antibody, a vector and a host cell containing the nucleic acid, a method of preparing the antibody, and a pharmaceutical composition for treating cancer or tumor, containing the antibody as an active ingredient.

BACKGROUND ART

Glypican 3 was separated in the small intestine of a rat as a transcript in a developmental stage (Mol. Cell Biol. 8, 4243-4249, 1988), and thereafter, it was reported that a gene encoding glypican 3 was isolated from a glycosyl-phosphatidylinositol (GPI)-linked type sulfate human gastric cancer cell line having a core protein of a glypican family (molecular weight of 69 kDa) (Gene, 188, 151-156, 1997). It was reported that glypican 3 forms a protein-protein complex together with an insulin-like growth factor-2 and regulates actions of the insulin-like growth factor-2 (Nat. Genet., 12, 241-247, 1996). Particularly, it was known that glypican 3 is expressed in the fetal liver and placenta during development and in normal adult tissue, expression of glypican 3 is deteriorated or glypican 3 is not expressed at all.

Glypican 3 is known as a kind of oncofetal antigen that belongs to a glypican family of glycosyl-phosphatidylinositol (GPI)-anchored heparin sulfate proteoglycans, and cell membrane-bound glypican 3 is known to be composed of two subunits linked by one or more disulfide bonds.

In relation to functions and uses of glypican 3, it was reported that glypican may serve as a hepatocellular carcinoma marker, and it was suggested that glypican may serve as a receptor of endostatin having a possibility of an angiogenesis inhibitor, which was not clearly identified.

Recently, it has been known that glypican 3 is expressed in various cancers, particularly, hepatocellular carcinoma (HCC), melanoma, Wilm's tumor, and hepatoblastoma (Jakubovic and Jothy; Ex. Mol. Path. 82:184-189 (2007); Nakatsura and Nishimura, Biodrugs 19(2):71-77 (2005)), and it was reported that it is actually possible to treat tumors such as hepatic cancer, and the like, using an antibody against glypican 3 (Korean Patent No. 877,176, and the like).

Currently, several anti-glypican 3 antibodies were reported, but an antibody having a satisfactory therapeutic effect, particularly, an excellent cancer therapeutic effect has been not yet reported. Therefore, a need for an anti-glypican 3 antibody having a more excellent therapeutic effect is significant.

Therefore, the present inventors invented a novel antibody specifically binding to glypican 3 with high affinity, and confirmed a possibility of the antibody according to the present invention as an efficient anti-cancer agent, thereby completing the present invention.

DISCLOSURE

An object of the present invention is to provide a novel antibody specifically binding to glypican 3 (GPC3) with high affinity, a nucleic acid encoding the antibody, a vector and a host cell containing the nucleic acid, a method of preparing the antibody, and a pharmaceutical composition for treating cancer or tumor, containing the antibody as an active ingredient.

According to an aspect of the present invention, there is provided a novel antibody specifically binding to glypican 3 (GPC3) with high affinity.

According to another aspect of the present invention, there are provided a nucleic acid encoding an anti-glypican 3 antibody according to the present invention; a vector containing the nucleic acid; and a cell transduced with the vector, and a method of preparing an antibody according to the present invention, using the same.

According to another aspect of the present invention, there are provided a pharmaceutical composition for treating cancer or tumor, containing an anti-glypican 3 antibody according to the present invention as an active ingredient, and a method of treating cancer or tumor using the anti-glypican 3 antibody according to the present invention.

BRIEF DESCRIPTION OF DRAWINGS

The patent or application file contains at least one drawing executed in color. Copies of this patent or patent application publication with color drawing(s) will be provided by the Office upon request and payment of the necessary fee.

(a) SKHep1 (GPC3 negative cell line)
(b) SKHep1-GPC3 #9 (GPC3 positive cell line)

Figure 10:
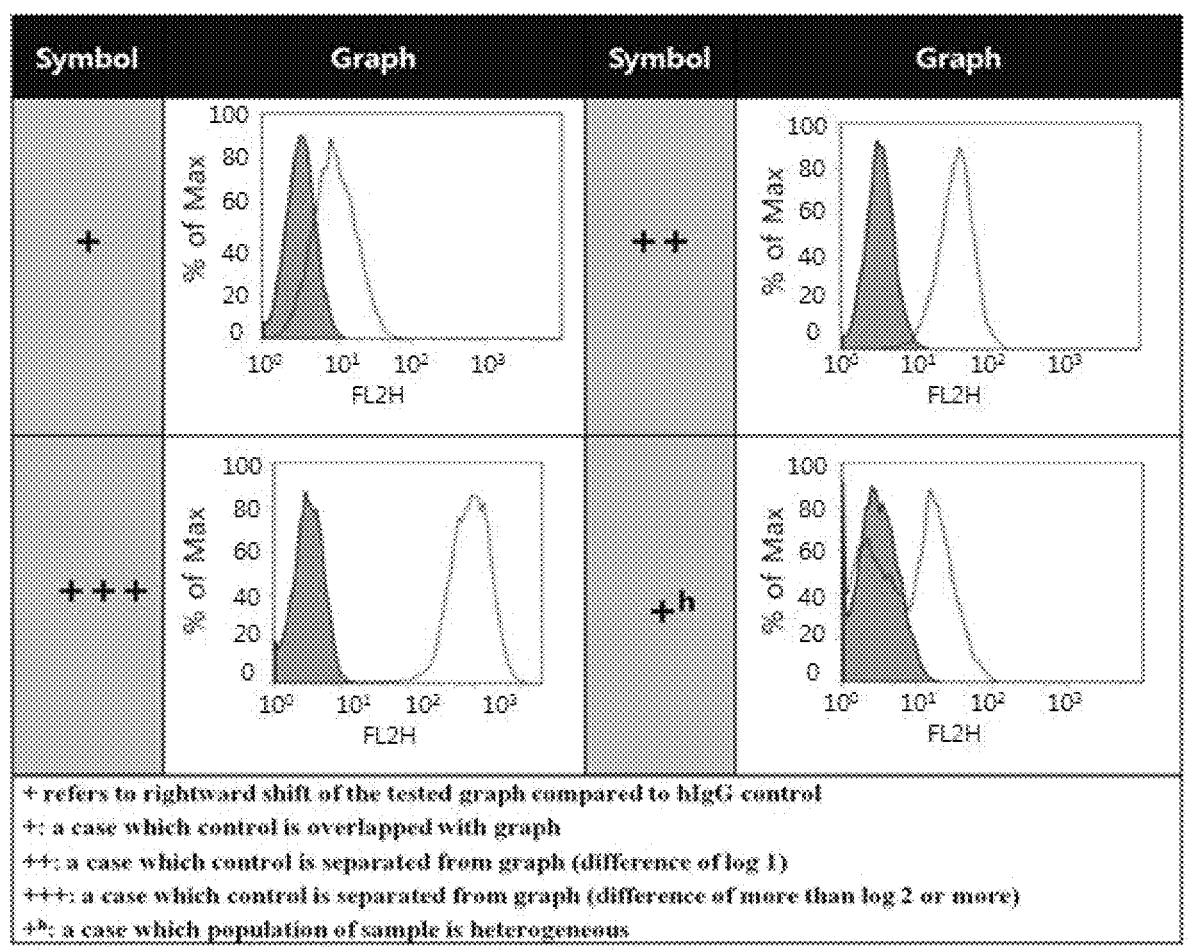

FIG. 10 is a view illustrating results obtained by confirming whether or not the GX102, GX270, and GS012 clone antibodies according to the present invention selectively bind to cell lines in proportion to an expression level of GPC3 in seven kinds of hepatic cancer cell lines (SK-Hep1, PLC/PRF/5, SNU398, Hep3B, Huh7, HepG2, and SK-Hep1-GPC3 #9) and one kind of normal hepatic cancer cell line (CHANG), representing and comparing the results by positive signs depending on an overlapping profile of fluorescence-activated cell sorting (FACS) histogram with that in an isotope negative control group.

DETAILED DESCRIPTION OF THE EMBODIMENTS

As used herein, the term "glypican 3" or "GPC3" collectively indicates arbitrary mutants, isomers, and homologues of glypican 3 as well as GPC3 present in animal, preferably, human bodies, as it is.

As used herein, the term "human GPC3" means GPC3 of a human and preferably has an amino acid sequence (SEQ ID NO: 393) of Genbank accession number AAH35972.1, but is not limited thereto.

The present invention provides an anti-glypican 3 antibody having a heavy chain variable region including a heavy chain CDR1 comprising an amino acid sequence of SEQ ID NO: 133, 143, 149, 159, 169, 174, 184, 199, 262, 268, 273, 281, 285, 291, 297, 308, 353, 363, 374, 380, or 386;
 a heavy chain CDR2 comprising an amino acid sequence of SEQ ID NO:134, 144, 150, 160, 170, 175, 185, 200, 231, 263, 266, 269, 274, 282, 286, 292, 298, 303, 309, 314, 318, 323, 328, 331, 336, 341, 345, 349, 354, 359, 364, 369, 375, 381, or 387; and
 a heavy chain CDR3 comprising an amino acid sequence of SEQ ID NO: 135, 139, 145, 151, 155, 161, 165, 171, 176, 180, 186, 189, 194, 195, 201, 205, 207, 210, 214, 218, 222, 227, 232, 237, 239, 243, 247, 250, 254, 258, 259, 264, 267, 270, 275, 278, 279, 283, 287, 293, 299, 304, 310, 315, 319, 324, 329, 332, 337, 342, 346, 350, 355, 360, 365, 370, 376, 382, or 388.

In another aspect, the present invention provides an anti-glypican 3 antibody having a light chain variable region including a light chain CDR1 comprising an amino acid sequence of SEQ ID NO: 136, 140, 146, 152, 156, 162, 166, 172, 177, 181, 187, 190, 193, 196, 202, 208, 211, 215, 219, 223, 224, 228, 233, 240, 244, 251, 255, 260, 265, 271, 288, 294, 300, 305, 311, 316, 320, 325, 333, 338, 343, 347, 356, 361, 366, 371, 377, 383, or 389;
 a light chain CDR2 comprising an amino acid sequence of SEQ ID NO: 137, 141, 147, 153, 157, 163, 167, 178, 182, 191, 197, 203, 209, 212, 216, 220, 225, 229, 234, 236, 241, 245, 252, 256, 276, 284, 289, 295, 301, 306, 312, 317, 321, 326, 330, 334, 339, 351, 357, 362, 367, 372, 378, 384, 390, or 392; and
 a light chain CDR3 comprising an amino acid sequence of SEQ ID NO: 138, 142, 148, 154, 158, 164, 168, 173, 179, 183, 188, 192, 198, 204, 206, 213, 217, 221, 226, 230, 235, 238, 242, 246, 248, 249, 253, 257, 261, 272, 277, 280, 290, 296, 302, 307, 313, 322, 327, 335, 340, 344, 348, 352, 358, 368, 373, 379, 385, or 391.

Preferably, the anti-glypican 3 antibody according to the present invention has a heavy chain variable region including a heavy chain CDR1 comprising an amino acid sequence of SEQ ID NO: 133, 143, 149, 159, 169, 174, 184, 199, 262, 268, 273, 281, 285, 291, 297, 308, 353, 363, 374, 380, or 386;
 a heavy chain CDR2 comprising an amino acid sequence of SEQ ID NO:134, 144, 150, 160, 170, 175, 185, 200, 231, 263, 266, 269, 274, 282, 286, 292, 298, 303, 309, 314, 318, 323, 328, 331, 336, 341, 345, 349, 354, 359, 364, 369, 375, 381, or 387; and
 a heavy chain CDR3 comprising an amino acid sequence of SEQ ID NO: 135, 139, 145, 151, 155, 161, 165, 171, 176, 180, 186, 189, 194, 195, 201, 205, 207, 210, 214, 218, 222, 227, 232, 237, 239, 243, 247, 250, 254, 258, 259, 264, 267, 270, 275, 278, 279, 283, 287, 293, 299, 304, 310, 315, 319, 324, 329, 332, 337, 342, 346, 350, 355, 360, 365, 370, 376, 382, or 388, and
 a light chain variable region including a light chain CDR1 comprising an amino acid sequence of SEQ ID NO: 136, 140, 146, 152, 156, 162, 166, 172, 177, 181, 187, 190, 193, 196, 202, 208, 211, 215, 219, 223, 224, 228, 233, 240, 244, 251, 255, 260, 265, 271, 288, 294, 300, 305, 311, 316, 320, 325, 333, 338, 343, 347, 356, 361, 366, 371, 377, 383, or 389;
 a light chain CDR2 comprising an amino acid sequence of SEQ ID NO: 137, 141, 147, 153, 157, 163, 167, 178, 182, 191, 197, 203, 209, 212, 216, 220, 225, 229, 234, 236, 241, 245, 252, 256, 276, 284, 289, 295, 301, 306, 312, 317, 321, 326, 330, 334, 339, 351, 357, 362, 367, 372, 378, 384, 390, or 392; and
 a light chain CDR3 comprising an amino acid sequence of SEQ ID NO: 138, 142, 148, 154, 158, 164, 168, 173, 179, 183, 188, 192, 198, 204, 206, 213, 217, 221, 226, 230, 235, 238, 242, 246, 248, 249, 253, 257, 261, 272, 277, 280, 290, 296, 302, 307, 313, 322, 327, 335, 340, 344, 348, 352, 358, 368, 373, 379, 385, or 391.

In another aspect, the anti-glypican 3 antibody according to the present invention, contains a heavy chain variable region having a sequence with a sequence homology of 80% or more, preferably 90% or more, more preferably 95% or more, and most preferably 99% or more with an amino acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, or 131, or
 contains a light chain variable region having a sequence with a sequence homology of 80% or more, preferably 90% or more, more preferably 95% or more, and most preferably 99% or more with an amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, or 132.

Preferably, the anti-glypican 3 antibody according to the present invention
 contains a heavy chain variable region having a sequence with a sequence homology of 80% or more, preferably 90% or more, more preferably 95% or more, and most preferably 99% or more with an amino acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, or 131, and
 a light chain variable region having a sequence with a sequence homology of 80% or more, preferably 90% or more, more preferably 95% or more, and most preferably 99% or more with an amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, or 132.

Further, it is apparent to those skilled in the art that anti-glypican 3 antibodies of which some of the amino acids are substituted, inserted, and/or deleted in the heavy chain and light chain variable regions are also included in the scope of the present invention as long as characteristics such as an affinity and specificity to glypican 3, and the like, satisfying the object of the present invention are maintained. As an example, there is an antibody of which amino acid is conservatively substituted in a variable region. Conservative substitution means substitution with another amino acid residue having similar characteristics as those of an original amino acid sequence. For example, lysine, arginine, and histidine have similar characteristics in that they have basic side chains, and aspartic acid and glutamic acid have similar characteristics in that they have acidic side chains. Further, glycine, asparagines, glutamine, serine, threonine, tyrosine, cysteine, and tryptophane have similar characteristics in that they have uncharged polar side chains, alanine, valine, leucine, threonine, isoleucine, proline, phenylalanine, and methionine have similar characteristics in that they have non-polar side chains, and tyrosine, phenylalanine, tryptophane, and histidine have similar characteristics in that they have aromatic side chains. Therefore, since it is apparent to those skilled in the art that even though an amino acid is substituted with another amino acid in an amino acid group having similar characteristics as described above, there is no particular change in characteristics, an antibody of which mutation is generated by conservative substitution in a variable region is also included in the scope of the present invention as long as the characteristics of the antibody according to the present invention are maintained.

As used herein, the term "antibody", which is an immunoglobulin molecule immunologically reactive with a specific antigen, means a protein molecule serving as a receptor specifically recognizing antigen, and includes a whole antibody thereof and an antibody fragment thereof.

The antibody fragment in the present invention includes a short chain antibody, a diabody, a triabody, a tetrabody, a Fab fragment, a F(ab')$_2$ fragment, Fd, scFv, a domain antibody, a minibody, a scab, an IgD antibody, an IgE antibody, an IgM antibody, an IgG1 antibody, an IgG2 antibody, an IgG3 antibody, an IgG4 antibody, derivatives of an antibody constant region, artificial antibodies based on protein scaffolds, and the like, which have binding affinity to glypican 3, but is not limited thereto. It is apparent to those skilled in the art that as long as binding affinity to glypican 3 is maintained, any type of antibody fragment according to the present invention exhibits the same characteristics as those of the antibody according to the present invention.

Meanwhile, in another aspect of the present invention, there is provide an antibody-drug conjugate (ADC) in which an anti-cancer drug having a tumor cell proliferation suppression effect is bound to the anti-glypican 3 antibody according to the present invention.

The drug capable of being used in the antibody-drug conjugate according to the present invention includes an arbitrary compound, moiety, or group having cytotoxicity or cell proliferation suppression effect, and includes (i) chemotherapeutic agents serving as a microtubulin inhibitor, a mitosis inhibitor, a topoisomerase inhibitor, or a DNA intercalator; (ii) a protein toxin performing an enzymatic function; and (iii) radioisotopes (radionuclides), and the like. One or more of the compounds may be used as the drug.

A non-restrictive example of the drug as described above may include maytansinoid, auristatin, dolastatin, trichothecene, CC1065, calicheamicin and other enediyne antibiotics, taxane, anthracycline, methotrexate, adriamycin, vindesine, *vinca* alkaloids (vincristine, vinblastine, etoposide), doxorubicin, melphalan, mitomycin C, chlorambucil, daunorubicin, daunomycin, etoposide, teniposide, carminomycin, aminopterin, dactinomycin, mitomycins, bleomycins, esperamicins, 5-fluorouracil, melphalan, other nitrogen mustards and stereoisomers, isosteres, analogues, or derivatives thereof, cis-platinum and cis-platinum analogues, enzymes and fragments thereof corresponding to other intercalating agents, for example, nucleolytic enzymes, antibiotics, and toxins (enzymatically active toxins or small molecule toxins of bacterial, fungal, plant or animal origin), various antitumor or anticancer agents such as cisplatin, CPT-11, doxorubicin, paclitaxel, docetaxel, and the like, but is not limited thereto. Further, an example of the radioisotope (radionuclide) includes 3H, 14C, 32P, 35S, 36Cl, 51Cr, 57Co, 58Co, 59Fe, 90Y, 125I, 131I, 186Re, and the like, but is not limited thereto. A micro RNA (miRNA), a small interfering RNA (siRNA), and a small hairpin RNA (shRNA) capable of suppressing expression of a specific oncogene may also be used.

It is preferable that the anti-glypican 3 antibody provided in the present invention and the drug are conjugated to each other using a functional group such as a thiol group, or the like, of an amino acid residue such as lysine or cysteine, in the antibody. In this case, if necessary, the anti-glypican 3 antibody and the drug may also be conjugated to each other in a linker-mediated conjugate using a generally used linker. It is preferable to use a maleimide or iodoacetamide based linker. In the case of conjugating the drug to the antibody or the fragment thereof, it is preferable that the drug is conjugated to a C-terminal site opposite to an antigen binding site so as not to affect binding ability, specificity, and the like, of the antibody or the fragment thereof to glypican 3, and in the case of using the whole antibody instead of the fragment thereof, it is also preferable to conjugate the drug to an Fc region.

In addition, the present invention provides a chimeric antigen receptor (CAR)-based therapeutic agent containing the anti-glypican 3 antibody according to the present invention. For example, the therapeutic agent may be preferably a chimeric antigen receptor T-Cell or chimeric antigen receptor-natural killer (CAR-NK) cell therapeutic agent, but is not limited thereto.

In another aspect of the present invention, there is provided a bispecific antibody containing the anti-glypican 3 antibody according to the present invention. The bispecific antibody is an antibody capable of simultaneously binding to two kinds of antigens, and may be used in a general form in which a pair of different heavy chain and light chain capable of binding to antigens different from each other are linked, and may also be used in a form of a bispecific single chain antibody in which single-chain antibody fragments (scFv) in which VL and VH are linked to each other by a short linker peptide are linked in a form of scFv1-scFv2(-Fc), or a bispecific antibody using a BiTE technology by Micromet Inc. (Germany, see http://www.micromet.de).

The bispecific antibody according to the present invention may be preferably in a form in which the anti-glypican 3 antibody according to the present invention is bound to an antibody having binding ability to an immune effector cell-specific target molecule, or a fragment thereof. The immune effector cell-specific target molecule may be preferably selected from TCR/CD3, CD16(FcγRIIIa) CD44, Cd56, CD69, CD64(FcγRI), CD89, and CD11b/CD18 (CR3), but is not limited thereto.

Further, the present invention provides a gene encoding the variable region of the anti-glypican 3 antibody according to the present invention and a recombinant vector containing the same. A polynucleotide, that is, a gene encoding light chain and heavy chain variable regions of the antibody according to the present invention or the fragment may be easily derived by those skilled in the art from an amino acid sequence of the anti-glypican 3 antibody provided in the present invention.

As used herein, the term "recombinant vector", which is an expression vector capable of expressing a target protein in a suitable host cell, means a genetic construct containing an essential regulatory element to which a genetic insert is operably linked so as to be expressed. The gene encoding the anti-glypican 3 antibody according to the present invention may also be used in a form in which genes are inserted into separate vectors or one vector.

In detail, the polynucleotide encoding the amino acid sequence of the anti-glypican 3 antibody according to the present invention may also be used in a form in which genes are inserted into separate vectors, respectively or inserted into one vector, and may be used in a form in which polynucleotides encoding the heavy chain and light chain, the variable regions thereof, or the like, are inserted into separate vectors, respectively or inserted into one vector.

As used herein, the term "operably linked" means that a nucleic acid expression regulatory sequence and a nucleic acid sequence encoding the target protein are functionally linked to each other so as to perform general functions. Operable linkage with a recombinant vector may be performed using a gene recombination technology wellknown in the art, and site-specific DNA cleavage and linkage may be easily performed using enzymes generally known in the art, or the like.

An expression vector suitable for producing the anti-glypican 3 antibody according to the present invention may include a signal sequence for membrane targeting or secretion in addition to expression regulatory elements such as a promoter, an initiation codon, a termination codon, a polyadenylation signal, and an enhancer. The initiation codon and the termination codon may be generally considered as a portion of a nucleotide sequence encoding an immunogenic target protein, needs to be functional in an individual to whom a genetic construct has been administered, and must be in frame together with the coding sequence. The promoter may be generally constitutive or inducible. An example of the promoter available in prokaryotic cells may include lac, tac, T3, and T7 promoters, but is not limited thereto. An example of the promoter available in eukaryotic cells may include a β-actin promoter, promoters from human hemoglobin, human muscle creatine, and human metallothionein as well as a simian virus 40 (SV40) promoter, a mouse mammary tumor virus (MMTV) promoter, a human immunodeficiency virus (HIV) promoter such as a HIV Long Terminal Repeat (LTR) promoter, a moloney virus promoter, a cytomegalovirus (CMV) promoter, an epstein barr virus (EBV) promoter, a rous sarcoma virus (RSV) promoter, but is not limited thereto.

The expression vector may include a selectable marker for selecting host cells containing the vector. The selective marker is to select cells transformed by the vector, and as the selective marker, markers conferring selectable phenotypes such as drug resistance, nutrient requirement, cytotoxic agent resistance, or expression of surface proteins may be used. Since only cells expressing the selectable marker survive in the environment treated with a selective agent, transformed cells may be selected. Further, in the case of a replicable expression vector, the vector may include a replication origin, which is a specific nucleic acid sequence that initiates replication.

As the recombinant expression vector for inserting a foreign gene, a vector having various shapes such as plasmid, virus, cosmid, and the like, may be used. The kind of recombinant vector is not particularly limited as long as it may serve to express the desired gene and produce the desired protein in various host cells such as prokaryotic cells and eukaryotic cells, but a vector capable of mass-producing a foreign protein having a shape similar to that in a natural state while having a promoter having strong activity and having strong expression ability may be preferable.

Various expression host/vector combinations may be used to express the anti-glypican 3 antibody. An example of the expression vector suitable for eukaryotic cells includes an expression regulatory sequence derived from SV40, bovine papilloma virus, adenovirus, adeno-associated virus, cytomegalovirus, and retrovirus, but is not limited thereto. An example of the expression vector usable in bacteria host cells includes a bacterial plasmid obtained from *Escherichia coli* such as pET, pRSET, pBluescript, pGEX2T, a pUC vector, col E1, pCR1, pBR322, pMB9, and derivatives thereof; plasmids having a broader host range such as RP4; phage DNAs exemplified as various phage lambda derivatives such as λgt10, λgt11, and NM989; and other DNA phages such as M13, single-stranded filament type DNA phage, and the like. An expression vector available in yeast cells may be 2° C. plasmid and a derivative thereof. A vector useful for insect cells may be pVL941.

In another aspect, the present invention provides a host cell transformed with the recombinant vector. The recombinant vector is inserted in a host cell to form a transformant. A host cell suitable for the vector may be a prokaryotic cell such as *Escherichia coli, Bacillus subtilis, Streptomyces* sp., *Pseudomonas* sp., *Proteus mirabilis*, or *Staphylococcus* sp. In addition, the suitable host cells may be eukaryotic cells, for example, fungal cells such as *Aspergillus* sp., yeast cells such as *Pichia pastoris, Saccharomyces cerevisiae, Schizosaccharomyces* sp., and *Neurospora crassa*, other lower eukaryotic cells, and cells of higher eukaryotes such as those from insects. In addition, the host cell may be derived from plants or mammals. Preferably, as the host cell, monkey kidney cells 7 (COS7), NSO cells, SP2/0, Chinese hamster ovary (CHO) cells, W138, baby hamster kidney (BHK) cells, Madin-Darby canine kidney (MDCK) cells, myeloma cell lines, HuT 78 cells, HEK293 cells, and the like, may be used, but the present invention is not limited thereto. Particularly, the CHO cells may be preferable.

As used herein, the term "transformation into host cells" may include any method of introducing nucleic acids into organisms, cells, tissues, or organs, and be performed by selecting standard techniques suitable for the host cell as known in the art. These methods may include an electroporation method, a protoplast fusion method, a calcium phosphate ($CaPO_4$) precipitation method, a calcium chloride ($CaCl_2$)) precipitation method, an agitation method using silicon carbide fiber, an *agrobacterium*-mediated transformation method, and a PEG, dextran sulfate, or lipofectamine and a desiccation/inhibition-mediated transformation method, but are not limited thereto.

In another aspect, the present invention provides a method of preparing the anti-glypican 3 antibody according to the present invention by culturing a host cell transformed with the recombinant vector.

A method of preparing a humanized antibody may include preparing a recombinant vector by inserting a nucleotide sequence encoding the anti-glypican 3 antibody according to the present invention into a vector; transforming a host cell with the recombinant vector to culture a transformant; and separating and purifying a humanized antibody from the cultured transformant.

In detail, the humanized antibody according to the present invention may be massproduced by culturing the transformant in which the recombinant vector is expressed in a nutrient medium. Here, general medium and culturing conditions may be suitably selected depending on the host cell. Conditions such as a temperature, pH of the medium, a culturing time, and the like, may be controlled appropriately for growth of the cells and mass production of proteins at the time of culturing the transformant.

The anti-glypican 3 antibody produced recombinantly as described above may be collected from the medium or cells lysates. In the case of a membrane-binding type anti-glypican 3 antibody, the anti-glypican 3 antibody may be isolated from a membrane by using a suitable surfactant solution (for example, triton-X 100) or enzymatic cleavage. Cells used for expressing the humanized antibody may be destructed by various physical or chemical means such as freezing-thawing acclimation, sonication, mechanical destruction, or a cell lysing agent, and be separated and purified by a general biochemical separation technology (Sambrook et al., Molecular Cloning: A Laboratory Manual, 2nd Ed., Cold Spring Harbor Laboratory Press (1989); Deuscher, M., Guide to Protein Purification Methods Enzymology, Vol. 182. Academic Press. Inc., San Diego, Calif. (1990)). As the separation technology, electrophoresis, centrifugation, gel filtration, precipitation, dialysis, chromatography (ion exchange chromatography, affinity chromatography, immuno-adsorption chromatography, size exclusion chromatography, and the like), isoelectric focusing, and various modification and composite methods thereof, may be used, but the present invention is not limited thereto.

In another aspect, the present invention provides a composition for treating cancer, containing the anti-glypican 3 antibody. As used herein, the term "anti-cancer" includes "prevention" and "treatment". Here, the term "prevention" means all actions for suppressing or delaying cancer diseases by administering the composition containing the antibody according to the present invention, and the term "treatment" means all actions for allowing symptoms of cancer to be alleviated or be advantageously changed by administering the antibody according to the present invention.

The kind of cancer or carcinoma capable of being treated by the composition according to the present invention is not particularly limited, and includes both solid cancer and blood cancer. Preferably, the cancer includes all kinds of cancer in which glypican 3 is expressed, and more preferably, the cancer may be selected from the group consisting of hepatic cancer, hepatocellular carcinoma, gastric cancer, breast cancer, lung cancer, ovarian cancer, bronchial cancer, nasopharyngeal cancer, larynx cancer, pancreatic cancer, bladder cancer, colorectal cancer, colon cancer, uterine cervical cancer, brain cancer, prostate cancer, bone cancer, skin cancer, thyroid cancer, parathyroid cancer, kidney cancer, esophageal cancer, biliary tract cancer, testis cancer, rectal cancer, head and neck cancer, cervical spinal cancer, ureteral cancer, osteosarcoma, neuroblastoma, melanoma, fibrosarcoma, rhabdomyosarcoma, astrocytoma, neuroblastoma and glioma. Most preferably, the cancer capable of being treated with the composition according to the present invention is hepatic cancer or hepatocellular carcinoma.

An anti-cancer composition according to the present invention may further contain a pharmaceutically acceptable carrier. In the case of a formulation for oral administration, a binder, a lubricant, a disintegrant, an excipient, a solubilizer, a dispersant, a stabilizer, a suspending agent, a pigment, a flavoring agent, or the like, may be used, in the case of a formulation for injection, a buffering agent, a preservative, a soothing agent, a solubilizer, an isotonic agent, a stabilizer, or the like, may be mixed and used, and in the case of a formulation for local administration, a base, an excipient, a lubricant, a preservative, or the like, may be used. The formulation of the pharmaceutical composition according to the present invention may be variously prepared by mixing the pharmaceutical composition with the pharmaceutically acceptable carrier as described above. For example, in the case of the formulation for oral administration, the pharmaceutical composition may be prepared in forms of a tablet, a troche, a capsule, an elixir, a suspension, a syrup, a wafer, and the like, and in the case of the formulation for injection, the pharmaceutical composition may be prepared in a form of a unit-dose or multi-dose ampoule or vial. In addition, the anti-cancer composition may contain a surfactant for typically facilitating movement through a membrane. The surfactant as described above may be derived from steroids, or may be a cationic lipid such as N-[1-(2,3-dioleyloxy)propyl]-N,N,N-trimethylammonium chloride (DOTMA), or the like, or various compounds such as cholesterol hemisuccinate, phosphatidyl glycerol, and the like.

In another aspect, the present invention provides a method of treating cancer and suppressing growth of cancer by administering the composition containing the anti-glypican 3 antibody according to the present invention to an individual. A pharmaceutically effective dose of the composition containing the anti-glypican 3 antibody according to the present invention may be administered in order to treat cancer cells or metastasis thereof, or suppress growth of cancer. The pharmaceutically effective dose may be changed by various factors such as the kind of cancer, an age, a weight, characteristics and degree of symptoms of a patient, the kind of current treatment method, a treatment frequency, an administration form and route, and the like, and may be easily determined by a specialist in the corresponding field. The composition according to the present invention may be administered together with the pharmacological or physiological ingredient, or sequentially administered. In addition, the composition according to the present invention and an additional therapeutic agent according to the related art may be combined with each other, and sequentially or simultaneously administered with each other. Administration as described above may be single dose administration or multi-dose administration. It is important to administer the composition at a minimum dose while obtaining a maximum effect without side effects in consideration of all the factors, which may be easily determined by those skilled in the art.

As used herein, the term "individual" means a mammal, preferably, a person in a state or with a disease, which may be alleviated, suppressed, or treated by administrating the humanized antibody or having the risk of the disease.

As used herein, the term "administration" means that a predetermined material is introduced to the individual by an appropriate method, and the composition containing the humanized antibody according to the present invention may be administered through any general route as long as a drug may arrive at a target tissue through the route. Examples of the administration include intraperitoneal administration, intravenous administration, intramuscular administration, subcutaneous administration, intradermal administration, oral administration, topical administration, intranasal administration, intrapulmonary administration, and rectal administration, but are not limited thereto. However, since proteins are digested at the time of oral administration, it is preferable that the composition for oral administration is coated with an active drug or formulated so as to be protected from degradation in the stomach. In addition, the pharmaceutical composition may be administered by an optional device capable of moving an active material to target cells.

Hereinafter, the present invention will be described in detail through the Examples. However, these Examples are only to illustrate the present invention, and those skilled in the art will appreciate that these Examples are not to be construed as limiting a scope of the present invention.

Example 1: Preparation of Anti-Glypican 3 Antibody 1-1: Selection of Anti-Human GPC3 scFv Antibody Using Phage Display An antibody selection process was performed using a phage display technology of inserting a DNA sequence to be expressed into a genome of a bacteriophage parasitic on *E. coli* using a genetic recombinant technology and expressing the inserted protein on a surface of the phage in a form in which the protein is fused with one of coating proteins of the phage. At the time of primary panning, 1 ml of library stock ($10^{13}$ or more) was reacted in a GPC3-coated solid phase polystyrene tube (Nunc, 444202) at 37° C. for 2 hours. At the same time, 10 ul of XLI-Blue electroporation-competent cell (Stratagene) was inoculated into SB (10 ml)/tetracycline (100) and cultured so that OD600 was 0.8 to 1. The reactant at 37° C. for 2 hours was washed with 0.05% Tween 20/PBS (5 ml) four times, and from the secondary panning, as the number of panning was increased, the number of washing with 0.05% Tween 20/PBS (5 ml) was increased. Thereafter, the resultant was cultured in 1% BSA/0.1M Glycine (pH 2.0) at room temperature for 10 minutes, and phagemid was purified. The purified phagemid was transferred into a 50 ml tube and neutralized with 2M tris (70 ul). 9 ml of XLI-Blue Electroporation-Competent Cell (Stratagene) was treated, and 1 ml of XLI-Blue Electroporation-Competent Cell (Stratagene) was treated to the washed tube. After infection at room temperature for 30 minutes, SB (10 ml), tetracycline (20 µl), and carbenicillin (10 µl) were added thereto, and the infected cells were suspension-cultured at 37° C. and 220 rpm for 1 hour. Then, the cultured cells were treated with 1 ml of VCS M13 helper phage (1011 pfu), suspension-cultured at 37° C. and 220 rpm for 1 hour, treated with SB (80 ml), kanamycin (100 µl), and carbenicillin (100 µl), and cultured at 37° C. and 220 rpm for 12 hours or more. The cells cultured for 12 hours or more were centrifuged at 4° C. and 3500 rpm for 10 minutes, a supernatant was transferred to a new tube and 20% PEG/15% NaCl (20 ml) was added thereto and well-mixed, followed by reaction on ice for 30 minutes. Next, a supernatant was removed by centrifugation at 4° C. and 8000 rpm for 30 minutes, and the remaining pellet was collected and re-suspended in 1% BSA/PBS (2 ml), followed by centrifugation at 4° C. and 15000 rpm for 10 minutes. At this time, the collected pellet was removed and 1 ml of a total of 2 ml of supernatant was stored at −20° C., and 1 ml of the supernatant was used in the next panning.

1-2: Securing Individual Clone Using ELISA Method

A single colony from final amplification group of a phage display synthetic scFV library was collected, cultured in SB/carbenicillin (1.5 ml) at 37° C. and 220 rpm until OD 600 was 0.8 to 1.0 or so, and then cultured in 1 mM IPTG at 30° C. and 200 rpm for 12 hours or more. After the reactant was centrifuged at 5500 rpm for 5 minutes, only each of the supernatants was added to an ELISA plated with a GPC3 antigen, reacted at room temperature for 2 hours, and washed with PBST (1×PBS, 0.05% Tween 20) four times. Then, after a HRP/Anti-hFab-HRP conjugate diluted with 1% BSA/1×PBS at a ratio of 1/5000 was added thereto, reacted at room temperature for 1 hour, and washed with PBST (1×PBS, 0.05% Tween 20) four times again, a TMB solution was added thereto, and a reaction was carried out for 5 to 10 minutes. After adding the TMB stop solution thereto, an OD value was measured at a wavelength of 450 nm using a TECAN sunrise, a clone having a high OD value was secured as an individual clone.

As a result, 61 kinds of clones specifically binding to human GPC3 were selected, and amino acid sequences thereof were secured. The selected clones were named as clone GX090, clone GX092, clone GX099, clone GX102, clone GX107, clone GX114, clone GX116, clone GX118, clone GX119, clone GX122, clone GX184, clone GX186, clone GX189, clone GX196, clone GX197, clone GX201, clone GX205, clone GX206, clone GX207, clone GX209, clone GX213, clone GX214, clone GX216, clone GX217, clone GX219, clone GX221, clone GX222, clone GX224, clone GX225, clone GX226, clone GX229, clone GX233, clone GX234, clone GX235, clone GX242, clone GX245, clone GX247, clone GX248, clone GX253, clone GX259, clone GX263, clone GX264, clone GX265, clone GX268, clone GX270, clone GS001, clone GS002, clone GS003, clone GS004, clone GS005, clone GS006, clone GS007, clone GS008, clone GS009, clone GS010, clone GS011, clone GS012, clone GS013, clone GS014, clone GS015, clone GS016, clone GS017, clone GS018, clone GN328, clone GN337, and clone GN414, respectively. A variable region sequence of each of the clones was confirmed as illustrated in Table 1, and a CDR amino acid sequence in the variable region of each of the clones was confirmed as illustrated in Table 2 based on Kabat numbering.

TABLE 1

| Clone | Variable Region | Amino Acid Sequencce | SEQ ID NO: |
|---|---|---|---|
| GX090 | Heavy Chain | QVQLVQSGAEVKKPGASVKVSCKASGYTFTSYGISWVRQAPGQG LEWMGWISAYNGNTNYAQKLQGRVTMTTDTSTSTAYMELRSLRS DDTAVYYCARGSSFSGFDPWGQGTLVTVSS | 1 |

TABLE 1-continued

| Clone | Variable Region | Amino Acid Sequencce | SEQ ID NO: |
|---|---|---|---|
| | Light Chain | QSVLTQPPSLSAAPGQKVTISCSGSSSNIGKNHVSWYQQFPGTA PKFLIYDNHRRPSGIPDRFSGSKSGTSATLDITGLQTGDEATYY CGTWDSSLSAVVFGGGTKLTVLG | 2 |
| GX092 | Heavy Chain | QVQLVQSGAEVKKPGASVKVSCKASGYTFTSYGISWVRQAPGQG LEWMGWISAYNGNTNYAQKLQGRVTMTTDTSTSTAYMELRSLRS DDTAVYYCARADWGFFDYWGQGTLVTVSS | 3 |
| | Light Chain | QSVLTQPPSASGTPGQRVTISCSGSSSNIGSNTVTWYQQLPGTA PKLLIIYANNQRPSGVPDRFSGSKSGTSASLAISGLQSEDEADYY CAAWDDSINGWVFGGGTKLTVLG | 4 |
| GX099 | Heavy Chain | EVQLVESGAEVKKPGASVKVSCKASGYTFTSYYMHMVRQAFGQG LEWMGIINPSGGSTSYAQKFQGRVTMTRDTSTSTVYMELSSLRS EETAVYYCARYSSSPAKIDYWGQGTLVTVSS | 5 |
| | Light Chain | QSVLTQPPSVSAAPGEKVIISCSGSSSNIGKYYVSWYQQLPGTA PKLLIYDNNKRPSGIPDRFSGSKSGTSATLGISGLQTGDEADYY CGTWDSSLNLVFGTGTKVTVLG | 6 |
| GX102 | Heavy Chain | QMQLVQSGAEVKKPGASVKVSCKASGYTFTGYYMHWVRQAPGQG LEWMGWINPNSGGTNYAQKFQGRVTMTRDTSISTAYMELSRLRS DDTAVYYCARRGLRGDFDYWGQGTLVTVSS | 7 |
| | Light Chain | GQSVLTQPPSASETPGQKVTISCSGSSSNIGTNHVFWYQQLPGT APKLLIYRNNLRPSGVPDRFSGSKSGTSASLAISGLRSEDEADY YCAAWDDSLSWVFGGGTKLTVLG | 8 |
| GX107 | Heavy Chain | QMQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARSHGDYPEDYWGQGTLVTVSS | 9 |
| | Light Chain | YELTQPPSVSVSPGQTARIACSGDALPKHYAYWYQQKSGQAPVL VVYEDKKRPAGIPERFSGSSSGTVATLTISGAQVEDEAHYYCYS TDTSGNHRVFGGGTKLTVLG | 10 |
| GX114 | Heavy Chain | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARVVDSSDYWGQGTLVTVSS | 11 |
| | Light Chain | AIQMTQSPSSLSASVGDRVTITCQASQDISNYLNWYQQKPGKAP KLLIYDASNLETGVPSRFSGSGSGTDFTFTISSLQPEDIATYYC QQYDNLPLTFCGGTKVEIKR | 12 |
| GX116 | Heavy Chain | QVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARVMVRGVSTFGYWGQGTLVTVSS | 13 |
| | Light Chain | QSVLTQPPSVSAAPGQKVSISCSGSSSNIGKNFLSWYQQLPGTA PHLLIYRNNRRPSGIPDRFSGSKSGTSATLTITGLQTGDEGDYY CGAWDSRLSGVVFGGGTKLTVLG | 14 |
| GX118 | Heavy Chain | QLQLQESGPGLVKPSETLSLTCTVSGGSISSSSYYWGWIRQPPG KGLEWIGSIYYSGSTYYNPSLKSRVTISVDTSKNQFSLKLSSVT AADTAVYYCARLRSFADNYWGSYASYYFDYWGRGTLVTVSS | 15 |
| | Light Chain | QSVVTQPPSVSAAPGQRVTISCSGSSSNIGNNFVSWHQQLPGTA PKLLIYDNNKRPSGIPDRFSGSKSGTSATLGITGLQTGDEADYY CGTWDNSLGTGVFGGGTKLTVLG | 16 |
| GX119 | Heavy Chain | EVQLVESGGGVVQPGRSLRLSCAASGFTFSSYGMHWVRQAPGKG LEWVAVIWYDGSNKYYADSVKGRFTISRDNSKNTLYLQMNSLRA EDTAVYYCARDRSWNYYGMDVWGQGTTVTVSS | 17 |
| | Light Chain | AIRMTQSPSSLSASVGDRVTITCRASQSISSYLNWYQQKPGKAP KLLIYAASSLQSGVPSRFSGSGSGTDFTLTISSLQPEDFATYYC QQSYSTPVTFGGGTKLEIKR | 18 |
| GX122 | Heavy Chain | EVQLVESGAEVKKPGASVKVSCKASGYTFTSYYMHWVRQAPGQG LEWMGIINPSGGSTSYAQKFQGRVTMTRDTSTSTVYMELSSLRS EDTAVYYCARDGGSSPDIWGQGTMVTVSS | 19 |
| | Light Chain | SYELTQPPSVSVSPGQTARITCSGDALPKKYAYWYQQKSGQAPV LVIYEDKKRPSEIPERFSGSSSGTMATLTITGAQVDDEADYYCY SIDRSGSRGVFGGGTKLTVLG | 20 |
| GX184 | Heavy Chain | QLQLQESGPGLVEPSETLSLTCAVSGGSISSSNNYWGWIRQPPG KGLEWIGSIFYSGSTYYNPSLKSRVTISVDTSKNQFSLKLSSVT AADTAVYYCARLPTGTPGFYFDYWGQGTLVTVSS | 21 |
| | Light Chain | SYELTQPPSVSKGLRQTATLTCTGNSNNVGNQGAAWLQQHQGHP PKLLSYRNNNRPSGISERFSASRSGNTASLTITGLQPEDEADYY CSAWDSSLSAWVFGGGTKLTVLG | 22 |

TABLE 1-continued

| Clone | Variable Region | Amino Acid Sequencce | SEQ ID NO: |
|---|---|---|---|
| GX186 | Heavy Chain | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARLQGYWGRGTLVTVSS | 23 |
| | Light Chain | DIQMTQSPDSLAVSLGERATINCKSSQSVLYSSNNKNYLAWYQQ KPGQPPKLLIYWASTRESGVPDRFSGSGSGTDFTLTISSLQAED VAVYYCQQYYSTPPTFGGGTKLEIKR | 24 |
| GX189 | Heavy Chain | QLQLQESGPGLVKPSETLSLTCAVSGGSISSSNNYWGWIRQPPG KGLEWIGSIFYSGSTYYNPSLKSRVTISVDTSKNQFSLKLSSVT AADTAVYYCARLPTGTPGFYFDYWGQGTLVTVSS | 25 |
| | Light Chain | SYVLTQPPSVSKGLRQTATLTCTGNSSNVGNQGAAWLQQHQGHP PKLLSYRNNNRPSGISERFSASKSGNTASLTITGLRPEDEADYY CSAWDSSLSAWVFGGGTKLTVLG | 26 |
| GX196 | Heavy Chain | EVQLVESGGGLVKPGGSLRLSCAASGFTFSDYYMSWIRQAPGKG LEWVSYISSSGSTIYYADSVKGRFTISRDNAKNSLYLQMNSLRD EDTAVYYCARVTGDYWGRGTLVTVSS | 27 |
| | Light Chain | EIVMTQSPDSLAVSLGERATINCKSSQSVLYSSNNKNYLAWYQQ KPGQPPKLLIYWASTRESGVPDRFSGSGSGTDFTLTISSLQAED VAVYYCQQYYSTPLIFGGGTKVEIKR | 28 |
| GX197 | Heavy Chain | QVQLVQSGAEVKKPGASVKVSCKASGYTFTSYGISWVRQAPGQG LEWMGWISAYNGNTNYAQKLQGRVIMTTDTSTSTAYMELRSLRS DDTAVYYCASQGSGWLDYWGQGTLVTVSS | 29 |
| | Light Chain | NFMLTQPHSVSESPGKTVTISCTGSGGNIASNYVQWFQQRPGSA PTTVIYDDVQRPSGVPNRFSGSIDSSSNSASLSISGLKTEDEAD YYCQSYDRTYRGVFGGGTKLTVLG | 30 |
| GX201 | Heavy Chain | QVQLVESGGGLVNPGGSLRLSCAASGFTFSNYGMNWVRQAPGKG LEWVSSISTRSGYIFYADSVKGRFTISRDNAKNSLYLQMNSLRA EDTAVYYCARDRPNRSGMDVWGQGTTVTVSS | 31 |
| | Light Chain | QSALTQPASVSGSPGQSITISCTGTSSDVGGYNYVSWYQQHPGK APKLMIYDVSNRPSGVSNRFSGSKSGNTASLTISGLQAEDEGDY YCSSYTSSDTLVFGSGTKVTVLG | 32 |
| GX205 | Heavy Chain | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARVLLDYWGQGTLVTVSS | 33 |
| | Light Chain | AIQMTQSPSSLSASVGDRVTITCQASQDISNYLNWYQQKFGKAP KLLIYDASNLETGVPSRFSGSGSGTDFTFTISSLQPEDIATYYC QQYDNLLLTFGGGTKLEIKR | 34 |
| GX206 | Heavy Chain | QLQLQESGPGLVKPSETLSLTCTVSGGSISSSSYYWGWIRQPPG KGLEWIGSIYYSGSTYYNPSLKSRVTISVDTSKNQFSLKLSSVT AADTAVYYCARLGDYGGNGYYFDYWGQGTLVTVSS | 35 |
| | Light Chain | QSVLTQPPSVSAASGQKVTVSCSGSSSNIGKNGVSWHQQLPGTA PKLLIYENNRRPSEIPDRFSGSKSGTSATLAITGLQTGDEADYY CGTWDSSLNAGVFGTGTKVTVLG | 36 |
| GX207 | Heavy Chain | EVQLVQSGAEVKKPGASVKVSCKASGYTFTSYGISWVRQAPGQG LEWMGWISAYNGNTNYAQKLQGRVTMITDTSTSTAYMELRSLRS DDTAVYYCAREGIAAAGYYYGMDVWGQGTTVTVSS | 37 |
| | Light Chain | QSALTQPPSVSGSPGQSVTISCTGTSSDVGGYNRVSWYQQPPGT APKLMIYEVSNRPSGVPDRFSGSKSGNTASLTISGLQAEDEADY YCSSYTSSTTYVFGTGTKVTVLG | 38 |
| GX209 | Heavy Chain | QVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARGYYYGMDVWGQGTTVTVSS | 39 |
| | Light Chain | QSVLTQPPSASVSPGQTASITCSGDKLGDKYVFWYRQKPGQSPV LVIYQDNKRPSGIPERFSGSNSGNTATLTISGTQAMDEADYYCQ TWDSSTEVFGTGTKVTVLG | 40 |
| GX213 | Heavy Chain | QLQLQESGPGLVKPSETLSLTCTVSGGSISSSSYYWGWIRQPPG KGLEWIGSIYYSGSTYYNPSLKSRVTISVDTSKNQFSLKLSSVT AADTAVYYCARLFWQQLTFDYWGQGTLVTVSS | 41 |
| | Light Chain | QSVVTQPPSVSAAPGQRVSISCSGSSSNIGKNHVIWHQQFPGTA PKLLISENNKRPSGIPDRFSASKSGTSATLDITGLQTGDEADYY CGTWDNSLSAGVFGGGTKLTVLG | 42 |
| GX214 | Heavy Chain | EVQLVESGGGLVKPGGSLRLSCAASGFTFSDYYMSWIRQAPGKG LEWVSYISSSGSTIYYADSVKGRFTISRDNAKNSLYLQMNSLRV DDTAVYYCATLYDFWSQGTLVTVSS | 43 |
| | Light | NIQMTQSPSSLSASVGDRVTITCQASQDITNFLNWHQQKPGKAP | 44 |

TABLE 1-continued

| Clone | Variable Region | Amino Acid Sequencce | SEQ ID NO: |
|---|---|---|---|
| | Chain | ELLIYDASNLETGVPSRFSGSGSGTDFTFTISSLQPEDVGTYYC QQYDNLPLTFGGGTKVEIKR | |
| GX216 | Heavy Chain | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARVVDSSDYWGQGTLVTSS | 45 |
| | Light Chain | EIVLTQSPATLSLSPGESATLSCRASQSVSSYLAWYQQKPGQAP RLLIYDASNRATGIPARFSGSGSGTDFTLTISSLEPEDFAVYYC QQRSNWPPVALTFGGGTKLEIKR | 46 |
| GX217 | Heavy Chain | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARVSGDPKDWGQGTLVTSS | 47 |
| | Light Chain | DIVMTQSPATLSVSPGERATLSCRASQSVSSNLAWYQQKPGQAP RLLIYGASTRATGIPARFSGSGSGTEFTLTISSLQSEDFAVYYC QQYNNWPRELFGPGTKVDIKR | 48 |
| GX219 | Heavy Chain | QMQLVQSGAEVKKPGASVKVSCKASGYTFTGYYMHWVRQAPGQG LEWMGRINPNSGGTNYAQKFQGRVTMTRDTSISTAYMELSRLRS DDTAVYYCARVARYCSSTSCRTGGMDVWGQGTTVTVSS | 49 |
| | Light Chain | QSVLTQPPSASGTPGQRVTISCSGRSSNIGSRYVYWYQQLTGTA PKLLIFRNDQRPSGVPDRFSASKSGTSASLAISGLRSEDEADYF CATWDDSLSAWVFGGGTKLTVLG | 50 |
| GX221 | Heavy Chain | QLQLQESGPGLVKPSETLSLTCAVSGGSISSSNNYWGWIRQPPG KGLEWIGSIFYSGSTYYNPSLKSRVTISVDTSKNQFSLKLSSVT AADTAVYYCARLPTGTPGFYFDYWGQGTLVTVSS | 51 |
| | Light Chain | SYVLTQPPSVSKDLRQTATLTCTGNSSNVGNQGAAWVQQHQGHP PKLLSYRNNKRPSGISERLSASRSGNTASLTITGLQPEDEADYY CSAWDSSLSAWVFGGGTKLTVLG | 52 |
| GX222 | Heavy Chain | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARVTLDYWGRGTLVTVSS | 53 |
| | Light Chain | AIRMTQSPSSLSASVGDRVTITCQASQDISNYLNWYQQKPGKAP KLLIYDASNLETGVPSRFSGSGSETDFTFTISSLQPEDIATYYC QQYDSLPTTFGPGTKVDIKR | 54 |
| GX224 | Heavy Chain | QVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARSRPRSSSFDYWGRGTLVTVSS | 55 |
| | Light Chain | NFMLTQPHSVSESPGKTVTISCTVSSGSIAKNYVHWYQRRPGSA PTPLIYEDNRRPSGVPDRFSGSIDSSSNSASLTISGLKTEDEAD YYCQSYDDSGDRFVFGTGTKVTVLG | 56 |
| GX225 | Heavy Chain | QVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARESGPSGGMDVWGQGTTVTVSS | 57 |
| | Light Chain | SYELTQPPSVSVSPGQTARITCSGDALPKQYAYWYQQKPGQAPV LVIYKDSERPSGIPERFSGSSSGTTVTLTISGVQAEDEADYYCS SYTSSSTRVVFGGGTKLTVLG | 58 |
| GX226 | Heavy Chain | EVQLVESGGGLVKPGGSLRLSCAASGFTFSDYYMSWIRQAPGKG LEWVSYISSSGSTIYYADSVKGRFTISRDNAKNTLYLQMNSLRA EDTAVYYCARVTLDYWGRGTLVTVSS | 59 |
| | Light Chain | DIVMTQSPSSLSASVGDRVTITCQASQDISNYLNWYQQKPGKAP KLLIYDASNLETGVPSRFSGSGSGTDFTFTISSLQPEDIATYYC QQYDNLPSITFGQGTRLEIKR | 60 |
| GX229 | Heavy Chain | EVQLVESGGGLVKPGGSLRLSCAASGFTFSDYYMSWIRQAPGKG LEWVSYISSSGSTIYYADSVKGRFTISRDNSKNTLYLQMNSLRA EDTAVYYCARVLLDYWGQGTLVTVSS | 61 |
| | Light Chain | DIVMTQSPSSLSASVGDRVTITCQASQDISNYLNWYQQKPGKAP KLLIYDASNLETGVPSRFSGSGSGTDFTFTISSLQPEDIATYYC QQYDNLWLTFGGGTKLEIKR | 62 |
| GX233 | Heavy Chain | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARVVDSSDYWGQGTLVTVSS | 63 |
| | Light Chain | AIQMTQSPSSLSASVGDRVTITCQASQDISNYLNWYQQKPGKAP KLLIYDASNLETGVPSRFSGSGSGTDFTLRISRVEAEDVGIYYC MEVRYWPYNFGQGTKLEIKR | 64 |
| GX234 | Heavy Chain | QVQLVQSGAEVKKPGASVKVSCKASGYTFTSYGISWVRQAPGQG LEWMGWISAYNGNTNYAQKLQGRVTMTTDTSTSTAYMELRSLRS DDTAVYYCARVGLGDFWSGDYYYYYGMDVWGQGTTVTVSS | 65 |

TABLE 1-continued

| Clone | Variable Region | Amino Acid Sequence | SEQ ID NO: |
|---|---|---|---|
| | Light Chain | SSELTQDPAVSVALGQTVRITCQGDSLRSSYASWYHQKPGQAPV LVMYGKNNRPSGIPDRFSGSSSGNTASLTITGAQAEDEADYYCH SRDSTGSHPNWVFGGGTKLTVLG | 66 |
| GX235 | Heavy Chain | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARVSGDPKDWGQGTLVTVSS | 67 |
| | Light Chain | AIQMTQSPDSLAVSLGERATINCKSSQSVLYSSNNKNYLAWYQQ KPGQPPKLLIYWASTRESGVPDRFSGSGSGTDFTLTISSLXAED VAVYYCQQYYSTPLTFGGGTKLEIKR | 68 |
| GX242 | Heavy Chain | QVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARVVAAREDYWGQGTLVTVSS | 69 |
| | Light Chain | EIVLTQSPATLSLSPGERATLSCRATQSVGSYLAWYQQKPGQAP RLLIYDAFNRATGIPDRFSGSGSGTDFTLTISSLEPEDFAVYYC QQRSNWPLTFGGGTKVEIKR | 70 |
| GX245 | Heavy Chain | QVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARVSDDSPYWGQGTLVTVSS | 71 |
| | Light Chain | VIVWMTQSPSSLSASVGDRVTITCQASQDISNYLNWYQQKPGKAP KLLIYDASNLETGVPSRFSGSGSGTDFTFTISSLQPEDIATYYC QQYDNLLALTFGGGTKLEIKR | 72 |
| GX247 | Heavy Chain | QVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARTRKGSGYSYGYGMDVWGQGTTVTVSS | 73 |
| | Light Chain | SYELTQPPSVSVSPGQTASITCSGDKLGNKYVSWYQQKPGQSPV LVIYQDNKRPSGIPERFSGSNSGNTATLTISGTQAMDEAGYYCQ TWDSSVVFGGGTKLTVLG | 74 |
| GX248 | Heavy Chain | QMQLVQSGAEVKKPGASVKVSCKASGGTFSSYAISWVRQAPGQG LEWMGGIIPIFGTANYAQKFQGRVTITADESTSTAYMELSSLRS EDTAVYYCARVRGTGPRGGTFDYWGQGTLVTVSS | 75 |
| | Light Chain | QSVLTQPPSVSAAPGQKVTISCSGSSSNIGNNYVSWYQQLPGTA PKLLIYDNNKRPSGIPDRFSGSKSGTSATLGITGLQTGDEADYY CGTWDSSLSAWVFGGGTKLTVLG | 76 |
| GX253 | Heavy Chain | EVQLVESGGGLVKPGGSLRLSCAASGFTFSDYYMSWIRQAPGKG LEWVSYISSSGTTIYYADSVKGRFTISRDNAKKSLYLQMNSLRA EDTAVYYCARVRDSSGFWGRGTLVTVSS | 77 |
| | Light Chain | QSVLTQPPSVSAAPGQKVTISCSGSSSNIGNNYVSWYQQLPGTA PKLLIYDNNKRPSGIPDRFSGSKSGTSATLGITGLQTGDEADYY CGTWDSSLSAWVVGGGTKLTVLG | 78 |
| GX259 | Heavy Chain | QVQLVQSGAEVKKPGESLRISCKASGYKFTNYWIAWVRQMPGKG LEWMGIIYPGDSDTRYSPSLQGQVTISADKSITTAYLQWSSLRA SDTAMYYCATIGLREGRWGQGTLVTVSS | 79 |
| | Light Chain | AIQMTQSPSSLSASVGDRVTITCRASQGISNYLAWYQQYPGKAP KLLIYDASNLETGVPSRFSGSGSGTDFTFTISSLQPEDIATYYC QQYDNTLPFGQGTKLEIKR | 80 |
| GX263 | Heavy Chain | EVQLVESGGGLVKPGGSLRLSCAASGFTFSSYSMNWVRQAPGKG LEWVSSISSSSSYIYYADSVKGRFTISRDNAKNSLYLQMNSLRA EDTAVYYCARVTPYYYYGMDVWGQGTTVTVSS | 81 |
| | Light Chain | QSVVTQPPSVSAAPGQKVTISCSGSSSNIGNNYVSWYQQLPGTA PKLLIYDSNKRPPGIPDRFSGSKSGTSATLGITGLQTGDEADYY CGAWDSSLSAVVFGGGTKLTVLG | 82 |
| GX264 | Heavy Chain | QLQLQESGPGLVKPSETLSLTCTVSGGSISSSSYYWGWIRQPPG KGLEWIGSIYYSGSTYYNPSLKSRVTISVDTSKNQFSLKLSSVT AADTAVYYCARLRWYSYGYFDVRGGYYFDYWGRGTLVTVSS | 83 |
| | Light Chain | QSVLTQPPSVSAASGQKVTVSCSGSSSNIGKNGVSWHQQLPGTA PKLLIYENNRRPSEIPDRFSGSKSGTSATLAITGLQTGDEADYY CGTWDSSLNAGVFGTGTKVTVLG | 84 |
| GX265 | Heavy Chain | QVQLVQSGGGLVKPGGSLRLSCAASGFTFSDYYMSWIRQAPGKG LEWVSYISSSGSTIYYADSVKGRFTISRDNAKNSLYLQMNSLRA EDTAVYYCARVHLDYWGQGTLVTVSS | 85 |
| | Light Chain | DIVMTQSPDSLAVSLGERATINCKSSQSVLYSSNNKNYLAWYQQ KPGQPPKLLIYWASTRESGVPDRFSGSGSGTDFTLTISSLQAED VAVYYCQQYYSTPPTFGQGTKVEIKR | 86 |

TABLE 1-continued

| Clone | Variable Region | Amino Acid Sequencce | SEQ ID NO: |
|---|---|---|---|
| GX268 | Heavy Chain | EVQLVESGGGVVQPGRSLRLSCAASGFTFSSYGMHWVRQAPGKG LEWVAVIWYDGSNKYYADSVKGRFTISRDNSKNTLYLQMNSLRA EDTAVYYCARDRSWNYYGMDVWGQGTTVTVSS | 87 |
| | Light Chain | NIQMTQSPSSLSASVGDRVTITCRASQSISSYLNWYQQKPGKAP KLLIYAASSLQSGVPSRFSGSGSGTDFTLTISSLQPEDFATYYC QQSYSTPTFGQGTRLEIKR | 88 |
| GX270 | Heavy Chain | QVQLVQSGAEVKKPGASVKVSCKTSGYTFTSSYMHWVRQAPGQG LEWMGIINPNSRGTNYAQKFQGRVTMTSDTSISTAYMELSSLIS DDTAVYYCASSSGDYPDYWGQGTLVTVSS | 89 |
| | Light Chain | SYELTQPPSVSVSPGQTARIACSGDALPKHYAYWYQQKSGQAPV LVVYEDKKRPAGIPERFSGSSSGTVATLTISGAQVEDEAHYYCY STDTSGNHRVFGGGTKLTVLG | 90 |
| GS001 | Heavy Chain | EVQLLESGGGLVQPGGSLRLSCAASGFTFSSYSMSWVRQAPGKG LEWVSGISPSGGNKYYADSVKGRFTISRDNSKNTLYLQMNSLRA EDTAVYYCARALLGCKSAYCYYAMDVWGQGTLVTVSS | 91 |
| | Light Chain | QSVLTQPPSASGTPGQRVTISCTGSSSNIGSNAVNWYQQLPGTA PKLLIYADSKRPSGVPDRFSGSKSGTSASLAISGLRSEDEADYY CGSWDSSLSGYVFGGGTKLTVLG | 92 |
| GS002 | Heavy Chain | EVQLLESGGGLVQPGGSLRLSCAASGFTFSGYSMSWVRQAPGKG LEWVSSISPGGSSTYYADSVKGRFTISRDNSKNTLYLQMSSLRA EDTAVYYCARYRVWHMTTGDYYSNAMDVWGQGTLVTVSS | 93 |
| | Light Chain | QSVLTQPPSASGTPGQRVTISCTGSSSNIGSNAVSWYQQLPGTA PKLLIYDDNKRPSGVLDRFSGSKSGTSASLAISGLRSEDEADYY CGTWDDSLSGYVFGGGTKLTVLG | 94 |
| GS003 | Heavy Chain | EVQLLESGGGLVQPGGSLRLSCAASGFTFSNYSMSWVRQAPGKG LEWVSVISPGSGSTYYADSVKGRFTISRDNSKNTLYLQMNSLRA EDTAVYYCARYRVMRSPHNPYYSYGMDVWGQGTLVTVSS | 95 |
| | Light Chain | QSVLTQPPSASGTPGQRVTISCSGSSSNIGSNDVNWYQQLPGTA PKLLIYSNSQRPSGVPDRFSGSKSGTSASLAISGLRSEDEADYY CGSWDASLSGYVFGGGTKLTVLG | 96 |
| GS004 | Heavy Chain | EVQLLESGGGLVQPGGSLRLSCAVSGFTFSNYSMSWVRQAPGKG LEWVSAISPGSSNKYYADSVKGRFTISRDNSKNTLYLQMNSLRA EDTAVYYCARYRVWAHSASSSYSNAMDVWGQGTLVTVSS | 97 |
| | Light Chain | QSVLTQPPSASGTPGQRVTISCSGSSSNIGNNDVSWYQQLPGTA PKLLIYSDSQRPSGVPDRFSGSKSGTSASLAISGLRSEDEADYY CGSWDDSLNGYVFGGGTKLTVLG | 98 |
| GS005 | Heavy Chain | EVQLLESGGGLVQPGGSLRLSCAASGFTFSNYAMSWVRQAPGKG LEWVSVISPDSSKYYADSVKGRFTISRDNSKNTLYLQMNSLRA EDTAVYYCARAAVRRYGPSPYYYYAMDVWGQGTLVTVSS | 99 |
| | Light Chain | QSVLTQPPSASGTPGQRVTISCTGSSSNIGNNYVTWYQQLPGTA PKLLIYADSHRPSGVPDRFSGSKSGTSASLAISGLRSEDEADYY CATWDYSLSGYVFGGGTKLTVLG | 100 |
| GS006 | Heavy Chain | EVQLLESGGGLVQPGGSLRLSCAASGFTFSGYSMSWVRQAPGKG LEWVSAISPGGGSKYYADSVRGRFTVSRDNSKNTLYLQMNSLRA EDTAVYYCARYRVQKSAKNVYSSNGMDVWGQGTLVTVSS | 101 |
| | Light Chain | QSVLTQPPPASGTPGQRVTISCSGSSSNIGNNAVNWYQQLPGTA PKLLIYYDSNRPSGVPDRFSGSKSGTSASLAISGLRSEDEADYY CGAWDSSLSAYVFGGGTKLTVLG | 102 |
| GS007 | Heavy Chain | EVQLLESGGGLVQPGGSLRLSCAASGFTFSNYSMSWVRQAPGKG LEWVSVISHDGRSKYYADSVKGRFAISRDNSKNTLYLQMNSLRA EDTAVYYCAKFRVWKRTNAHSYANAMDVWGQGTLVTVSS | 103 |
| | Light Chain | QSVLTQPPSASGTPGQRATISCTGSSSNIGSNSVSWYQQLPGTA PKLLIYANSNRPSGVPDRFSGSKSGTSASLAISGLRSEDEADYY CGTWDASLSAYVFGGGTKLTVLG | 104 |
| GS008 | Heavy Chain | EVQLLESGGGLVQPGGSLRLSCAASGFTFSNYAMSWVRQAPGKG LEWVSVISPDNGSTYYADSVKGRFTISRDNSKNTLYLQMNSLRA EDTAVYYCARARVHCRRDQCYSYGMDVWGQGTLVTVSS | 105 |
| | Light Chain | QSVLTQPPSASGTPGQRVTISCTGSSSNIGSNNVTWYQQLPGTA PKLLIYANSQRPSGVPDRFSGSKSGTSASLAISGLRSEDEADYY CGAWDSSLNGYVFGGGTKLTVLG | 106 |
| GS009 | Heavy Chain | EVQLLESGGGLVQPGGSLRLSCAASGFTFSNYSMSWVRLAPGKG LEWVSVISPSGGNTYYADSVKGRFTISRDNSKNTLYLQMNSLRA EHTAVYYCARYRVKQMLNQRSYSNAMDVWGQGTLVTVSS | 107 |
| | Light | QSVLTQPPSASGTPGQRVTISCTGSSSNIGNNYVSWYQQLPGTA | 108 |

TABLE 1-continued

| Clone | Variable Region | Amino Acid Sequencce | SEQ ID NO: |
|---|---|---|---|
| | Chain | PKLLIYDDSQRPSGVPDRFSGSKSGTSASLAISGLRSEDEADYY CGSWDASLSGYVFGGGTKLTVLG | |
| GS010 | Heavy Chain | EVQLLESGGGLVQPGGSLRLSCAASGFTFSNYSMSWVRQAPGKG LEWVSVISPSSGSIYYADSVKGRFTISRDNSKNTLYLQMNSLRA EDTAVYYCARYRVRQLKHTRSYADAMDVWGQGTLVTVSS | 109 |
| | Light Chain | QSVLTQPPSASGAPGQRVTISCGSSSNIGSNAVSWYQQLPGTA PKLLIYANSHRPSGVPDRFSGSKSGTSASLAISGLRSEDETDYY CASWDSSLSGYVFGGGTKLTVLG | 110 |
| GS011 | Heavy Chain | EVQLLESGGGLVQPGGSLRLSCAASGFTFSNYAMSWVRQAPGKG LEWVSGISPGGSSIYYADSVKGRFTISRDNSKNTLYLQMNSLRA EDTAVYYCARYAVYFLRSHGSYDYGMDVWGQGTLVTVSS | 111 |
| | Light Chain | QSVLTQPPSASGTPGQRVTISCTGSSSNIGSNDVTWYQQLPGTA PKLLIYSNNQRPSGVPDRFSGSKSGTSASLAISGLRSEDEADYY CGAWDYSLNAYVFGGGTKLTVLG | 112 |
| GS012 | Heavy Chain | EVQLLESGGGLVQPGGSLRLSCAASGFTFSNYSMSWVRQAPGKG LEWVSGISPGSGSKYYADSVRGRFTVSRDNSKNTLYLQMNSLRA EDTAVYYCARRARRFDYWGQGTLVTVSS | 113 |
| | Light Chain | QSVLTQPPSASGTPGQRVTISCTGSSSNIGNNAVTWYQQLPGTA PKLLIYSNSQRPSGVPDRFSGSKSGTSASLAISGLRSEDEADYY CGSWDSSLNGYVFGGGTKLTVLG | 114 |
| GS013 | Heavy Chain | EVQLLESGGGLVQPGGSLRLSCAASGFTFSNYAMSWVRQAPGKG LEWVSSISSGGGSTYYADSVKGRFTISRDNSKNTLYLQMNSLRA EDTAVYYCARKKSQFDYWGQGTLVTVSS | 115 |
| | Light Chain | QSVLTQPPSASGTPGQRVTISCGSSSNIGSNTVNWYQQLPGTA PKLLIYANSQRPSGVPDRFSGSKSGTSASLAISGLRSEDEADYY CDTWDYSLSGYVFGGGTKLTVLG | 116 |
| GS014 | Heavy Chain | EVQLLESGGGLVQPGGSLRLSCAASGFTFSNYAMSWVRQAPGKG LEWVSVISPNSGSNTYYADSVKGRFTISRDNSKNTLYLQMNSLR AEDTAVYYCARPRILRRRVDHSYSYAMDVWGQGTLVTVSS | 117 |
| | Light Chain | QSVLTQPPSASGTPGQRVTISCTGSSSNIGNNYVSWYQQLPGTA PKLLIYSNSHRPSGVPDRFSGSKSGTSASLAISGLRSEDEADYY CGTWDYSLSGYVLGGGTKLTVLG | 118 |
| GS015 | Heavy Chain | EVQLLESGGGLAQPGGSLRLSCAASGFTFSDYSMSWVRQAPGKG LEWVSAISPDGGSKYYADSVKGRFTISRDNSKNTLYLQMNSLRA EDTAVYYCARFRVIKLRAGWYSANGMDVWGQGTLVTVSS | 119 |
| | Light Chain | QSVLTQPPSASGTPGQRVTISCGSSSNIGNNDVSWYQQLPGTA PKLLIYYNSKRPSGVPDRFSGSKSGTSASLAISGLRSEDEADYY CGAWDDSLNGYVFGGGTKLTVLG | 120 |
| GS016 | Heavy Chain | EVQLLESGGGLVQPGGSLRLSCAASGFTFSNYAMSWVRQAPGKG LEWVSGIYSGNGNTYYADSVKGRFTISRDNSKNTLYLQMNSLRA EDTAVYYCARALSSCPRGPCYYDDGMDVWGQGTLVTVSS | 121 |
| | Light Chain | QSVLTQPPSASGTPGQRVTISCGSSSNIGSNDVIWYQQLPGTA PKLLIYDNSKRPSGVPDRFSGSKSGTSASLXISGLRSGDEADYY CGTWDASLSAYVFGGGTKLTVLG | 122 |
| GS017 | Heavy Chain | EVQLLESGGGLVQPGGSLRLSCAASGFTFSGYAMSWVRQAPGKG LEWVSGISPGDGSTYYADSVKGRFTISRDNSKNTLYLQMNSLRA EDTAVYYCARVARMCQGWRCSYADGMDVWGQGTLVTVSS | 123 |
| | Light Chain | QSVLTQPPSASGTPGQRVTISCTGSSSNIGNNSVYWYQQLPGTA PKLLIYSDSHRPSGVPDRFSGSKSGTSASLAISGLRSEDEADYY CGTWDSSLSGYVFGGGTKLTVLG | 124 |
| GS018 | Heavy Chain | EVQLLESGGGLVQPGGSLRLSCAASGLTFSNYAMSWVRQAPGKG LEWVSVISPGSGSKYYADSVKGRFTVSRDNSKNTLYLQMNSLRA EDTAVYYCARHRVIKINRQTYYDYGMDVWGQGTLVTVSS | 125 |
| | Light Chain | QSVLTQPPSASGTPGQRVTISCGSSSNIGSNTVSWYQQLPGTA PKLLIYSDNNRPSGVPDRFSGSKSGTSASLAISGLRSEDEADYY CGAWDDSLSAYVFGGGTKLTVLG | 126 |
| GN328 | Heavy Chain | EVQLVESGGGLVQPGGSLRVSCAASGFTFSTAWMDWVRQAPGKG LEWVANINPDGSEKHYVDSVKGRFTVSRDNAKNSVYLHMNTLRA EDTAVYYCSKALDYWGQGTTVIVSS | 127 |
| | Light Chain | DIQMTQSPSTLSASVGDRVTITCRASQNINTWLAWYQQKPGKAP EVLIYEASSLESGVPPRFSGSGSGTEFTLTISSLQPDDSATYYC QQYNTYSPTFGQGTKLEIKR | 128 |

TABLE 1-continued

| Clone | Variable Region | Amino Acid Sequencce | SEQ ID NO: |
|---|---|---|---|
| GN337 | Heavy Chain | EVQLVESGPGLVKPSQTLSLTCTVSGGSVSSGGYHWNWIRQHPG KGLEWIGYIFNSGNTDYNPSLRSRLTISQDTSKNQFSLKLSSVT AADTAVYYCARHRSALLRWFDYWGQGTMVTVSSASTKGPSVFPL APSSKSTSG | 129 |
| | Light Chain | DVVLTQSPSSLSAFVGDRVTITCQASQDIRKYLNWFQQKPGKAP KLLIYDASTLETGVSSRFSGSGSGTHFNLVISSLEPEDSATYYC QQHDFVPRTFGQGTKLEIKR | 130 |
| GN414 | Heavy Chain | QVQLVQSGAEVKKPGASVKVSCKASGYTFSTYGITWVRQAPGQG LEWMGRITPNNGVTDYAQKFQGRVTMTRDTSISTAYMELSSLRS DDSAVYYCAREIGSSSWKLLDPWGQGTMVTVSS | 131 |
| | Light Chain | QAVLTQPSSVSVSPGQTASITCTGNSNNVGYEGAAWVQQYQGHP PKLLSDRNHNRPSGISERFSASRSGNTASLTITGLQSEDEADYY CSAWDSSLSEWVSGGGTKLTVLG | 132 |

TABLE 2

| Clone | Variable Region | CDR1 | CDR2 | CDR3 |
|---|---|---|---|---|
| GX090 | Heavy Chain | SYGIS (SEQ ID NO: 133) | WISAYNGNTNYAQKLQG (SEQ ID NO: 134) | GSSFSGFDP (SEQ ID NO: 135) |
| | Light Chain | SGSSSNIGKNHVS (SEQ ID NO: 136) | DNHRRPS (SEQ ID NO: 137) | GTWDSSLSA (SEQ ID NO: 138) |
| GX092 | Heavy Chain | SYGIS (SEQ ID NO: 133) | WISAYNGNTNYAQKLQG (SEQ ID NO: 134) | ADWGFFDY (SEQ ID NO: 139) |
| | Light Chain | SGSSSNIGSNTVT (SEQ ID NO: 140) | ANNQRPS (SEQ ID NO: 141) | AAWDDSLNG (SEQ ID NO: 142) |
| GX099 | Heavy Chain | SYYMH (SEQ ID NO: 143) | IINPSGGSTSYAQKFQG (SEQ ID NO: 144) | YSSSPAKIDY (SEQ ID NO: 145) |
| | Light Chain | GSSSNIGKYYVS (SEQ ID NO: 146) | DNNKRPS (SEQ ID NO: 147) | GTWDSSLNA (SEQ ID NO: 148) |
| GX102 | Heavy Chain | GYYMH (SEQ ID NO: 149) | WINPNSGGTNYAQKFQG (SEQ ID NO: 150) | RGLRGDFDY (SEQ ID NO: 151) |
| | Light Chain | SGSSSNIGTNHVF (SEQ ID NO: 152) | RNNIRPS (SEQ ID NO: 153) | AAWDDSLS (SEQ ID NO: 154) |
| GX107 | Heavy Chain | SYYMH (SEQ ID NO: 143) | IINPSGGSTSYAQKFQG (SEQ ID NO: 144) | SHGDYPEDY (SEQ ID NO: 155) |
| | Light Chain | SGDALPKHYAY (SEQ ID NO: 156) | EDKKRPA (SEQ ID NO: 157) | YSTDTSGNH (SEQ ID NO: 158) |
| GX114 | Heavy Chain | DYYMS (SEQ ID NO: 159) | YISSSGSTIYYADSVKG (SEQ ID NO: 160) | VVDSSDY (SEQ ID NO: 161) |

TABLE 2-continued

| Clone | Variable Region | CDR1 | CDR2 | CDR3 |
|---|---|---|---|---|
| | Light Chain | QASQDISNYLN (SEQ ID NO: 162) | DASNLET (SEQ ID NO: 163) | QQYDNLP (SEQ ID NO: 164) |
| GX116 | Heavy Chain | SYYMH (SEQ ID NO: 143) | IINPSGGSTSYAQKFQG (SEQ ID NO: 144) | VMVRGVSTFGY (SEQ ID NO: 165) |
| | Light Chain | SGSSSNIGKNFLS (SEQ ID NO: 166) | RNNRRPS (SEQ ID NO: 167) | GAWDSRLSG (SEQ ID NO: 168) |
| GX118 | Heavy Chain | SSSYYWG (SEQ ID NO: 169) | SIYYSGSTYYNPSLES (SEQ ID NO: 170) | LRSFADNYV (SEQ ID NO: 171) |
| | Light Chain | SGSSSNIGNNFVS (SEQ ID NO: 172) | DNNERPS (SEQ ID NO: 147) | GTWDNSLGT (SEQ ID NO: 173) |
| GX119 | Heavy Chain | SYGMH (SEQ ID NO: 174) | VIWYDGSNKYYADSVKG (SEQ ID NO: 175) | DRSWNYYGMDV (SEQ ID NO: 176) |
| | Light Chain | RASQSISSYLN (SEQ ID NO: 177) | AASSLQS (SEQ ID NO: 178) | QQSYSTP (SEQ ID NO: 179) |
| GX122 | Heavy Chain | SYYMH (SEQ ID NO: 143) | IINPSGGSTSYAQKFQG (SEQ ID NO: 144) | DGGSSPDI (SEQ ID NO: 180) |
| | Light Chain | SGDALPKKYAY (SEQ ID NO: 181) | EDKKRPSEI (SEQ ID NO: 182) | YSIDRSGSR (SEQ ID NO: 183) |
| GX184 | Heavy Chain | SSNNYWG (SEQ ID NO: 184) | SIFYSGSTYYNPSLKS (SEQ ID NO: 185) | LPTGTPGFYFDY (SEQ ID NO: 186) |
| | Light Chain | TGNSNNVGNQGAA (SEQ ID NO: 187) | RNNNEPS (SEQ ID NO: 392) | SAWDSSLSA (SEQ ID NO: 188) |
| GX186 | Heavy Chain | DYYMS (SEQ ID NO: 159) | YISSSGSTIYYADSVKG (SEQ ID NO: 160) | LQGY (SEQ ID NO: 189) |
| | Light Chain | KSSQSVLYSSNNKNYLA (SEQ ID NO: 190) | WASTRES (SEQ ID NO: 191) | QQYYSTP (SEQ ID NO: 192) |
| GX189 | Heavy Chain | SSNNYWG (SEQ ID NO: 184) | SIFYSGSTYYNPSLKS (SEQ ID NO: 185) | LPTGTPGFYFDY (SEQ ID NO: 186) |
| | Light Chain | TGNSSNVGNQGAA (SEQ ID NO: 193) | RNNRPS (SEQ ID NO: 392) | SAWDSSLSA (SEQ ID NO: 188) |
| GX196 | Heavy Chain | DYYMS (SEQ ID NO: 159) | YISSSGSTIYYADSVKG (SEQ ID NO: 160) | VTGDY (SEQ ID NO: 194) |
| | Light Chain | KSSQSVLYSSNNKNYLA (SEQ ID NO: 190) | WASTRES (SEQ ID NO: 191) | QQYYSTP (SEQ ID NO: 192) |

TABLE 2-continued

| Clone | Variable Region | CDR1 | CDR2 | CDR3 |
|---|---|---|---|---|
| GX197 | Heavy Chain | SYGIS (SEQ ID NO: 133) | WISAYNGNTNYAQKLQG (SEQ ID NO: 134) | QGSGWLDY (SEQ ID NO: 195) |
| | Light Chain | TGSGGNIASNYVQ (SEQ ID NO: 196) | DDVQRPS (SEQ ID NO: 197) | QSYDRTYR (SEQ ID NO: 198) |
| GX201 | Heavy Chain | NYGMN (SEQ ID NO: 199) | SISTRSGYIFYADSVKG (SEQ ID NO: 200) | DRPNRSGMDV (SEQ ID NO: 201) |
| | Light Chain | TGTSSDVGGYNYVS (SEQ ID NO: 202) | DVSNRPS (SEQ ID NO: 203) | SSYTSSDT (SEQ ID NO: 204) |
| GX205 | Heavy Chain | DYYMS (SEQ ID NO: 159) | YISSSGSTIYYADSVKG (SEQ ID NO: 160) | VLLDY (SEQ ID NO: 205) |
| | Light Chain | QASQDISNYLN (SEQ ID NO: 162) | DASNLET (SEQ ID NO: 163) | QQYDNLLA (SEQ ID NO: 206) |
| GX206 | Heavy Chain | SSSYYWG (SEQ ID NO: 169) | SIYYSGSTYYNPSLKS (SEQ ID NO: 170) | LGDYGGNGYYFDY (SEQ ID NO: 207) |
| | Light Chain | SGSSSNIGKNGVS (SEQ ID NO: 208) | ENNRRPS (SEQ ID NO: 209) | GTWDSSLNA (SEQ ID NO: 148) |
| GX207 | Heavy Chain | SYGIS (SEQ ID NO: 133) | WISAYNGNTNYAQKLQG (SEQ ID NO: 134) | EGIAAAGYYYGMDV (SEQ ID NO: 210) |
| | Light Chain | TGTSSDVGGYNRVS (SEQ ID NO: 211) | EVSNRPS (SEQ ID NO: 212) | SSYTSSTTY (SEQ ID NO: 213) |
| GX209 | Heavy Chain | SYYMH (SEQ ID NO: 143) | IINPSGGSTSYAQKFQG (SEQ ID NO: 144) | GYYYGMDV (SEQ ID NO: 214) |
| | Light Chain | SGDKLGDKYVF (SEQ ID NO: 215) | QDNKRPS (SEQ ID NO: 216) | QTWDSST (SEQ ID NO: 217) |
| GX213 | Heavy Chain | SSSYYWG (SEQ ID NO: 169) | SIYYSGSTYYNPSLKS (SEQ ID NO: 170) | LFWQQLTFDY (SEQ ID NO: 218) |
| | Light Chain | SGSSSNIGKNHVI (SEQ ID NO: 219) | ENNKRPS (SEQ ID NO: 220) | GTWDNSLSA (SEQ ID NO: 221) |
| GX214 | Heavy Chain | DYYMS (SEQ ID NO: 159) | YISSSGSTIYYADSVKG (SEQ ID NO: 160) | LYDF (SEQ ID NO: 222) |
| | Light Chain | QASQDITNFLN (SEQ ID NO: 223) | DASNLET (SEQ ID NO: 163) | QQYDNLP (SEQ ID NO: 164) |
| GX216 | Heavy Chain | DYYMS (SEQ ID NO: 159) | YISSSGSTIYYADSVKG (SEQ ID NO: 160) | VVDSSDY (SEQ ID NO: 161) |

TABLE 2-continued

| Clone | Variable Region | CDR1 | CDR2 | CDR3 |
|---|---|---|---|---|
| | Light Chain | RASQSVSSYLA (SEQ ID NO: 224) | DASNRAT (SEQ ID NO: 225) | QQRSNWPPVA (SEQ ID NO: 226) |
| GX217 | Heavy Chain | DYYMS (SEQ ID NO: 159) | YISSSGSTIYYADSVKG (SEQ ID NO: 160) | VSGDPKD (SEQ ID NO: 227) |
| | Light Chain | RASQSVSSNLA (SEQ ID NO: 228) | GASTRAT (SEQ ID NO: 229) | QQYNNWPR (SEQ ID NO: 230) |
| GX219 | Heavy Chain | GYYMH (SEQ ID NO: 149) | RINPNSGGTNYAQKFQG (SEQ ID NO: 231) | VARYCSSTSCRTGGMDV (SEQ ID NO: 232) |
| | Light Chain | SGRSSNIGSRYVY (SEQ ID NO: 233) | RNDQRPS (SEQ ID NO: 234) | ATWDDSLSA (SEQ ID NO: 235) |
| GX221 | Heavy Chain | SSNNYWG (SEQ ID NO: 184) | SIFYSGSTYYNPSLKS (SEQ ID NO: 185) | LPTGTPGFYFDY (SEQ ID NO: 186) |
| | Light Chain | TGNSSNVGNQGAA (SEQ ID NO: 193) | RNNKRPS (SEQ ID NO: 236) | SAWDSSLSA (SEQ ID NO: 188) |
| GX222 | Heavy Chain | DYYMS (SEQ ID NO: 159) | YISSSGSTIYYADSVKG (SEQ ID NO: 160) | VTLDY (SEQ ID NO: 237) |
| | Light Chain | QASQDISNYLN (SEQ ID NO: 162) | DASNLET (SEQ ID NO: 163) | QQYDSLP (SEQ ID NO: 238) |
| GX224 | Heavy Chain | SYYMH (SEQ ID NO: 143) | IINPSGGSTSYAQKFQG (SEQ ID NO: 144) | SRPRSSSFDY (SEQ ID NO: 239) |
| | Light Chain | TVSSGSTAKNYVH (SEQ ID NO: 240) | EDNRRPS (SEQ ID NO: 241) | QSYDDSGDR (SEQ ID NO: 242) |
| GX225 | Heavy Chain | SYYMH (SEQ ID NO: 143) | IINPSGGSTSYAQKFQG (SEQ ID NO: 144) | ESGPSGGMDV (SEQ ID NO: 243) |
| | Light Chain | SGDALPKQYAY (SEQ ID NO: 244) | KDSERPS (SEQ ID NO: 245) | SSYTSSSTR (SEQ ID NO: 246) |
| GX226 | Heavy Chain | DYYMS (SEQ ID NO: 159) | YISSSGSTIYYADSVKG (SEQ ID NO: 160) | VTLDY (SEQ ID NO: 237) |
| | Light Chain | QASQDISNYLN (SEQ ID NO: 162) | DASNLET (SEQ ID NO: 163) | QQYDNLP (SEQ ID NO: 164) |
| GX229 | Heavy Chain | DYYMS (SEQ ID NO: 159) | YISSSGSTIYYADSVKG (SEQ ID NO: 160) | VLLDY (SEQ ID NO: 247) |
| | Light Chain | QASQDISNYLN (SEQ ID NO: 162) | DASNLET (SEQ ID NO: 163) | QQYDNLW (SEQ ID NO: 248) |

TABLE 2-continued

| Clone | Variable Region | CDR1 | CDR2 | CDR3 |
|---|---|---|---|---|
| GX233 | Heavy Chain | DYYMS (SEQ ID NO: 159) | YISSSGSTIYYADSVKG (SEQ ID NO: 160) | VVDSSDY (SEQ ID NO: 161) |
|  | Light Chain | QASQDISNYLN (SEQ ID NO: 162) | DASNLET (SEQ ID NO: 163) | MEVRYWP (SEQ ID NO: 249) |
| GX234 | Heavy Chain | SYGIS (SEQ ID NO: 133) | WISAYNGNTNYAQKLQG (SEQ ID NO: 134) | VGLGDFWSGDYYYYYGMDV (SEQ ID NO: 250) |
|  | Light Chain | QGDSLRSSYAS (SEQ ID NO: 251) | GKNNRPS (SEQ ID NO: 252) | HSRDSTGSHPN (SEQ ID NO: 253) |
| GX235 | Heavy Chain | DYYMS (SEQ ID NO: 159) | YISSSGSTIYYADSVKG (SEQ ID NO: 160) | VSGDPKD (SEQ ID NO: 227) |
|  | Light Chain | KSSQSVLYSSNNENYLA (SEQ ID NO: 190) | WASTRES (SEQ ID NO: 191) | QQYYSTP (SEQ ID NO: 192) |
| GX242 | Heavy Chain | DYYMS (SEQ ID NO: 159) | YISSSGSTIYYADSVKG (SEQ ID NO: 160) | VVAAREDY (SEQ ID NO: 254) |
|  | Light Chain | RATQSVGSYLA (SEQ ID NO: 255) | DAFNRAT (SEQ ID NO: 256) | QQRSNWP (SEQ ID NO: 257) |
| GX245 | Heavy Chain | DYYMS (SEQ ID NO: 159) | YISSSGSTIYYADSVKG (SEQ ID NO: 160) | VSDDSPY (SEQ ID NO: 258) |
|  | Light Chain | QASQDISNYLN (SEQ ID NO: 162) | DASNLET (SEQ ID NO: 163) | QQYDNLLA (SEQ ID NO: 206) |
| GX247 | Heavy Chain | SYYMH (SEQ ID NO: 143) | IINPSGGSTSYAQKFQG (SEQ ID NO: 144) | TRKGSGYSYGYGMDV (SEQ ID NO: 259) |
|  | Light Chain | SGDKLGNKYVS (SEQ ID NO: 260) | QDNKRPS (SEQ ID NO: 216) | QTWDSS (SEQ ID NO: 261) |
| GX248 | Heavy Chain | SYAIS (SEQ ID NO: 262) | GIIPIFGTANYAQKFQG (SEQ ID NO: 263) | VRGTGPRGGTFDY (SEQ ID NO: 264) |
|  | Light Chain | SGSSSNIGNNYVS (SEQ ID NO: 265) | DNNKRPS (SEQ ID NO: 147) | GTWDSSLSA (SEQ ID NO: 138) |
| GX253 | Heavy Chain | DYYMS (SEQ ID NO: 159) | YISSSGTTIYYADSVKG (SEQ ID NO: 266) | VRDSSGF (SEQ ID NO: 267) |
|  | Light Chain | SGSSSNIGNNYVS (SEQ ID NO: 265) | DNNKRPS (SEQ ID NO: 147) | GTWDSSLSA (SEQ ID NO: 138) |
| GX259 | Heavy Chain | NYWI (SEQ ID NO: 268) | IIYPGDSDTRYSPSLQG (SEQ ID NO: 269) | IGLREGR (SEQ ID NO: 270) |

TABLE 2-continued

| Clone | Variable Region | CDR1 | CDR2 | CDR3 |
|---|---|---|---|---|
| | Light Chain | RASQGISNYLA (SEQ ID NO: 271) | DASNLET (SEQ ID NO: 163) | QQYDN (SEQ ID NO: 272) |
| GX263 | Heavy Chain | SYSMN (SEQ ID NO: 273) | SISSSSSYIYYADSVKG (SEQ ID NO: 274) | VTPYYYYGMDV (SEQ ID NO: 275) |
| | Light Chain | SGSSSNIGNNYVS (SEQ ID NO: 265) | DSNKRPP (SEQ ID NO: 276) | GAWDSSLSA (SEQ ID NO: 277) |
| GX264 | Heavy Chain | SSSYYWG (SEQ ID NO: 169) | SIYYSGSTYYNPSLKS (SEQ ID NO: 170) | LRWYSYGYFDVRGGYYFDY (SEQ ID NO: 278) |
| | Light Chain | SGSSSNIGKNGVS (SEQ ID NO: 208) | ENNRRPS (SEQ ID NO: 209) | GTWDSSLNA (SEQ ID NO: 148) |
| GX265 | Heavy Chain | DYYMS (SEQ ID NO: 159) | YISSSGSTIYYADSVKG (SEQ ID NO: 160) | VHLDY (SEQ ID NO: 279) |
| | Light Chain | KSSQSVLYSSNNKNYLA (SEQ ID NO: 190) | WASTRES (SEQ ID NO: 191) | QQYYSTP (SEQ ID NO: 192) |
| GX268 | Heavy Chain | SYGMH (SEQ ID NO: 174) | VIWYDGSNKYYADSVKG (SEQ ID NO: 175) | DRSWNYYGMDV (SEQ ID NO: 176) |
| | Light Chain | RASQSISSYLN (SEQ ID NO: 177) | AASSLQS (SEQ ID NO: 178) | QQSYST (SEQ ID NO: 280) |
| GX270 | Heavy Chain | SSYMH (SEQ ID NO: 281) | IINPNSRGTNYAQKFQG (SEQ ID NO: 282) | SSGDYPDY (SEQ ID NO: 283) |
| | Light Chain | SGDALPKHYAY (SEQ ID NO: 156) | YEDKKRPA (SEQ ID NO: 284) | YSTDTSGNH (SEQ ID NO: 158) |
| GS001 | Heavy Chain | SYSMS (SEQ ID NO: 285) | GISPSGGNKYYADSVKG (SEQ ID NO: 286) | ALLGCKSAYCYYAMDV (SEQ ID NO: 287) |
| | Light Chain | TGSSSNIGSNAVN (SEQ ID NO: 288) | ADSKRPS (SEQ ID NO: 289) | GSWDSSLSG (SEQ ID NO: 290) |
| GS002 | Heavy Chain | GYSMS (SEQ ID NO: 291) | SISPGGSSTYYADSVKG (SEQ ID NO: 292) | YRVWHMTTGDYYSNAMDV (SEQ ID NO: 293) |
| | Light Chain | TGSSSNIGSNAVS (SEQ ID NO: 294) | DDNKRPS (SEQ ID NO: 295) | GTWDDSLSG (SEQ ID NO: 296) |
| GS003 | Heavy Chain | NYSMS (SEQ ID NO: 297) | VISPGSGSTYYADSVKG (SEQ ID NO: 298) | YRVMRSPHNPYYSYGMDV (SEQ ID NO: 299) |
| | Light Chain | SGSSSNIGSNDVN (SEQ ID NO: 300) | SNSQRPS (SEQ ID NO: 301) | GSWDASLSG (SEQ ID NO: 302) |

TABLE 2-continued

| Clone | Variable Region | CDR1 | CDR2 | CDR3 |
|---|---|---|---|---|
| GS004 | Heavy Chain | NYSMS (SEQ ID NO: 297) | AISPGSSNKYYADSVKG (SEQ ID NO: 303) | YRVWAHSASSSYSNAMDV (SEQ ID NO: 304) |
| | Light Chain | SGSSSNIGNNDVS (SEQ ID NO: 305) | SDSQRPS (SEQ ID NO: 306) | GSWDDSLNG (SEQ ID NO: 307) |
| GS005 | Heavy Chain | NYAMS (SEQ ID NO: 308) | VISPDSSSKYYADSVKG (SEQ ID NO: 309) | AAVRRYGPSPYYYYAMDV (SEQ ID NO: 310) |
| | Light Chain | TGSSSNIGNNYVS (SEQ ID NO: 311) | ADSHRPS (SEQ ID NO: 312) | ATWDYSLSG (SEQ ID NO: 313) |
| GS006 | Heavy Chain | GYSMS (SEQ ID NO: 291) | AISPGGGSKYYADSVRG (SEQ ID NO: 314) | YRVQKSAKNVYSSNGMDV (SEQ ID NO: 315) |
| | Light Chain | SGSSSNIGNNAVN (SEQ ID NO: 316) | YDSNRPS (SEQ ID NO: 317) | GAWDSSLSA (SEQ ID NO: 277) |
| GS007 | Heavy Chain | NYSMS (SEQ ID NO: 297) | VISHDGRSKYYADSVKG (SEQ ID NO: 318) | FRVWKRTNAHSYANAMDV (SEQ ID NO: 319) |
| | Light Chain | TGSSSNIGSNSVS (SEQ ID NO: 320) | ANSNRPS (SEQ ID NO: 321) | GTWDASLSA (SEQ ID NO: 322) |
| GS008 | Heavy Chain | NYAMS (SEQ ID NO: 308) | VISPDNGSTYYADSVKG (SEQ ID NO: 323) | ARVHCRRDQCYSYGMDV (SEQ ID NO: 324) |
| | Light Chain | TGSSSNIGSNNVT (SEQ ID NO: 325) | ANSQRPS (SEQ ID NO: 326) | GAWDSSLNG (SEQ ID NO: 327) |
| GS009 | Heavy Chain | NYSMS (SEQ ID NO: 297) | VISPSGGNTYYADSVKG (SEQ ID NO: 328) | YRVKQMLNQRSYSNAMDV (SEQ ID NO: 329) |
| | Light Chain | TGSSSNIGNNYVS (SEQ ID NO: 311) | DDSQRPS (SEQ ID NO: 330) | GSWDASLSG (SEQ ID NO: 302) |
| GS010 | Heavy Chain | NYSMS (SEQ ID NO: 297) | VISPSSGSIYYADSVKG (SEQ ID NO: 331) | YRVRQLKHTRSYADAMDV (SEQ ID NO: 332) |
| | Light Chain | SGSSSNIGSNAVS (SEQ ID NO: 333) | ANSHRPS (SEQ ID NO: 334) | ASWDSSLSG (SEQ ID NO: 335) |
| GS011 | Heavy Chain | NYAMS (SEQ ID NO: 308) | GISPGGSSIYYADSVKG (SEQ ID NO: 336) | YAVYFLRSHGSYDYGMDV (SEQ ID NO: 337) |
| | Light Chain | TGSSSNIGSNDVT (SEQ ID NO: 338) | SNNQRPS (SEQ ID NO: 339) | GAWDYSLNA (SEQ ID NO: 340) |
| GS012 | Heavy Chain | NYSMS (SEQ ID NO: 297) | GISPGSGSKYYADSVRG (SEQ ID NO: 341) | RARRFDY (SEQ ID NO: 342) |

TABLE 2-continued

| Clone | Variable Region | CDR1 | CDR2 | CDR3 |
|---|---|---|---|---|
| | Light Chain | TGSSSNIGNNAVT (SEQ ID NO: 343) | SNSQRPS (SEQ ID NO: 301) | GSWDSSLNG (SEQ ID NO: 344) |
| GS013 | Heavy Chain | NYAMS (SEQ ID NO: 308) | SISSGGGSTYYADSVKG (SEQ ID NO: 345) | KKSQFDY (SEQ ID NO: 346) |
| | Light Chain | SGSSSNIGSNTVN (SEQ ID NO: 347) | ANSQRPS (SEQ ID NO: 326) | DTWDYSLSG (SEQ ID NO: 348) |
| GS014 | Heavy Chain | NYAMS (SEQ ID NO: 308) | VISPNSGSNTYYADSVKG (SEQ ID NO: 349) | PRILRRRVDHSYSYAMDV (SEQ ID NO: 350) |
| | Light Chain | TGSSSNIGNNYVS (SEQ ID NO: 311) | SNSHRPS (SEQ ID NO: 351) | GTWDYSLSG (SEQ ID NO: 352) |
| GS015 | Heavy Chain | DYSMS (SEQ ID NO: 353) | AISPDGGSKYYADSVKGR (SEQ ID NO: 354) | FRVIKLRAGWYSANGMDV (SEQ ID NO: 355) |
| | Light Chain | SGSSSNIGNNDVS (SEQ ID NO: 356) | YNSKRPS (SEQ ID NO: 357) | GAWDDSLNG (SEQ ID NO: 358) |
| GS016 | Heavy Chain | NYAMS (SEQ ID NO: 308) | GIYSGNGNTYYADSVKG (SEQ ID NO: 359) | ALSSCPRGPCYYDDGMDV (SEQ ID NO: 360) |
| | Light Chain | SGSSSNIGSNDVT (SEQ ID NO: 361) | DNSKRPS (SEQ ID NO: 362) | GTWDASLSA (SEQ ID NO: 322) |
| GS017 | Heavy Chain | GYAM (SEQ ID NO: 363) | GISPGDGSTYYADSVKG (SEQ ID NO: 364) | VARMCQGWRCSYADGMDV (SEQ ID NO: 365) |
| | Light Chain | TGSSSNIGNNSVY (SEQ ID NO: 366) | SDSHRPS (SEQ ID NO: 367) | GTWDSSLSG (SEQ ID NO: 368) |
| GS018 | Heavy Chain | NYAMS (SEQ ID NO: 308) | VISPGSGSKYYADSVKG (SEQ ID NO: 369) | HRVIKINRQTYYDYGMDV (SEQ ID NO: 370) |
| | Light Chain | SGSSSNIGSNTVS (SEQ ID NO: 371) | SDNNRPS (SEQ ID NO: 372) | GAWDDSLSA (SEQ ID NO: 373) |
| GN328 | Heavy Chain | TAWMD (SEQ ID NO: 374) | NINPDGSEKHYVDSVKG (SEQ ID NO: 375) | ALDY (SEQ ID NO: 376) |
| | Light Chain | RASQNINTWLA (SEQ ID NO: 377) | EASSLES (SEQ ID NO: 378) | QQYNTYS (SEQ ID NO: 379) |
| GN337 | Heavy Chain | SGGYHWN (SEQ ID NO: 380) | YIFNSGNTDYNPSL (SEQ ID NO: 381) | HRSRLLRWFDY (SEQ ID NO: 382) |
| | Light Chain | QASQDIRKYLN (SEQ ID NO: 383) | DASTLET (SEQ ID NO: 384) | QQHDFVP (SEQ ID NO: 385) |

TABLE 2-continued

| Clone | Variable Region | CDR1 | CDR2 | CDR3 |
|---|---|---|---|---|
| GN414 | Heavy Chain | TYGIT (SEQ ID NO: 386) | RITPNNGVTDYAQKFQG (SEQ ID NO: 387) | EIGSSSWKLLDP (SEQ ID NO: 388) |
| | Light Chain | TGNSNNVGYEGAA (SEQ ID NO: 389) | SDRNHNRPS (SEQ ID NO: 390) | SAWDSSLSE (SEQ ID NO: 391) |

1-3: Measurement of Quantitative Binding Capacity of Anti-GPC3 Antibody to Antigen Quantitative binding capacity (affinity) of GX102 and GX270 clone antibodies, purified anti-GPC3 antibodies, to recombinant human GPC 3 was measured using a Biacore T-200(GE Healthcare, U.S.) biosensor. After immobilizing GPC3 (Cat. No. 2119-GP-050, R&D systems) purified from HEK293 cells onto a CM5 chip (GE Healthcare) to an Rmax of 200 using an amine-carboxyl reaction, the GX102 or GX270 antibody sequentially diluted in a HBS-EP buffer solution (10 mM HEPES, pH7.4, 150 mM NaCl, 3 mM EDTA, 0.005% surfactant P20) was flowed at a flow rate of 30 μL/min in a concentration range of 0.078 nM to 5 nM for an association time of 120 seconds and a dissociation time of 1800 seconds. Dissociation of the antibody bound to GPC3 was induced by flowing 10 mM Glycine-HCl (pH1.5) at a flow rate of 30 μL/min for 30 seconds (Table 3). Affinity was obtained as kinetic rate constants ($K_{on}$ and $K_{off}$) and an equivalent dissociation constant ($K_D$) using a Biacore T-200 evaluation software (Table 4).

TABLE 3

| SPR | Biacore T200 |
|---|---|
| Chip | CM5 |
| Running Buffer | HBS-EP pH 7.4 |
| Flow rate | 30 μl/Min |
| Association/Dissociation time | 120 Sec/600 Sec |
| IgG Conc. | 0.078~5 nM, ½ serial dilution |
| Regeneration | 10 mM Glycine-HCl pH 1.5, 30 Sec |

TABLE 4

| | $K_{on}$ | $K_{off}$ | $K_D$ |
|---|---|---|---|
| GX102 | $9.1 \times 10^6$ | $8.4 \times 10^{-5}$ | $9.2 \times 10^{-12}$ |
| GX270 | $2.4 \times 10^6$ | $1.7 \times 10^{-4}$ | $7.0 \times 10^{-11}$ |

Example 2: Fluorescence Activated Cell Sorter (FACS) Analysis on Binding of Anti-Glypican 3 Antibody to Cancer Cell Expressing GPC3

In order to evaluate whether the anti-GPC3 antibody derived from the synthetic library was selectively bound to cells expressing GPC3, an expression amount of GPC3 was measured in a cancer cell line, and binding of the antibody was confirmed using a FACS experiment. Table 5 illustrates antibody clones used for FACS screening for cancer cells expressing GPC3.

TABLE 5

| Source | Number | Clones |
|---|---|---|
| Synthetic Library | 41 | GS001, GS018, GN328, GN337, GN414, GX090, GX092, GX099, GX102, GX107, GX118, GX119, GX122, GX184, GX206, GX207, GX209, GX225, GX234, GX247, GX248, GX253, GX263, GX268, GX270 |

2-1: Preparation of Cell Line Expressing GPC3

Figure 1:
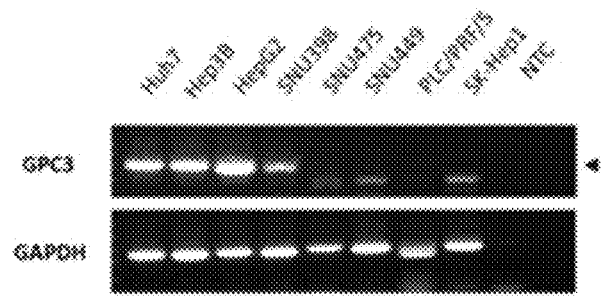
FIG. 1 is a view illustrating a result of confirming expression of GPC3 and glyceraldehyde 3-phosphate dehydrogenase (GAPDH) in each cell line.

An expression amount of GPC3 mRNA in cells was confirmed in 8 kinds of hepatic cancer cell lines (Huh-7, HepG2, Hep3B, SNU398, SNU475, SNU449, PLC/PRF/5, and SK-Hep1) using a real time-polymerase chain reaction (RT-PCR) method. After a TrypLE Express solution was added to the cell lines cultured in a 6-well plate to detach the cell lines, a total RNA was collected using a trizol solution. In order to amplify the GPC3 mRNA, a forward primer (5' GGA CTT GGC CAC GTT CAT G 3') and a reverse primer (5' ACC TCA GCC ACA GTC AAC GG 3') were used. As a comparison reference for quantitative comparison, a primer set (5' CTT CGC TCT CTG CTC CTC CT 3', 5' CCA GTG GAC TCC ACG ACG TA 3') for a GAPDH mRNA was used. After the total RNA obtained by separation using the trizol solution was quantified using an OD quantification method, 100 ng of cell RNA and 0.5 pM primer were put into a Maxim RT-PCR premix tube and a total volume was set to 20 μL using a nuclease-free distilled water, and a reaction was carried out at 45° C. for 30 minutes. Immediately, after an inactivation process was performed at 94° C. for 5 minutes, a polymerase chain reaction (PCR) was performed for 30 cycles of 94° C. for 30 seconds, 55° C. for 30 seconds, and 72° C. for 1 minute. In order to complete an unreacted reaction after the last cycle, the resultant was additionally kept at 72° C. for 3 minutes, and then, 5 μL of a 5-fold concentrated agarose electrophoresis sample buffer (1.25 mg/mL Bromophenol Blue, 1.25 mg/mL xylene cyanol, 30% glycerol, 25 mM Tris, pH7.6) was added thereto. After each of the analysis samples was put on 1.5% agarose gel and subjected to electrophoresis at 100 volts for 15 minutes, GPC3 and GPADH DNA fragments amplified by RT-PCR were examined at a UV wavelength (FIG. 1).

Sequences of primers used for amplification of cDNA (amplicon size 758 bp) encoding GPC3 were as follows.

```
Forward primer (sense primer):
5'GGA CTT GGC CAC GTT CAT G 3'

Reverse primer (anti-sense primer):
5'AAC TCA GCC ACA GTC AAC GG 3'
```

In addition, sequences of primers used for amplification of cDNA (amplicon size 379 bp) encoding GAPDH were as follows.

```
Forward primer (sense primer):
5'CTT CGC TCT CTG CTC CTC CT 3'

Reverse primer (anti-sense primer):
5'CCA GTG GAC TCC ACG ACG TA 3'
```

Figure 2:
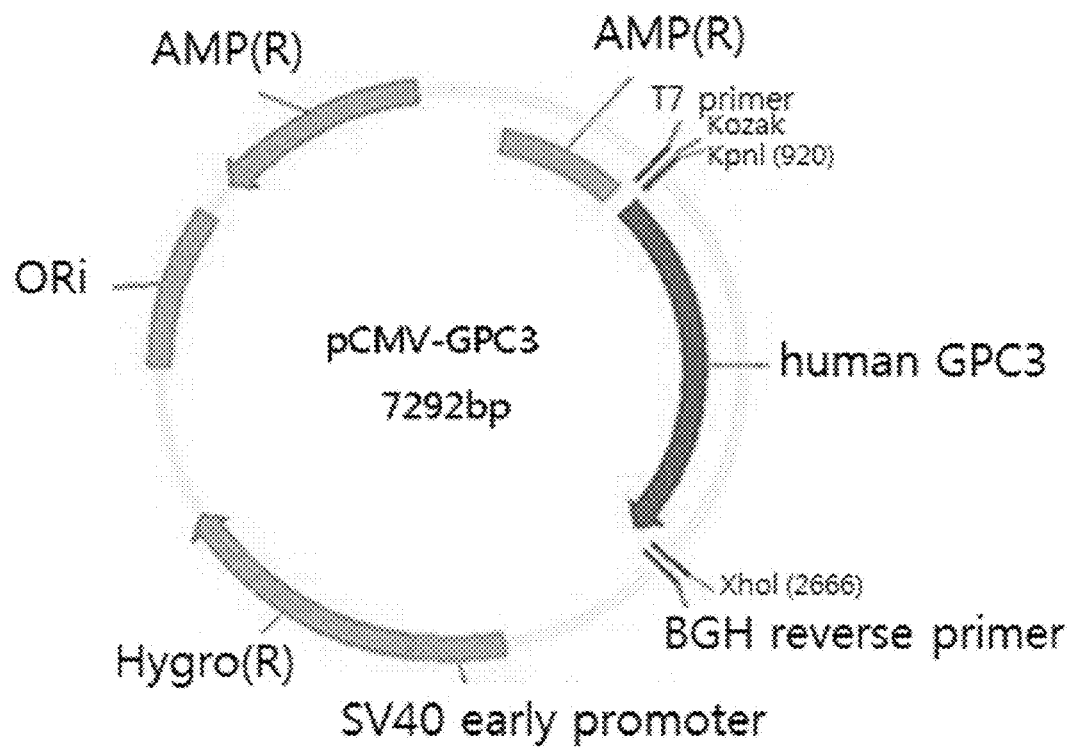
FIG. 2 is a view illustrating a structure of a plasmid used for expression of GPC3 in each cell line.
Figure 3:
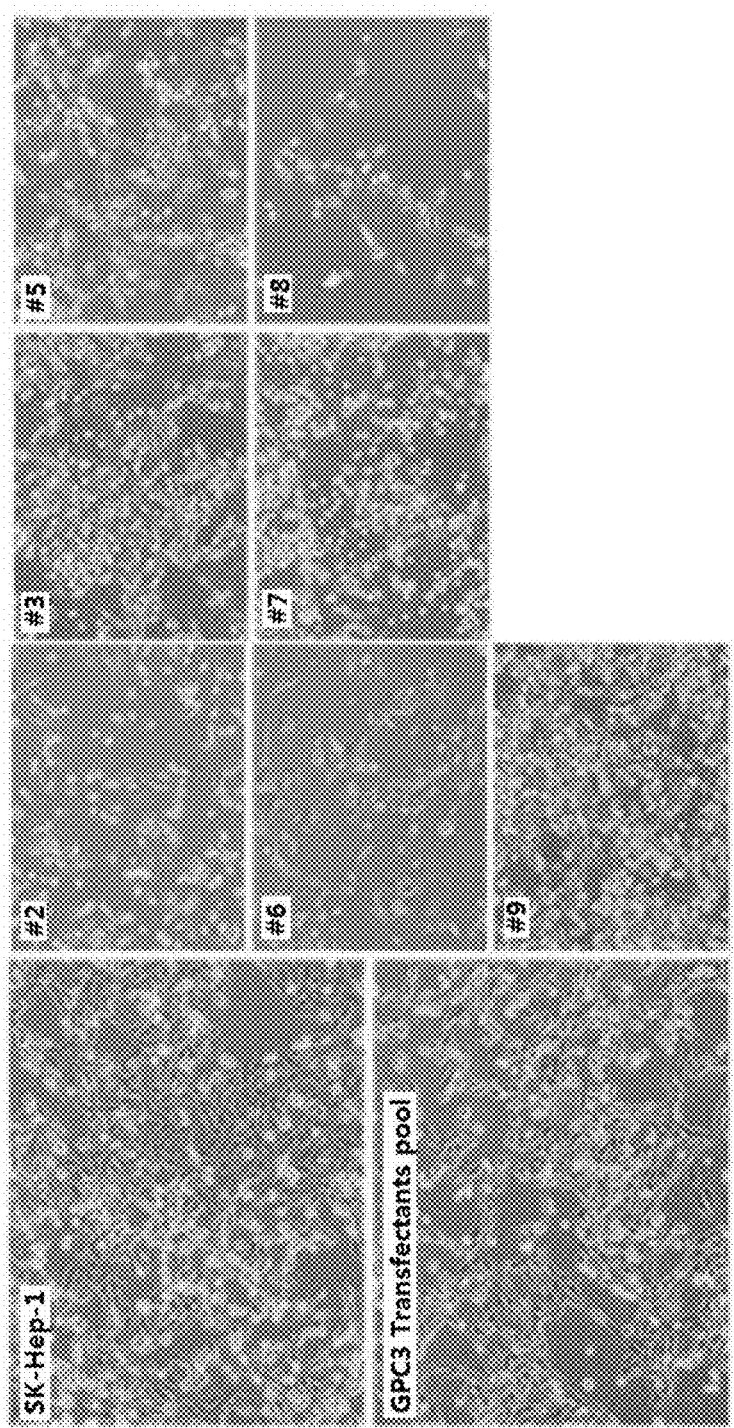
FIG. 3 is a view illustrating that a cell line colony transformed so as to express GPC3 using resistance against Hygromycin may be confirmed.

In SK-Hep1 hepatic cancer cells confirmed as a GPC3 negative cell line, a plasmid (pCMV/GPC3) having a GPC3 expression unit and Hygromycin resistant gene was delivered into cells using a jet-polyethyleneimine (PEI) transfection system (Polyplus, 101-40) (FIG. 2). After 48 hours, the cell culture solution was replaced with a culture medium containing Hygromycin B (200 µg/mL). While the culture medium was replaced every 3 days, 7 kinds of colonies having resistance against Hygromycin were obtained (FIG. 3).

2-2: Analysis of Expression Amount of GPC3 in Cell Line Expressing GPC3 and Tumor Cell Line GPC3 existing on surfaces of cells was measured with respect to a cell line (SK-Hep1-GPC3) in which GPC3 was artificially expressed using a FACS experiment. After detaching cells to be analyzed, cultured in a culture dish by adding a TrypLE Express solution thereto, the detached cells were put into a 50 mL tube and centrifuged at room temperature and 2000 rpm for 3 minutes to remove a culture medium, followed by washing with PBS once. The resultant was suspended using a FACS buffer, transferred to a round bottom tube, and centrifuged at room temperature and 2000 rpm for 3 minutes. A supernatant was removed, and the resultant was suitably dissolved using the FACS buffer so as to have a concentration of 4×105 ea/mL. Then, as a FACS analysis antibody for GPC3, a mouse anti-GPC3 antibody (R&D systems) was used at 4° C., and as an isotope control group, a mouse IgG (1 µg, R&D systems) was used. After 1 hour, the resultant was washed with the FACS buffer two times, the anti-mouse IgG antibody and PE conjugated were added thereto at an amount of 5 µL per sample and bound thereto at 4° C. for 30 minutes. After collecting cells by centrifugation at 2000 rpm for 3 minutes, the cells were re-suspended by adding a fixation buffer (500 µL), and measured using a FACS calibur (FIG. 4).

Figure 4:
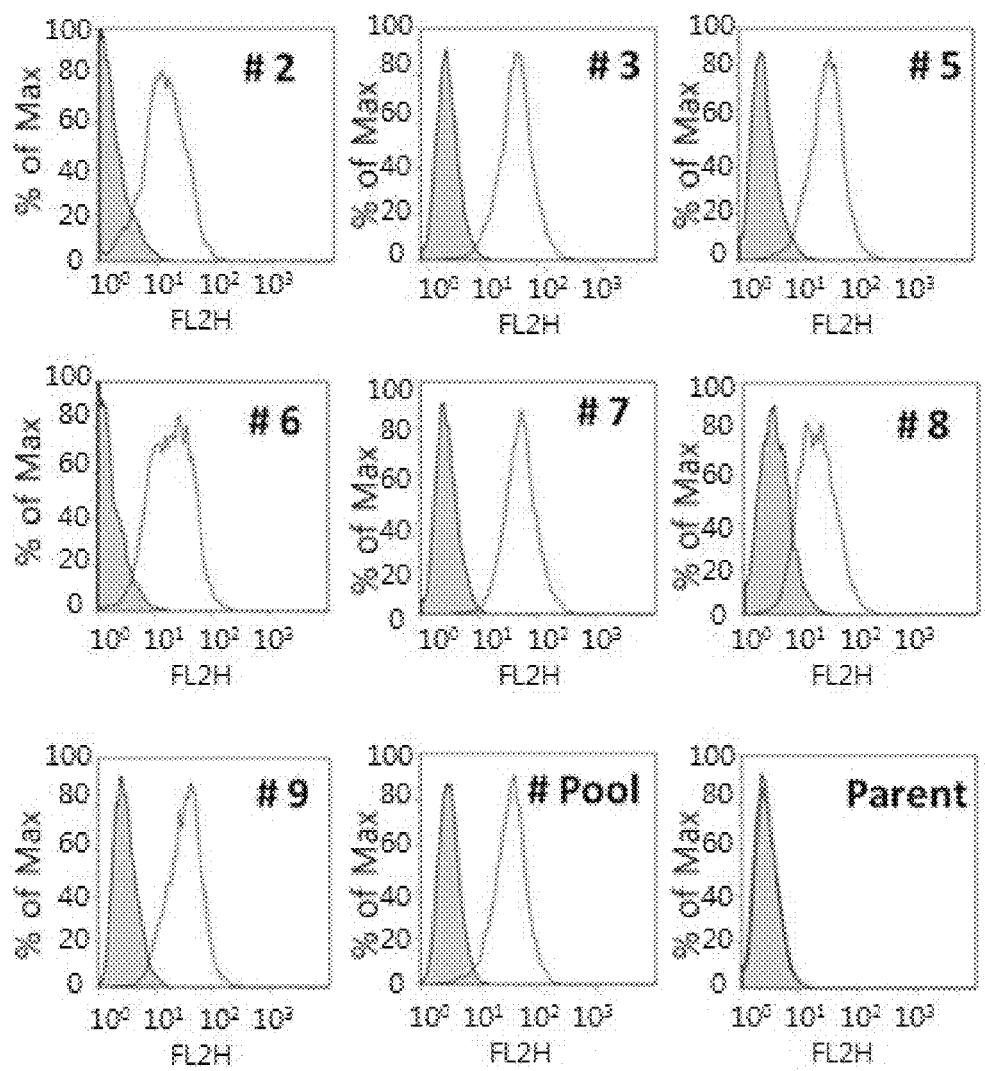
FIG. 4 is a view illustrating a result of analyzing an expression amount of GPC3 in each cell line.

As a result, it was confirmed that GPC3 was positive in 8 kinds of clones (#2, #3, #5, #6, #7, #8, #9, and # Pool), and in the SK-Hep1 cell line, a mother cell line, GPC3 was negative, as illustrated in FIG. 4.

2-3: Analysis of Selective Binding of Anti-GPC3 Antibody to Cell Line Expressing GPC3

Figure 5:
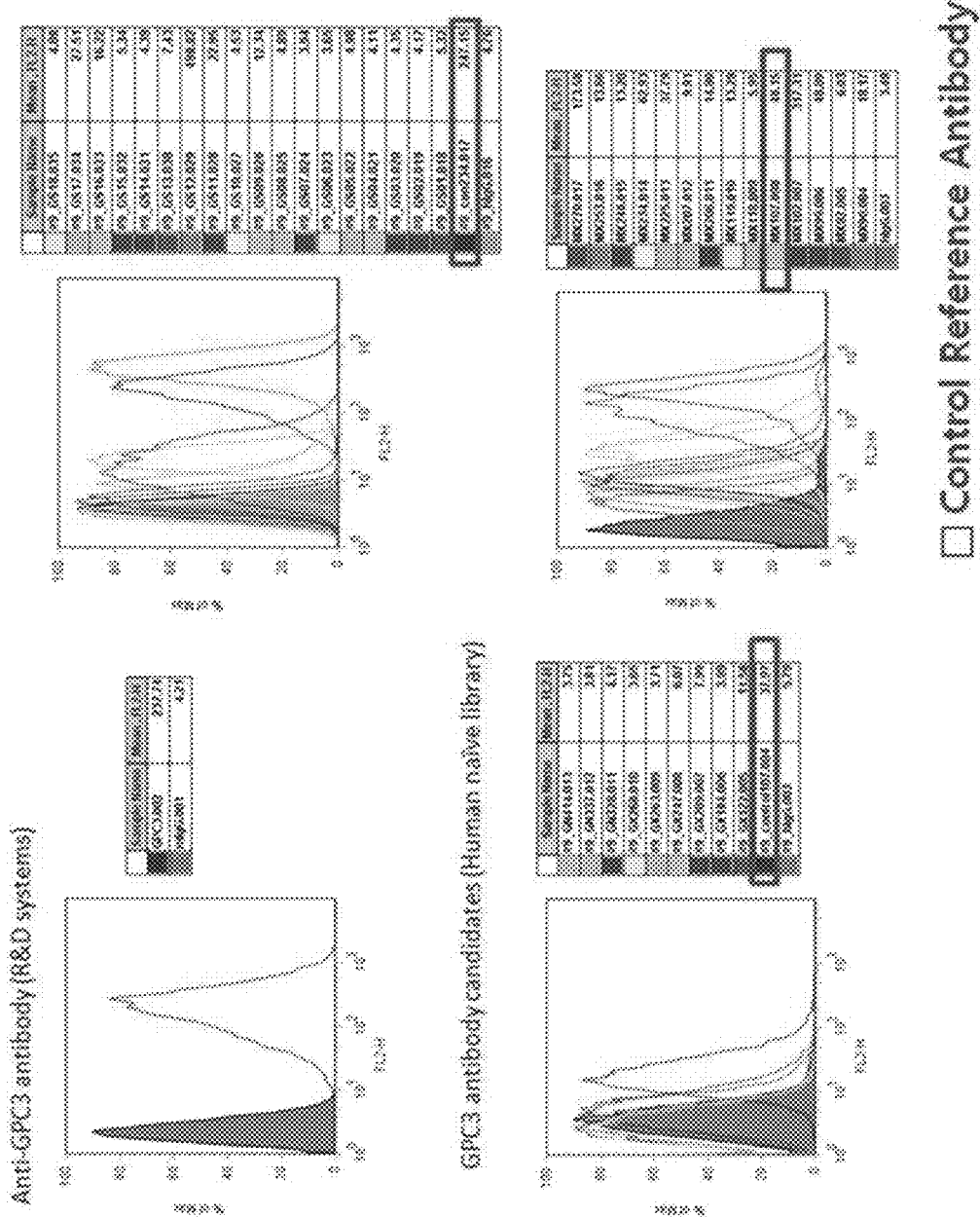
FIG. 5 is a view illustrating that an anti-glypican 3 antibody binds to a cell line transformed so as to express GPC3.

Whether or not anti-GPC3 antibody selectively binds to a cell line (SK-Hep1-GPC3) in which GPC3 was artificially over-expressed was measured using a FACS experiment. After detaching SK-Hep1-GPC3 cells by adding a TrypLE Express solution thereto, the detached SK-Hep1-GPC3 cells were put into a 50 mL tube and centrifuged at room temperature and 2000 rpm for 3 minutes to remove a culture medium, followed by washing with PBS once. The resultant was suspended using a FACS buffer, transferred to a round bottom tube, and centrifuged at room temperature and 2000 rpm for 3 minutes. A supernatant was removed, and the resultant was suitably dissolved using the FACS buffer so as to have a concentration of $4 \times 10^5$ ea/mL. Then, a candidate antibody (1 µg) was added thereto at 4° C., and in an isotope control group, a human IgG (1 µg, Sigma) was added instead of the candidate antibody. After 1 hour, the resultant was washed with the FACS buffer two times, a goat anti-human IgG antibody and FITC conjugated were added thereto at an amount of 1 µL per sample and bound thereto at 4° C. for 30 minutes. After collecting cells by centrifugation at 2000 rpm for 3 minutes, the cells were re-suspended by adding a fixation buffer (500 µL), and measured using a FACS calibur (FIG. 5).

Figure 6:
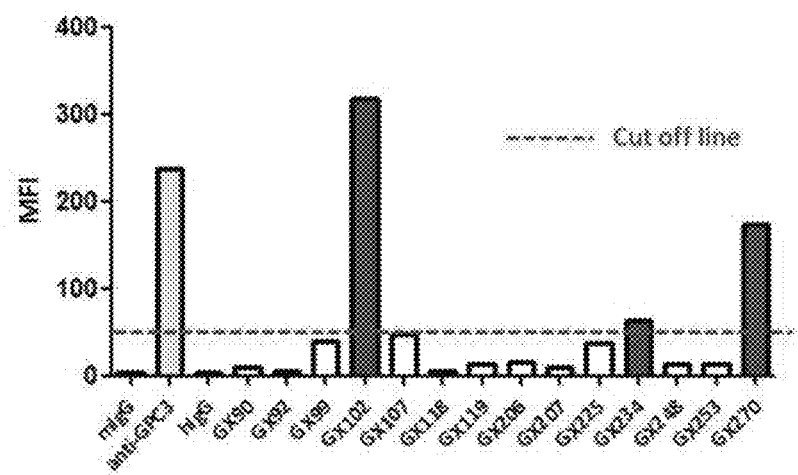
FIG. 6 is a view illustrating binding affinity of an anti-glypican 3 antibody according to the present invention to a transformed cell line (SK-Hep1-GPC3) so as to express GPC3.
Figure 6:
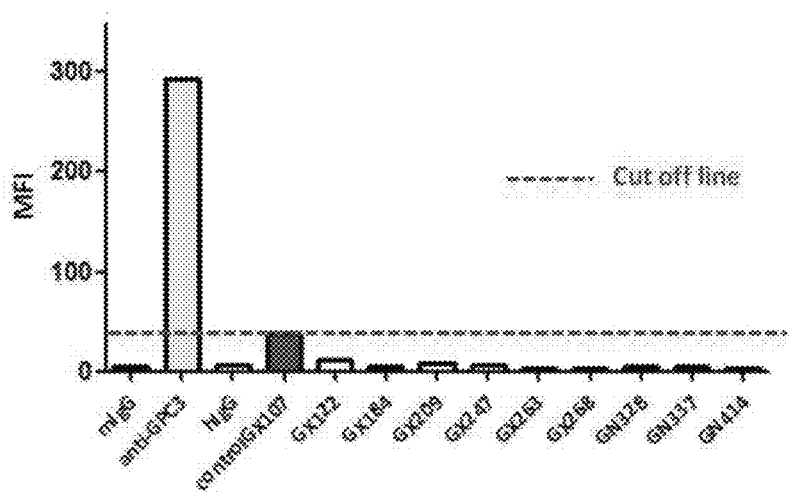
Figure 6:
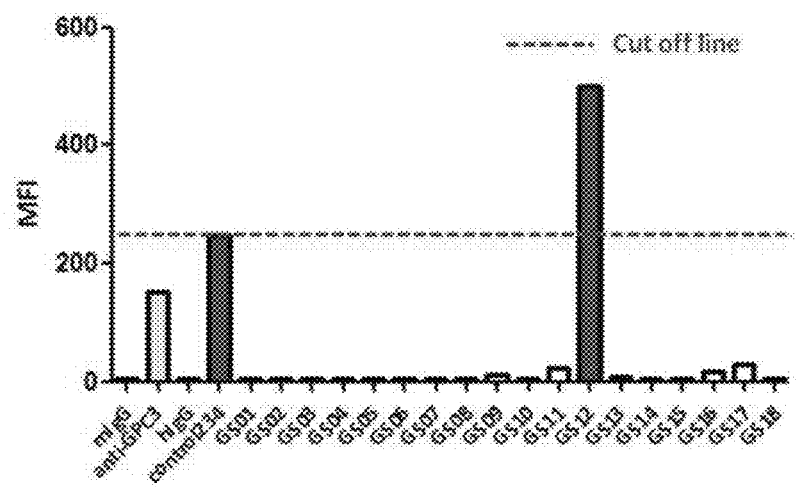
Figure 7:
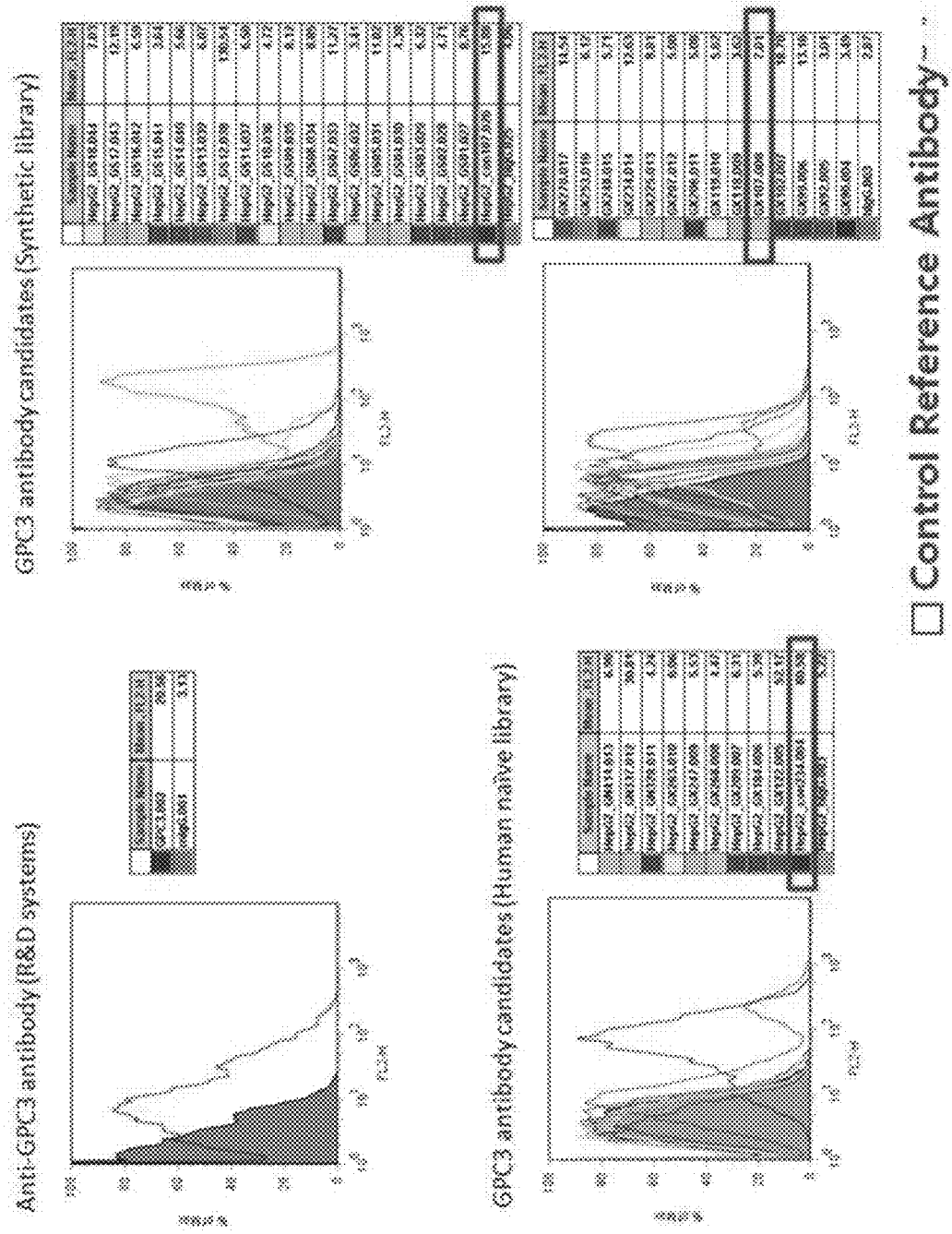
FIG. 7 is a view illustrating binding affinity of the anti-glypican 3 antibody according to the present invention to a cell line (HepG2) expressing GPC3.
Figure 8:
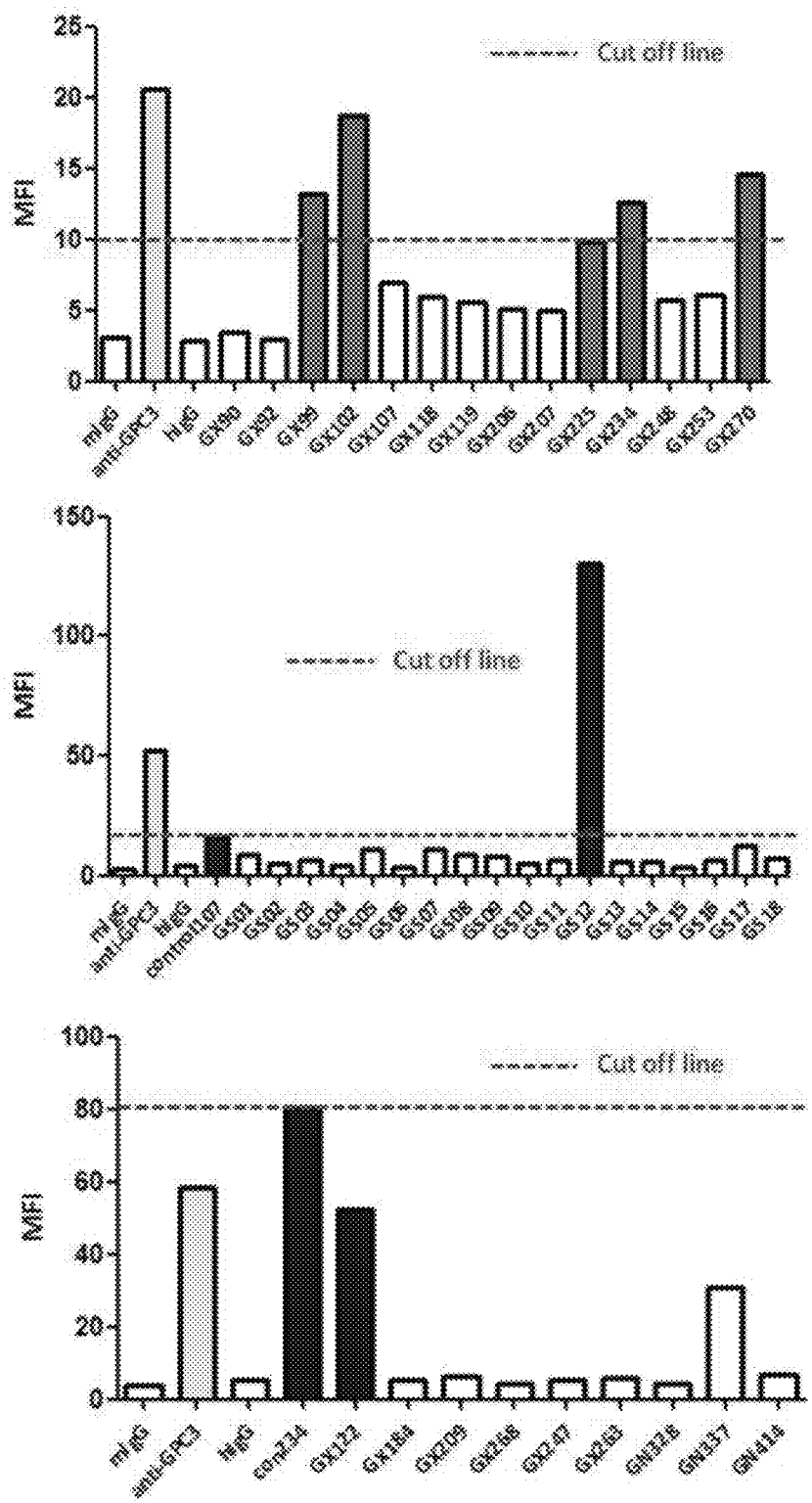
FIG. 8 is a view illustrating binding affinity of the anti-glypican 3 antibody according to the present invention to a cell line (HepG2) expressing GPC3.

In order to compare binding capacity between the analyzed candidate antibodies, a reference antibody was set in each analysis, and the binding capacity was compared based on mean fluorescent intensity (MFI) (FIG. 6). Since the SK-Hep1-GPC3 cells were cell lines in which GPC3 was artificially over-expressed, it is impossible to predicate that the SK-Hep1-GPC3 cells maintained an original GPC3 structure as it is. Therefore, whether or not the anti-GPC3 antibody was selectively bound to cells even in hepatic cancer cells (HepG2) in which GPC3 was originally expressed was compared and analyzed by the same method as described above (FIGS. 7 and 8). As a result, it was confirmed that the antibodies having excellent binding capacity in both of the two cell lines (SK-Hep1-GPC3 and HepG2) were GX102, GX270, and GS012 clone.

Figure 9:
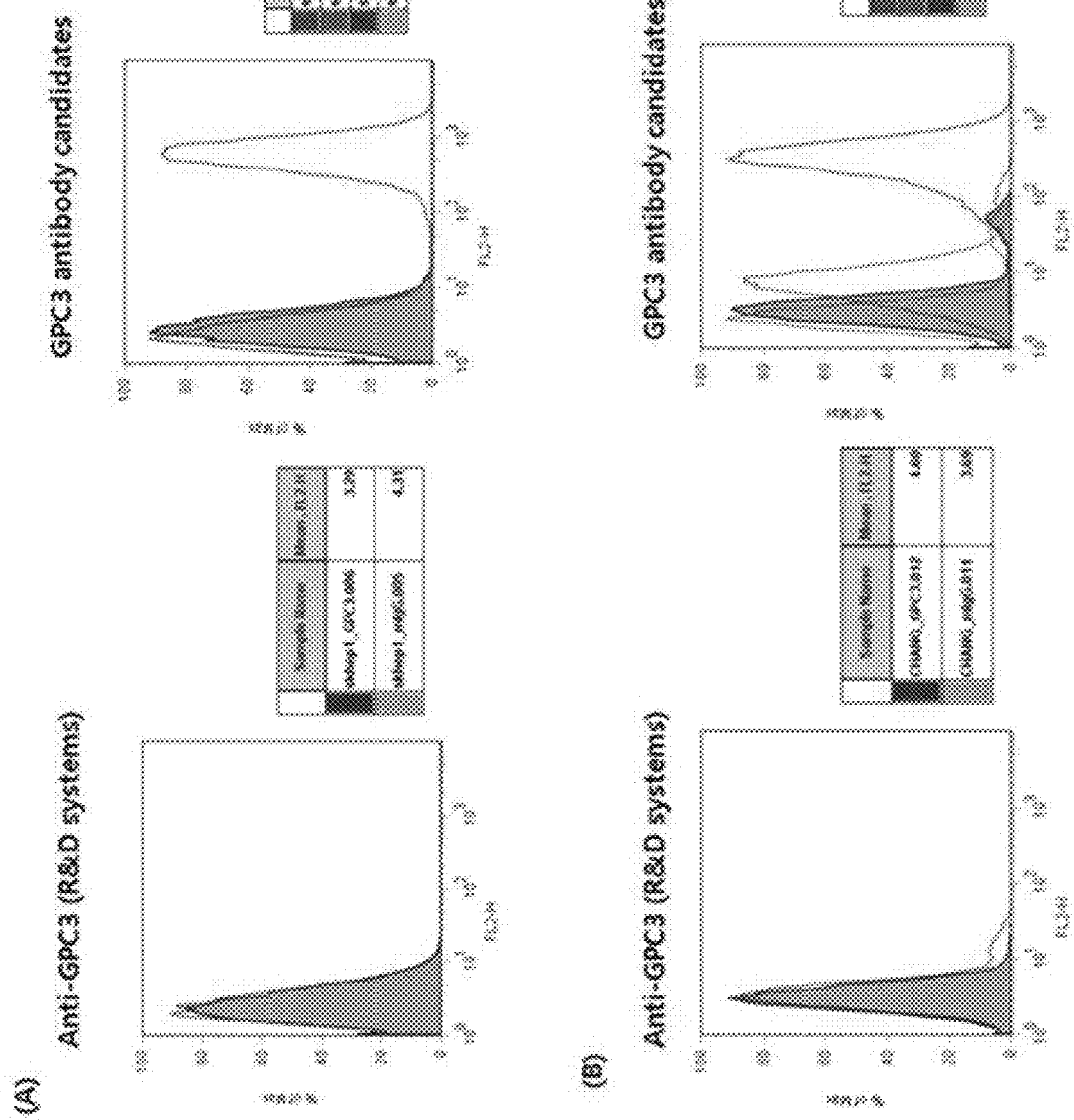
FIG. 9 is a view illustrating results obtained by confirming whether or not GX102, GX270, and GS012 clone antibodies according to the present invention selectively bind to cell lines in proportion to an expression level of GPC3 in seven types of hepatic cancer cell lines (SK-Hep1, PLC/PRF/5, SNU398, Hep3B, Huh7, HepG2, and SK-Hep1-GPC3 #9) and one kind of normal hepatic cancer cell line (CHANG).

In order to confirm whether or not the GX102, GX270, and GS012 clone antibodies having excellent binding capacity to GPC3 selectively bind to cell lines in proportion to an expression level of GPC3 in tumor cells, FACS binding was measured in a total of seven kinds of hepatic cancer cell lines (SK-Hep1, PLC/PRF/5, SNU398, Hep3B, Huh7, HepG2, and SK-Hep1-GPC3 #9) and one kind of normal hepatic cancer cell line (CHANG) (FIG. 9). The results were represented and compared by positive signs depending on an overlapping profile of a FACS histogram with that in an isotope negative control group (Table 6 and FIG. 10).

As a result, GX102 and GX270 candidate antibodies were selectively bound to the hepatic cancer cell lines in proportion to the expression level of GPC3 as illustrated in Table 6 and FIGS. 9 and 10. On the contrary, it was confirmed that the GS012 antibody was non-specifically bound to all of the hepatic cancer cell lines regardless of the expression level of GPC3.

TABLE 6

| GPC3Ab | SK-Hep1 | PLC/PRF/5 | CHANG | SNU398 | Hep3B | Huh7 | HepG2 | SK-Hep1-GPC3 #9 |
|---|---|---|---|---|---|---|---|---|
| GPCSexp. | − | − | − | −/+ | + | ++ | ++ | ++ |
| GS012 | +++ | +++ | +++ | ++ | +++ | +++ | ++ | +++ |
| GX102 | − | − | − | − | + | ++ | + | +++ |
| GX270 | − | − | + | − | − | + | + | ++ |

INDUSTRIAL APPLICABILITY

An antibody specifically binding to glypican 3 according to the present invention may be effectively used to treat cancer or tumor, particularly, hepatocellular carcinoma due to high affinity and specificity to glypican 3.

Although the present invention has been described in detail based on particular features thereof, it is obvious to those skilled in the art that these specific technologies are merely preferable embodiments and thus the scope of the present invention is not limited to the embodiments. Therefore, the substantial scope of the present invention is defined by the accompanying claims and equivalent thereof.

SEQUENCE LISTING FREE TEXT

Attached electronic file.

The invention claimed is:

1. An anti-glypican 3 antibody comprising a heavy chain variable region and a light chain variable region comprising
    a heavy chain CDR1 comprising the amino acid sequence of SEQ ID NO: 149, a heavy chain CDR2 comprising the amino acid sequence of SEQ ID NO: 150, a heavy chain CDR3 comprising the amino acid sequence of SEQ ID NO: 151, a light chain CDR1 comprising the amino acid sequence of SEQ ID NO: 152, a light chain CDR2 comprising the amino acid sequence of SEQ ID NO: 153, and a light chain CDR3 comprising the amino acid sequence of SEO ID NO: 154;
    a heavy chain CDR1 comprising the amino acid sequence of SEQ ID NO: 281, a heavy chain CDR2 comprising the amino acid sequence of SEQ ID NO: 282, a heavy chain CDR3 comprising the amino acid sequence of SEQ ID NO: 283, a light chain CDR1 comprising the amino acid sequence of SEQ ID NO: 156, a light chain CDR2 comprising the amino acid sequence of SEQ ID NO: 284, and a light chain CDR3 comprising the amino acid sequence of SEO ID NO: 158; or
    a heavy chain CDR1 comprising the amino acid sequence of SEQ ID NO: 297, a heavy chain CDR2 comprising the amino acid sequence of SEQ ID NO: 341, a heavy chain CDR3 comprising the amino acid sequence of SEQ ID NO: 342, a light chain CDR1 comprising the amino acid sequence of SEQ ID NO: 343, a light chain CDR2 comprising the amino acid sequence of SEQ ID NO: 301, and a light chain CDR3 comprising the amino acid sequence of SEO ID NO: 344.

2. The anti-glypican 3 antibody according to claim 1, comprising a heavy chain variable region comprising the amino acid sequence of SEQ ID NO: 7, 89, or 113.

3. The anti-glypican 3 antibody according to claim 1, comprising a light chain variable region comprising the amino acid sequence of SEQ ID NO: 8, 90, or 114.

4. A conjugate comprising the anti-glypican 3 antibody according to claim 1 and a drug.

5. The conjugate according to claim 4, wherein the drug is an agent for treating cancer.

6. The conjugate according to claim 5, wherein the drug is at least one selected from the group consisting of a microtubulin inhibitor, a mitosis inhibitor, a topoisomerase inhibitor, a DNA intercalator, a protein toxin performing an enzymatic function, a radioisotope, miRNA, shRNA and siRNA.

7. The conjugate according to claim 5, wherein the drug is at least one selected from the group consisting of maytansinoid, auristatin, dolastatin, trichothecene, CC1065, calicheamicin, taxane, anthracycline, methotrexate, adriamycin, vindesine, vinca alkaloids, mitomycin C, chlorambucil, daunorubicin, daunomycin, etoposide, teniposide, carminomycin, aminopterin, dactinomycin, mitomycins, bleomycins, esperamicins, 5-fluorouracil, melphalan, nucleolytic enzymes, antibiotics, toxins, cisplatin, CPT-11, doxorubicin, paclitaxel and docetaxel.

8. A bispecific antibody comprising the anti-glypican 3 antibody according to claim 1.

9. The bispecific antibody according to claim 8, comprising the anti-glypican 3 antibody and an antibody having binding ability to an immune effector cell-specific target molecule.

10. The bispecific antibody according to claim 9, wherein the immune effector cell-specific target molecule is selected from the group consisting of TCR/CD3, CD16, CD44, CD56, CD69, CD64, CD89 and CD11b/CD18.

11. A polynucleotide encoding the anti-glypican 3 antibody according to claim 1.

12. A recombinant vector comprising the polynucleotide according to claim 11.

13. A host cell transformed with the recombinant vector according to claim 12.

14. The host cell according to claim 13, wherein the cell is selected from the group consisting of animal cell, plant cell, yeast, *E. coli*, and insect cell.

15. The host cell according to claim 13, wherein the cell is selected from the group consisting of monkey kidney cells 7 (COS7), NSO cells, SP2/0, Chinese hamster ovary (CHO) cells, W138, baby hamster kidney (BHK) cells, Madin-Darby canine kidney (MDCK) cells, myeloma cell lines, HuT 78 cells, HEK293 cells, *Escherichia coli, Bacillus* subtilis, Streptomyces sp., Pseudomonas sp., Proteus mirabilis, Staphylococcus sp., Aspergillus sp., Pichia pastoris, Saccharomyces cerevisiae, Schizosaccharomyces sp., and Neurospora crassa.

16. A method of preparing an anti-glypican 3 antibody comprising culturing a host cell according to claim 13.

17. A composition comprising the anti-glypican 3 antibody according to claim 1.

* * * * *

SEQUENCE LISTING

```
<160> NUMBER OF SEQ ID NOS: 393

<210> SEQ ID NO 1
<211> LENGTH: 118
<212> TYPE: PRT
<213> ORGANISM: Artificial Sequence
<220> FEATURE:
<223> OTHER INFORMATION: Clone GX090_Variable heavy chain

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Ser Phe Ser Gly Phe Asp Pro Trp Gly Gln Gly Thr
                100                 105                 110

Leu Val Thr Val Ser Ser
            115

<210> SEQ ID NO 2
<211> LENGTH: 111
<212> TYPE: PRT
<213> ORGANISM: Artificial Sequence
<220> FEATURE:
<223> OTHER INFORMATION: Clone GX090_Variable light chain

<400> SEQUENCE: 2

Gln Ser Val Leu Thr Gln Pro Pro Ser Leu Ser Ala Ala Pro Gly Gln
1               5                   10                  15

Lys Val Thr Ile Ser Cys Ser Gly Ser Ser Ser Asn Ile Gly Lys Asn
                20                  25                  30

His Val Ser Trp Tyr Gln Gln Phe Pro Gly Thr Ala Pro Lys Phe Leu
            35                  40                  45

Ile Tyr Asp Asn His Arg Arg Pro Ser Gly Ile Pro Asp Arg Phe Ser
        50                  55                  60

Gly Ser Lys Ser Gly Thr Ser Ala Thr Leu Asp Ile Thr Gly Leu Gln
65                  70                  75                  80

Thr Gly Asp Glu Ala Thr Tyr Tyr Cys Gly Thr Trp Asp Ser Ser Leu
                85                  90                  95

Ser Ala Val Val Phe Gly Gly Gly Thr Lys Leu Thr Val Leu Gly
                100                 105                 110
```

<210> SEQ ID NO 3
<211> LENGTH: 117
<212> TYPE: PRT
<213> ORGANISM: Artificial Sequence
<220> FEATURE:
<223> OTHER INFORMATION: Clone GX092_Variable heavy chain

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asp Trp Gly Phe Phe Asp Tyr Trp Gly Gln Gly Thr Leu
            100                 105                 110

Val Thr Val Ser Ser
        115

<210> SEQ ID NO 4
<211> LENGTH: 111
<212> TYPE: PRT
<213> ORGANISM: Artificial Sequence
<220> FEATURE:
<223> OTHER INFORMATION: Clone GX092_Variable light chain

<400> SEQUENCE: 4

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Thr Trp Tyr Gln Gln Leu Pro Gly Thr Ala Pro Lys Leu Leu
        35                  40                  45

Ile Tyr Ala Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly
            100                 105                 110

<210> SEQ ID NO 5
<211> LENGTH: 119
<212> TYPE: PRT
<213> ORGANISM: Artificial Sequence
<220> FEATURE:
<223> OTHER INFORMATION: Clone GX099_Variable heavy chain

<400> SEQUENCE: 5

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
                        20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Ser Ser Ser Pro Ala Lys Ile Asp Tyr Trp Gly Gln Gly
                100                 105                 110

Thr Leu Val Thr Val Ser Ser
            115

<210> SEQ ID NO 6
<211> LENGTH: 110
<212> TYPE: PRT
<213> ORGANISM: Artificial Sequence
<220> FEATURE:
<223> OTHER INFORMATION: Clone GX099_Variable light chain

<400> SEQUENCE: 6

Gln Ser Val Leu Thr Gln Pro Pro Ser Val Ser Ala Ala Pro Gly Glu
1               5                   10                  15

Lys Val Ile Ile Ser Cys Ser Gly Ser Ser Ser Asn Ile Gly Lys Tyr
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Ser Gly Leu Gln
65                  70                  75                  80

Thr Gly Asp Glu Ala Asp Tyr Tyr Cys Gly Thr Trp Asp Ser Ser Leu
                85                  90                  95

Asn Leu Val Phe Gly Thr Gly Thr Lys Val Thr Val Leu Gly
                100                 105                 110

<210> SEQ ID NO 7
<211> LENGTH: 118
<212> TYPE: PRT
<213> ORGANISM: Artificial Sequence
<220> FEATURE:
<223> OTHER INFORMATION: Clone GX102_Variable heavy chain

<400> SEQUENCE: 7

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

Ala Arg Arg Gly Leu Arg Gly Asp Phe Asp Tyr Trp Gly Gln Gly Thr
            100                 105                 110

Leu Val Thr Val Ser Ser
        115

<210> SEQ ID NO 8
<211> LENGTH: 111
<212> TYPE: PRT
<213> ORGANISM: Artificial Sequence
<220> FEATURE:
<223> OTHER INFORMATION: Clone GX102_Variable light chain

<400> SEQUENCE: 8

Gly Gln Ser Val Leu Thr Gln Pro Pro Ser Ala Ser Glu Thr Pro Gly
1               5                   10                  15

Gln Lys Val Thr Ile Ser Cys Ser Gly Ser Ser Ser Asn Ile Gly Thr
            20                  25                  30

Asn His Val Phe Trp Tyr Gln Gln Leu Pro Gly Thr Ala Pro Lys Leu
        35                  40                  45

Leu Ile Tyr Arg Asn Asn Leu Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Trp Val Phe Gly Gly Gly Thr Lys Leu Thr Val Leu Gly
            100                 105                 110

<210> SEQ ID NO 9
<211> LENGTH: 118
<212> TYPE: PRT
<213> ORGANISM: Artificial Sequence
<220> FEATURE:
<223> OTHER INFORMATION: Clone GX107_Variable heavy chain

<400> SEQUENCE: 9

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser His Gly Asp Tyr Pro Glu Asp Tyr Trp Gly Gln Gly Thr
            100                 105                 110

Leu Val Thr Val Ser Ser
        115

<210> SEQ ID NO 10
<211> LENGTH: 108
<212> TYPE: PRT
<213> ORGANISM: Artificial Sequence
<220> FEATURE:
<223> OTHER INFORMATION: Clone GX107_Variable light chain

```
<400> SEQUENCE: 10

Tyr Glu Leu Thr Gln Pro Pro Ser Val Ser Val Ser Pro Gly Gln Thr
1               5                   10                  15

Ala Arg Ile Ala Cys Ser Gly Asp Ala Leu Pro Lys His Tyr Ala Tyr
            20                  25                  30

Trp Tyr Gln Gln Lys Ser Gly Gln Ala Pro Val Leu Val Val Tyr Glu
        35                  40                  45

Asp Lys Lys Arg Pro Ala Gly Ile Pro Glu Arg Phe Ser Gly Ser Ser
    50                  55                  60

Ser Gly Thr Val Ala Thr Leu Thr Ile Ser Gly Ala Gln Val Glu Asp
65                  70                  75                  80

Glu Ala His Tyr Tyr Cys Tyr Ser Asp Thr Ser Gly Asn His Arg
                85                  90                  95

Val Phe Gly Gly Gly Thr Lys Leu Thr Val Leu Gly
            100                 105

<210> SEQ ID NO 11
<211> LENGTH: 116
<212> TYPE: PRT
<213> ORGANISM: Artificial Sequence
<220> FEATURE:
<223> OTHER INFORMATION: Clone GX114_Variable heavy chain

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Val Asp Ser Ser Asp Tyr Trp Gly Gln Gly Thr Leu Val
            100                 105                 110

Thr Val Ser Ser
        115

<210> SEQ ID NO 12
<211> LENGTH: 108
<212> TYPE: PRT
<213> ORGANISM: Artificial Sequence
<220> FEATURE:
<223> OTHER INFORMATION: Clone GX114_Variable light chain

<400> SEQUENCE: 12

Ala Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60
```

-continued

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Leu
                 85                  90                  95

Thr Phe Cys Gly Gly Thr Lys Val Glu Ile Lys Arg
            100                 105

<210> SEQ ID NO 13
<211> LENGTH: 120
<212> TYPE: PRT
<213> ORGANISM: Artificial Sequence
<220> FEATURE:
<223> OTHER INFORMATION: Clone GX116_Variable heavy chain

<400> SEQUENCE: 13

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Val Met Val Arg Gly Val Ser Thr Phe Gly Tyr Trp Gly Gln
            100                 105                 110

Gly Thr Leu Val Thr Val Ser Ser
        115                 120

<210> SEQ ID NO 14
<211> LENGTH: 111
<212> TYPE: PRT
<213> ORGANISM: Artificial Sequence
<220> FEATURE:
<223> OTHER INFORMATION: Clone GX116_Variable light chain

<400> SEQUENCE: 14

Gln Ser Val Leu Thr Gln Pro Pro Ser Val Ser Ala Ala Pro Gly Gln
 1               5                  10                  15

Lys Val Ser Ile Ser Cys Ser Gly Ser Ser Ser Asn Ile Gly Lys Asn
                20                  25                  30

Phe Leu Ser Trp Tyr Gln Gln Leu Pro Gly Thr Ala Pro His Leu Leu
             35                  40                  45

Ile Tyr Arg Asn Asn Arg Arg Pro Ser Gly Ile Pro Asp Arg Phe Ser
 50                  55                  60

Gly Ser Lys Ser Gly Thr Ser Ala Thr Leu Thr Ile Thr Gly Leu Gln
 65                  70                  75                  80

Thr Gly Asp Glu Gly Asp Tyr Tyr Cys Gly Ala Trp Asp Ser Arg Leu
                 85                  90                  95

Ser Gly Val Val Phe Gly Gly Gly Thr Lys Leu Thr Val Leu Gly
            100                 105                 110

<210> SEQ ID NO 15
<211> LENGTH: 130
<212> TYPE: PRT
<213> ORGANISM: Artificial Sequence
```

```
<220> FEATURE:
<223> OTHER INFORMATION: Clone GX118_Variable heavy chain

<400> SEQUENCE: 15

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Arg Ser Phe Ala Asp Asn Tyr Val Trp Gly Ser Tyr
            100                 105                 110

Ala Ser Tyr Tyr Phe Asp Tyr Trp Gly Arg Gly Thr Leu Val Thr Val
        115                 120                 125

Ser Ser
    130

<210> SEQ ID NO 16
<211> LENGTH: 111
<212> TYPE: PRT
<213> ORGANISM: Artificial Sequence
<220> FEATURE:
<223> OTHER INFORMATION: Clone GX118_Variable light chain

<400> SEQUENCE: 16

Gln Ser Val Val Thr Gln Pro Pro Ser Val Ser Ala Ala Pro Gly Gln
1               5                   10                  15

Arg Val Thr Ile Ser Cys Ser Gly Ser Ser Ser Asn Ile Gly Asn Asn
            20                  25                  30

Phe Val Ser Trp His Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Ser Leu
                85                  90                  95

Gly Thr Gly Val Phe Gly Gly Gly Thr Lys Leu Thr Val Leu Gly
            100                 105                 110

<210> SEQ ID NO 17
<211> LENGTH: 120
<212> TYPE: PRT
<213> ORGANISM: Artificial Sequence
<220> FEATURE:
<223> OTHER INFORMATION: Clone GX119_Variable heavy chain

<400> SEQUENCE: 17

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Ser Trp Asn Tyr Tyr Gly Met Asp Val Trp Gly Gln
            100                 105                 110

Gly Thr Thr Val Thr Val Ser Ser
            115                 120

<210> SEQ ID NO 18
<211> LENGTH: 108
<212> TYPE: PRT
<213> ORGANISM: Artificial Sequence
<220> FEATURE:
<223> OTHER INFORMATION: Clone GX119_Variable light chain

<400> SEQUENCE: 18

Ala Ile Arg Met Thr Gln Ser Pro Ser Ser Leu Ser Ala Ser Val Gly
 1                   5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Val
                 85                  90                  95

Thr Phe Gly Gly Gly Thr Lys Leu Glu Ile Lys Arg
            100                 105

<210> SEQ ID NO 19
<211> LENGTH: 117
<212> TYPE: PRT
<213> ORGANISM: Artificial Sequence
<220> FEATURE:
<223> OTHER INFORMATION: Clone GX122_Variable heavy chain

<400> SEQUENCE: 19

Glu Val Gln Leu Val Glu Ser Gly Ala Glu Val Lys Lys Pro Gly Ala
 1                   5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Gly Gly Ser Ser Pro Asp Ile Trp Gly Gln Gly Thr Met
            100                 105                 110

Val Thr Val Ser Ser
        115

<210> SEQ ID NO 20
<211> LENGTH: 109
<212> TYPE: PRT
<213> ORGANISM: Artificial Sequence
<220> FEATURE:
<223> OTHER INFORMATION: Clone GX122_Variable light chain

<400> SEQUENCE: 20

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Lys Lys Arg Pro Ser Glu Ile Pro Glu Arg Phe Ser Gly Ser
    50                  55                  60

Ser Ser Gly Thr Met Ala Thr Leu Thr Ile Thr Gly Ala Gln Val Asp
65                  70                  75                  80

Asp Glu Ala Asp Tyr Tyr Cys Tyr Ser Ile Asp Arg Ser Gly Ser Arg
                85                  90                  95

Gly Val Phe Gly Gly Gly Thr Lys Leu Thr Val Leu Gly
            100                 105

<210> SEQ ID NO 21
<211> LENGTH: 122
<212> TYPE: PRT
<213> ORGANISM: Artificial Sequence
<220> FEATURE:
<223> OTHER INFORMATION: Clone GX184_Variable heavy chain

<400> SEQUENCE: 21

Gln Leu Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Ser
            20                  25                  30

Asn Asn Tyr Trp Gly Trp Ile Arg Gln Pro Pro Gly Lys Gly Leu Glu
        35                  40                  45

Trp Ile Gly Ser Ile Phe Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Pro Thr Gly Thr Pro Gly Phe Tyr Phe Asp Tyr Trp
            100                 105                 110

Gly Gln Gly Thr Leu Val Thr Val Ser Ser
        115                 120

<210> SEQ ID NO 22
<211> LENGTH: 111
<212> TYPE: PRT
<213> ORGANISM: Artificial Sequence
<220> FEATURE:
<223> OTHER INFORMATION: Clone GX184_Variable light chain

<400> SEQUENCE: 22

Ser Tyr Glu Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala Trp Val Phe Gly Gly Gly Thr Lys Leu Thr Val Leu Gly
            100                 105                 110

<210> SEQ ID NO 23
<211> LENGTH: 113
<212> TYPE: PRT
<213> ORGANISM: Artificial Sequence
<220> FEATURE:
<223> OTHER INFORMATION: Clone GX186_Variable heavy chain

<400> SEQUENCE: 23

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gln Gly Tyr Trp Gly Arg Gly Thr Leu Val Thr Val Ser
            100                 105                 110

Ser

<210> SEQ ID NO 24
<211> LENGTH: 114
<212> TYPE: PRT
<213> ORGANISM: Artificial Sequence
<220> FEATURE:
<223> OTHER INFORMATION: Clone GX186_Variable light chain

<400> SEQUENCE: 24

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

-continued

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gly Gly Thr Lys Leu Glu Ile
            100                 105                 110

Lys Arg

<210> SEQ ID NO 25
<211> LENGTH: 122
<212> TYPE: PRT
<213> ORGANISM: Artificial Sequence
<220> FEATURE:
<223> OTHER INFORMATION: Clone GX189_Variable heavy chain

<400> SEQUENCE: 25

Gln Leu Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Ser
            20                  25                  30

Asn Asn Tyr Trp Gly Trp Ile Arg Gln Pro Pro Gly Lys Gly Leu Glu
        35                  40                  45

Trp Ile Gly Ser Ile Phe Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Pro Thr Gly Thr Pro Gly Phe Tyr Phe Asp Tyr Trp
            100                 105                 110

Gly Gln Gly Thr Leu Val Thr Val Ser Ser
        115                 120

<210> SEQ ID NO 26
<211> LENGTH: 111
<212> TYPE: PRT
<213> ORGANISM: Artificial Sequence
<220> FEATURE:
<223> OTHER INFORMATION: Clone GX189_Variable light chain

<400> SEQUENCE: 26

Ser Tyr Val Leu Thr Gln Pro Pro Ser Val Ser Lys Gly Leu Arg Gln
1               5                   10                  15

Thr Ala Thr Leu Thr Cys Thr Gly Asn Ser Ser Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Phe Ser
    50                  55                  60

Ala Ser Arg Ser Gly Asn Thr Ala Ser Leu Thr Ile Thr Gly Leu Arg
65                  70                  75                  80

Pro Glu Asp Glu Ala Asp Tyr Tyr Cys Ser Ala Trp Asp Ser Ser Leu
                85                  90                  95

Ser Ala Trp Val Phe Gly Gly Gly Thr Lys Leu Thr Val Leu Gly
            100                 105                 110

<210> SEQ ID NO 27
<211> LENGTH: 114
<212> TYPE: PRT
<213> ORGANISM: Artificial Sequence
<220> FEATURE:

<223> OTHER INFORMATION: Clone GX196_Variable heavy chain

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Val Thr Gly Asp Tyr Trp Gly Arg Gly Thr Leu Val Thr Val
            100                 105                 110

Ser Ser

<210> SEQ ID NO 28
<211> LENGTH: 114
<212> TYPE: PRT
<213> ORGANISM: Artificial Sequence
<220> FEATURE:
<223> OTHER INFORMATION: Clone GX196_Variable light chain

<400> SEQUENCE: 28

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys Arg

<210> SEQ ID NO 29
<211> LENGTH: 117
<212> TYPE: PRT
<213> ORGANISM: Artificial Sequence
<220> FEATURE:
<223> OTHER INFORMATION: Clone GX197_Variable heavy chain

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

```
Gly Trp Ile Ser Ala Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Ser Gln Gly Ser Gly Trp Leu Asp Tyr Trp Gly Gln Gly Thr Leu
                100                 105                 110

Val Thr Val Ser Ser
            115

<210> SEQ ID NO 30
<211> LENGTH: 112
<212> TYPE: PRT
<213> ORGANISM: Artificial Sequence
<220> FEATURE:
<223> OTHER INFORMATION: Clone GX197_Variable light chain

<400> SEQUENCE: 30

Asn Phe Met Leu Thr Gln Pro His Ser Val Ser Glu Ser Pro Gly Lys
 1               5                  10                  15

Thr Val Thr Ile Ser Cys Thr Gly Ser Gly Gly Asn Ile Ala Ser Asn
             20                  25                  30

Tyr Val Gln Trp Phe Gln Gln Arg Pro Gly Ser Ala Pro Thr Thr Val
         35                  40                  45

Ile Tyr Asp Asp Val Gln Arg Pro Ser Gly Val Pro Asn Arg Phe Ser
     50                  55                  60

Gly Ser Ile Asp Ser Ser Asn Ser Ala Ser Leu Ser Ile Ser Gly
 65                  70                  75                  80

Leu Lys Thr Glu Asp Glu Ala Asp Tyr Tyr Cys Gln Ser Tyr Asp Arg
                 85                  90                  95

Thr Tyr Arg Gly Val Phe Gly Gly Gly Thr Lys Leu Thr Val Leu Gly
                100                 105                 110

<210> SEQ ID NO 31
<211> LENGTH: 119
<212> TYPE: PRT
<213> ORGANISM: Artificial Sequence
<220> FEATURE:
<223> OTHER INFORMATION: Clone GX201_Variable heavy chain

<400> SEQUENCE: 31

Gln Val Gln Leu Val Glu Ser Gly Gly Gly Leu Val Asn Pro Gly Gly
 1               5                  10                  15

Ser Leu Arg Leu Ser Cys Ala Ala Ser Gly Phe Thr Phe Ser Asn Tyr
             20                  25                  30

Gly Met Asn Trp Val Arg Gln Ala Pro Gly Lys Gly Leu Glu Trp Val
         35                  40                  45

Ser Ser Ile Ser Thr Arg Ser Gly Tyr Ile Phe Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Pro Asn Arg Ser Gly Met Asp Val Trp Gly Gln Gly
                100                 105                 110

Thr Thr Val Thr Val Ser Ser
            115
```

<210> SEQ ID NO 32
<211> LENGTH: 111
<212> TYPE: PRT
<213> ORGANISM: Artificial Sequence
<220> FEATURE:
<223> OTHER INFORMATION: Clone GX201_Variable light chain

<400> SEQUENCE: 32

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Thr Ser Ser
                85                  90                  95

Asp Thr Leu Val Phe Gly Ser Gly Thr Lys Val Thr Val Leu Gly
            100                 105                 110

<210> SEQ ID NO 33
<211> LENGTH: 114
<212> TYPE: PRT
<213> ORGANISM: Artificial Sequence
<220> FEATURE:
<223> OTHER INFORMATION: Clone GX205_Variable heavy chain

<400> SEQUENCE: 33

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Leu Leu Asp Tyr Trp Gly Gln Gly Thr Leu Val Thr Val
            100                 105                 110

Ser Ser

<210> SEQ ID NO 34
<211> LENGTH: 108
<212> TYPE: PRT
<213> ORGANISM: Artificial Sequence
<220> FEATURE:
<223> OTHER INFORMATION: Clone GX205_Variable light chain

<400> SEQUENCE: 34

Ala Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr

```
                20                  25                  30
Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Leu Leu
                85                  90                  95

Thr Phe Gly Gly Gly Thr Lys Leu Glu Ile Lys Arg
            100                 105

<210> SEQ ID NO 35
<211> LENGTH: 123
<212> TYPE: PRT
<213> ORGANISM: Artificial Sequence
<220> FEATURE:
<223> OTHER INFORMATION: Clone GX206_Variable heavy chain

<400> SEQUENCE: 35

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Leu Gly Asp Tyr Gly Gly Asn Gly Tyr Tyr Phe Asp Tyr
            100                 105                 110

Trp Gly Gln Gly Thr Leu Val Thr Val Ser Ser
            115                 120

<210> SEQ ID NO 36
<211> LENGTH: 111
<212> TYPE: PRT
<213> ORGANISM: Artificial Sequence
<220> FEATURE:
<223> OTHER INFORMATION: Clone GX206_Variable light chain

<400> SEQUENCE: 36

Gln Ser Val Leu Thr Gln Pro Pro Ser Val Ser Ala Ala Ser Gly Gln
 1               5                  10                  15

Lys Val Thr Val Ser Cys Ser Gly Ser Ser Ser Asn Ile Gly Lys Asn
                20                  25                  30

Gly Val Ser Trp His Gln Gln Leu Pro Gly Thr Ala Pro Lys Leu Leu
            35                  40                  45

Ile Tyr Glu Asn Asn Arg Arg Pro Ser Glu Ile Pro Asp Arg Phe Ser
 50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Asp Ser Ser Leu
                85                  90                  95
```

```
Asn Ala Gly Val Phe Gly Thr Gly Thr Lys Val Thr Val Leu Gly
            100                 105                 110
```

<210> SEQ ID NO 37
<211> LENGTH: 123
<212> TYPE: PRT
<213> ORGANISM: Artificial Sequence
<220> FEATURE:
<223> OTHER INFORMATION: Clone GX207_Variable heavy chain

<400> SEQUENCE: 37

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Ile Ala Ala Ala Gly Tyr Tyr Tyr Gly Met Asp Val
            100                 105                 110

Trp Gly Gln Gly Thr Thr Val Thr Val Ser Ser
        115                 120
```

<210> SEQ ID NO 38
<211> LENGTH: 111
<212> TYPE: PRT
<213> ORGANISM: Artificial Sequence
<220> FEATURE:
<223> OTHER INFORMATION: Clone GX207_Variable light chain

<400> SEQUENCE: 38

```
Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Arg Val Ser Trp Tyr Gln Gln Pro Pro Gly Thr Ala Pro Lys Leu
        35                  40                  45

Met Ile Tyr Glu Val Ser Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Thr Thr Tyr Val Phe Gly Thr Gly Thr Lys Val Thr Val Leu Gly
            100                 105                 110
```

<210> SEQ ID NO 39
<211> LENGTH: 117
<212> TYPE: PRT
<213> ORGANISM: Artificial Sequence
<220> FEATURE:
<223> OTHER INFORMATION: Clone GX209_Variable heavy chain

<400> SEQUENCE: 39

```
Gln Val Gln Leu Val Gln Ser Gly Ala Glu Val Lys Lys Pro Gly Ala
```

```
            1               5                  10                  15
Ser Val Lys Val Ser Cys Lys Ala Ser Gly Tyr Thr Phe Thr Ser Tyr
                20                  25                  30
Tyr Met His Trp Val Arg Gln Ala Pro Gly Gln Gly Leu Glu Trp Met
                35                  40                  45
Gly Ile Ile Asn Pro Ser Gly Gly Ser Thr Ser Tyr Ala Gln Lys Phe
                50                  55                  60
Gln Gly Arg Val Thr Met Thr Arg Asp Thr Ser Thr Ser Thr Val Tyr
 65                 70                  75                  80
Met Glu Leu Ser Ser Leu Arg Ser Glu Asp Thr Ala Val Tyr Tyr Cys
                85                  90                  95
Ala Arg Gly Tyr Tyr Tyr Gly Met Asp Val Trp Gly Gln Gly Thr Thr
                100                 105                 110
Val Thr Val Ser Ser
                115
```

<210> SEQ ID NO 40
<211> LENGTH: 107
<212> TYPE: PRT
<213> ORGANISM: Artificial Sequence
<220> FEATURE:
<223> OTHER INFORMATION: Clone GX209_Variable light chain

<400> SEQUENCE: 40

```
Gln Ser Val Leu Thr Gln Pro Pro Ser Ala Ser Val Ser Pro Gly Gln
 1               5                  10                  15
Thr Ala Ser Ile Thr Cys Ser Gly Asp Lys Leu Gly Asp Lys Tyr Val
                20                  25                  30
Phe Trp Tyr Arg Gln Lys Pro Gly Gln Ser Pro Val Leu Val Ile Tyr
                35                  40                  45
Gln Asp Asn Lys Arg Pro Ser Gly Ile Pro Glu Arg Phe Ser Gly Ser
                50                  55                  60
Asn Ser Gly Asn Thr Ala Thr Leu Thr Ile Ser Gly Thr Gln Ala Met
 65                 70                  75                  80
Asp Glu Ala Asp Tyr Tyr Cys Gln Thr Trp Asp Ser Ser Thr Glu Val
                85                  90                  95
Phe Gly Thr Gly Thr Lys Val Thr Val Leu Gly
                100                 105
```

<210> SEQ ID NO 41
<211> LENGTH: 120
<212> TYPE: PRT
<213> ORGANISM: Artificial Sequence
<220> FEATURE:
<223> OTHER INFORMATION: Clone GX213_Variable heavy chain

<400> SEQUENCE: 41

```
Gln Leu Gln Leu Gln Glu Ser Gly Pro Gly Leu Val Lys Pro Ser Glu
 1               5                  10                  15
Thr Leu Ser Leu Thr Cys Thr Val Ser Gly Gly Ser Ile Ser Ser Ser
                20                  25                  30
Ser Tyr Tyr Trp Gly Trp Ile Arg Gln Pro Pro Gly Lys Gly Leu Glu
                35                  40                  45
Trp Ile Gly Ser Ile Tyr Tyr Ser Gly Ser Thr Tyr Tyr Asn Pro Ser
                50                  55                  60
Leu Lys Ser Arg Val Thr Ile Ser Val Asp Thr Ser Lys Asn Gln Phe
 65                 70                  75                  80
```

Ser Leu Lys Leu Ser Ser Val Thr Ala Ala Asp Thr Ala Val Tyr Tyr
            85                  90                  95

Cys Ala Arg Leu Phe Trp Gln Gln Leu Thr Phe Asp Tyr Trp Gly Gln
            100                 105                 110

Gly Thr Leu Val Thr Val Ser Ser
            115                 120

<210> SEQ ID NO 42
<211> LENGTH: 111
<212> TYPE: PRT
<213> ORGANISM: Artificial Sequence
<220> FEATURE:
<223> OTHER INFORMATION: Clone GX213_Variable light chain

<400> SEQUENCE: 42

Gln Ser Val Val Thr Gln Pro Pro Ser Val Ser Ala Ala Pro Gly Gln
1               5                   10                  15

Arg Val Ser Ile Ser Cys Ser Gly Ser Ser Asn Ile Gly Lys Asn
            20                  25                  30

His Val Ile Trp His Gln Gln Phe Pro Gly Thr Ala Pro Lys Leu Leu
            35                  40                  45

Ile Ser Glu Asn Asn Lys Arg Pro Ser Gly Ile Pro Asp Arg Phe Ser
50                  55                  60

Ala Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Thr Trp Asp Asn Ser Leu
            85                  90                  95

Ser Ala Gly Val Phe Gly Gly Gly Thr Lys Leu Thr Val Leu Gly
            100                 105                 110

<210> SEQ ID NO 43
<211> LENGTH: 113
<212> TYPE: PRT
<213> ORGANISM: Artificial Sequence
<220> FEATURE:
<223> OTHER INFORMATION: Clone GX214_Variable heavy chain

<400> SEQUENCE: 43

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Asp Asp Thr Ala Val Tyr Tyr Cys
            85                  90                  95

Ala Thr Leu Tyr Asp Phe Trp Ser Gln Gly Thr Leu Val Thr Val Ser
            100                 105                 110

Ser

<210> SEQ ID NO 44
<211> LENGTH: 108
<212> TYPE: PRT
<213> ORGANISM: Artificial Sequence
<220> FEATURE:

<223> OTHER INFORMATION: Clone GX214_Variable light chain

<400> SEQUENCE: 44

Asn Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp His Gln Gln Lys Pro Gly Lys Ala Pro Glu Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Gly Thr Tyr Tyr Cys Gln Gln Tyr Asp Asn Leu Pro Leu
                85                  90                  95

Thr Phe Gly Gly Gly Thr Lys Val Glu Ile Lys Arg
            100                 105

<210> SEQ ID NO 45
<211> LENGTH: 116
<212> TYPE: PRT
<213> ORGANISM: Artificial Sequence
<220> FEATURE:
<223> OTHER INFORMATION: Clone GX216_Variable heavy chain

<400> SEQUENCE: 45

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Val Asp Ser Ser Asp Tyr Trp Gly Gln Gly Thr Leu Val
            100                 105                 110

Thr Val Ser Ser
        115

<210> SEQ ID NO 46
<211> LENGTH: 111
<212> TYPE: PRT
<213> ORGANISM: Artificial Sequence
<220> FEATURE:
<223> OTHER INFORMATION: Clone GX216_Variable light chain

<400> SEQUENCE: 46

Glu Ile Val Leu Thr Gln Ser Pro Ala Thr Leu Ser Leu Ser Pro Gly
1               5                   10                  15

Glu Ser Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly

```
                    50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                     85                  90                  95

Val Ala Leu Thr Phe Gly Gly Gly Thr Lys Leu Glu Ile Lys Arg
                100                 105                 110

<210> SEQ ID NO 47
<211> LENGTH: 116
<212> TYPE: PRT
<213> ORGANISM: Artificial Sequence
<220> FEATURE:
<223> OTHER INFORMATION: Clone GX217_Variable heavy chain

<400> SEQUENCE: 47

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Ala Pro Gly Lys Gly Leu Glu Trp Val
             35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val Ser Gly Asp Pro Lys Asp Trp Gly Gln Gly Thr Leu Val
            100                 105                 110

Thr Val Ser Ser
            115

<210> SEQ ID NO 48
<211> LENGTH: 109
<212> TYPE: PRT
<213> ORGANISM: Artificial Sequence
<220> FEATURE:
<223> OTHER INFORMATION: Clone GX217_Variable light chain

<400> SEQUENCE: 48

Asp Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Arg
                 85                  90                  95

Glu Leu Phe Gly Pro Gly Thr Lys Val Asp Ile Lys Arg
            100                 105

<210> SEQ ID NO 49
<211> LENGTH: 126
```

<212> TYPE: PRT
<213> ORGANISM: Artificial Sequence
<220> FEATURE:
<223> OTHER INFORMATION: Clone GX219_Variable heavy chain

<400> SEQUENCE: 49

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Val Ala Arg Tyr Cys Ser Ser Thr Ser Cys Arg Thr Gly Gly
            100                 105                 110

Met Asp Val Trp Gly Gln Gly Thr Thr Val Thr Val Ser Ser
            115                 120                 125

<210> SEQ ID NO 50
<211> LENGTH: 111
<212> TYPE: PRT
<213> ORGANISM: Artificial Sequence
<220> FEATURE:
<223> OTHER INFORMATION: Clone GX219_Variable light chain

<400> SEQUENCE: 50

Gln Ser Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Gly Ser Arg
            20                  25                  30

Tyr Val Tyr Trp Tyr Gln Gln Leu Thr Gly Thr Ala Pro Lys Leu Leu
        35                  40                  45

Ile Phe Arg Asn Asp Gln Arg Pro Ser Gly Val Pro Asp Arg Phe Ser
50                  55                  60

Ala Ser Lys Ser Gly Thr Ser Ala Ser Leu Ala Ile Ser Gly Leu Arg
65                  70                  75                  80

Ser Glu Asp Glu Ala Asp Tyr Phe Cys Ala Thr Trp Asp Asp Ser Leu
            85                  90                  95

Ser Ala Trp Val Phe Gly Gly Gly Thr Lys Leu Thr Val Leu Gly
            100                 105                 110

<210> SEQ ID NO 51
<211> LENGTH: 122
<212> TYPE: PRT
<213> ORGANISM: Artificial Sequence
<220> FEATURE:
<223> OTHER INFORMATION: Clone GX221_Variable heavy chain

<400> SEQUENCE: 51

Gln Leu Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Ser
            20                  25                  30

Asn Asn Tyr Trp Gly Trp Ile Arg Gln Pro Pro Gly Lys Gly Leu Glu

```
                35                  40                  45
Trp Ile Gly Ser Ile Phe Tyr Ser Gly Ser Thr Tyr Tyr Asn Pro Ser
         50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Leu Pro Thr Gly Thr Pro Gly Phe Tyr Phe Asp Tyr Trp
            100                 105                 110
Gly Gln Gly Thr Leu Val Thr Val Ser Ser
            115                 120
```

<210> SEQ ID NO 52
<211> LENGTH: 111
<212> TYPE: PRT
<213> ORGANISM: Artificial Sequence
<220> FEATURE:
<223> OTHER INFORMATION: Clone GX221_Variable light chain

<400> SEQUENCE: 52

```
Ser Tyr Val Leu Thr Gln Pro Pro Ser Val Ser Lys Asp Leu Arg Gln
1               5                   10                  15
Thr Ala Thr Leu Thr Cys Thr Gly Asn Ser Ser Asn Val Gly Asn Gln
                20                  25                  30
Gly Ala Ala Trp Val Gln Gln His Gln Gly His Pro Pro Lys Leu Leu
            35                  40                  45
Ser Tyr Arg Asn Asn Lys Arg Pro Ser Gly Ile Ser Glu Arg Leu Ser
        50                  55                  60
Ala Ser Arg Ser Gly Asn Thr Ala Ser Leu Thr Ile Thr Gly Leu Gln
65                  70                  75                  80
Pro Glu Asp Glu Ala Asp Tyr Tyr Cys Ser Ala Trp Asp Ser Ser Leu
                85                  90                  95
Ser Ala Trp Val Phe Gly Gly Gly Thr Lys Leu Thr Val Leu Gly
            100                 105                 110
```

<210> SEQ ID NO 53
<211> LENGTH: 114
<212> TYPE: PRT
<213> ORGANISM: Artificial Sequence
<220> FEATURE:
<223> OTHER INFORMATION: Clone GX222_Variable heavy chain

<400> SEQUENCE: 53

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
                20                  25                  30
Tyr Met Ser Trp Ile Arg Gln Ala Pro Gly Lys Gly Leu Glu Trp Val
            35                  40                  45
Ser Tyr Ile Ser Ser Ser Gly Ser Thr Ile Tyr Tyr Ala Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Val Thr Leu Asp Tyr Trp Gly Arg Gly Thr Leu Val Thr Val
            100                 105                 110
```

-continued

Ser Ser

<210> SEQ ID NO 54
<211> LENGTH: 108
<212> TYPE: PRT
<213> ORGANISM: Artificial Sequence
<220> FEATURE:
<223> OTHER INFORMATION: Clone GX222_Variable light chain

<400> SEQUENCE: 54

```
Ala Ile Arg Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Glu Thr Asp Phe Thr Phe Thr Ile Ser Ser Leu Gln Pro
65                  70                  75                  80

Glu Asp Ile Ala Thr Tyr Tyr Cys Gln Gln Tyr Asp Ser Leu Pro Thr
                85                  90                  95

Thr Phe Gly Pro Gly Thr Lys Val Asp Ile Lys Arg
            100                 105
```

<210> SEQ ID NO 55
<211> LENGTH: 119
<212> TYPE: PRT
<213> ORGANISM: Artificial Sequence
<220> FEATURE:
<223> OTHER INFORMATION: Clone GX224_Variable heavy chain

<400> SEQUENCE: 55

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Pro Arg Ser Ser Phe Asp Tyr Trp Gly Arg Gly
            100                 105                 110

Thr Leu Val Thr Val Ser Ser
        115
```

<210> SEQ ID NO 56
<211> LENGTH: 113
<212> TYPE: PRT
<213> ORGANISM: Artificial Sequence
<220> FEATURE:
<223> OTHER INFORMATION: Clone GX224_Variable light chain

<400> SEQUENCE: 56

```
Asn Phe Met Leu Thr Gln Pro His Ser Val Ser Glu Ser Pro Gly Lys
1               5                   10                  15
```

Thr Val Thr Ile Ser Cys Thr Val Ser Ser Gly Ser Ile Ala Lys Asn
            20                  25                  30

Tyr Val His Trp Tyr Gln Arg Arg Pro Gly Ser Ala Pro Thr Pro Leu
        35                  40                  45

Ile Tyr Glu Asp Asn Arg Arg Pro Ser Gly Val Pro Asp Arg Phe Ser
50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asp
                85                  90                  95

Ser Gly Asp Arg Phe Val Phe Gly Thr Gly Thr Lys Val Thr Val Leu
                100                 105                 110

Gly

<210> SEQ ID NO 57
<211> LENGTH: 119
<212> TYPE: PRT
<213> ORGANISM: Artificial Sequence
<220> FEATURE:
<223> OTHER INFORMATION: Clone GX225_Variable heavy chain

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Gly Pro Ser Gly Gly Met Asp Val Trp Gly Gln Gly
                100                 105                 110

Thr Thr Val Thr Val Ser Ser
            115

<210> SEQ ID NO 58
<211> LENGTH: 109
<212> TYPE: PRT
<213> ORGANISM: Artificial Sequence
<220> FEATURE:
<223> OTHER INFORMATION: Clone GX225_Variable light chain

<400> SEQUENCE: 58

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Ser Ser Tyr Thr Ser Ser Thr Arg
                85                  90                  95

Val Val Phe Gly Gly Thr Lys Leu Thr Val Leu Gly
            100                 105

<210> SEQ ID NO 59
<211> LENGTH: 114
<212> TYPE: PRT
<213> ORGANISM: Artificial Sequence
<220> FEATURE:
<223> OTHER INFORMATION: Clone GX226_Variable heavy chain

<400> SEQUENCE: 59

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Leu Asp Tyr Trp Gly Arg Gly Thr Leu Val Thr Val
            100                 105                 110

Ser Ser

<210> SEQ ID NO 60
<211> LENGTH: 109
<212> TYPE: PRT
<213> ORGANISM: Artificial Sequence
<220> FEATURE:
<223> OTHER INFORMATION: Clone GX226_Variable light chain

<400> SEQUENCE: 60

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Ser
                85                  90                  95

Ile Thr Phe Gly Gln Gly Thr Arg Leu Glu Ile Lys Arg
            100                 105

<210> SEQ ID NO 61
<211> LENGTH: 114
<212> TYPE: PRT
<213> ORGANISM: Artificial Sequence
<220> FEATURE:
<223> OTHER INFORMATION: Clone GX229_Variable heavy chain

<400> SEQUENCE: 61

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Leu Asp Tyr Trp Gly Gln Gly Thr Leu Val Thr Val
            100                 105                 110

Ser Ser

<210> SEQ ID NO 62
<211> LENGTH: 108
<212> TYPE: PRT
<213> ORGANISM: Artificial Sequence
<220> FEATURE:
<223> OTHER INFORMATION: Clone GX229_Variable light chain

<400> SEQUENCE: 62

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Trp Leu
                85                  90                  95

Thr Phe Gly Gly Gly Thr Lys Leu Glu Ile Lys Arg
            100                 105

<210> SEQ ID NO 63
<211> LENGTH: 116
<212> TYPE: PRT
<213> ORGANISM: Artificial Sequence
<220> FEATURE:
<223> OTHER INFORMATION: Clone GX233_Variable heavy chain

<400> SEQUENCE: 63

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr

```
            65                  70                  75                  80
Leu Gln Met Asn Ser Leu Arg Ala Glu Asp Thr Ala Val Tyr Tyr Cys
                    85                  90                  95

Ala Arg Val Val Asp Ser Ser Asp Tyr Trp Gly Gln Gly Thr Leu Val
                100                 105                 110

Thr Val Ser Ser
        115

<210> SEQ ID NO 64
<211> LENGTH: 108
<212> TYPE: PRT
<213> ORGANISM: Artificial Sequence
<220> FEATURE:
<223> OTHER INFORMATION: Clone GX233_Variable light chain

<400> SEQUENCE: 64

Ala Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Arg Ile Ser Arg Val Glu Ala
65                  70                  75                  80

Glu Asp Val Gly Ile Tyr Tyr Cys Met Glu Val Arg Tyr Trp Pro Tyr
                85                  90                  95

Asn Phe Gly Gln Gly Thr Lys Leu Glu Ile Lys Arg
                100                 105

<210> SEQ ID NO 65
<211> LENGTH: 129
<212> TYPE: PRT
<213> ORGANISM: Artificial Sequence
<220> FEATURE:
<223> OTHER INFORMATION: Clone GX234_Variable heavy chain

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Gly Leu Gly Asp Phe Trp Ser Gly Asp Tyr Tyr Tyr Tyr
                100                 105                 110

Tyr Tyr Gly Met Asp Val Trp Gly Gln Gly Thr Thr Val Thr Val Ser
            115                 120                 125

Ser
```

<210> SEQ ID NO 66
<211> LENGTH: 111
<212> TYPE: PRT
<213> ORGANISM: Artificial Sequence
<220> FEATURE:
<223> OTHER INFORMATION: Clone GX234_Variable light chain

<400> SEQUENCE: 66

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Ala
            20                  25                  30

Ser Trp Tyr His Gln Lys Pro Gly Gln Ala Pro Val Leu Val Met Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys His Ser Arg Asp Ser Thr Gly Ser His
                85                  90                  95

Pro Asn Trp Val Phe Gly Gly Gly Thr Lys Leu Thr Val Leu Gly
            100                 105                 110

<210> SEQ ID NO 67
<211> LENGTH: 116
<212> TYPE: PRT
<213> ORGANISM: Artificial Sequence
<220> FEATURE:
<223> OTHER INFORMATION: Clone GX235_Variable heavy chain

<400> SEQUENCE: 67

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ser Gly Asp Pro Lys Asp Trp Gly Gln Gly Thr Leu Val
            100                 105                 110

Thr Val Ser Ser
        115

<210> SEQ ID NO 68
<211> LENGTH: 114
<212> TYPE: PRT
<213> ORGANISM: Artificial Sequence
<220> FEATURE:
<223> OTHER INFORMATION: Clone GX235_Variable light chain
<220> FEATURE:
<221> NAME/KEY: misc_feature
<222> LOCATION: (85)..(85)
<223> OTHER INFORMATION: Xaa can be any naturally occurring amino acid

<400> SEQUENCE: 68

Ala Ile Gln Met Thr Gln Ser Pro Asp Ser Leu Ala Val Ser Leu Gly

```
                1               5                  10                  15
          Glu Arg Ala Thr Ile Asn Cys Lys Ser Ser Gln Ser Val Leu Tyr Ser
                          20                  25                  30

Ser Asn Asn Lys Asn Tyr Leu Ala Trp Tyr Gln Gln Lys Pro Gly Gln
                          35                  40                  45

Pro Pro Lys Leu Leu Ile Tyr Trp Ala Ser Thr Arg Glu Ser Gly Val
                  50                  55                  60

Pro Asp Arg Phe Ser Gly Ser Gly Ser Gly Thr Asp Phe Thr Leu Thr
          65                  70                  75                  80

Ile Ser Ser Leu Xaa Ala Glu Asp Val Ala Val Tyr Tyr Cys Gln Gln
                          85                  90                  95

Tyr Tyr Ser Thr Pro Leu Thr Phe Gly Gly Gly Thr Lys Leu Glu Ile
                          100                 105                 110

Lys Arg

<210> SEQ ID NO 69
          <211> LENGTH: 117
          <212> TYPE: PRT
          <213> ORGANISM: Artificial Sequence
          <220> FEATURE:
          <223> OTHER INFORMATION: Clone GX242_Variable heavy chain

<400> SEQUENCE: 69

Gln Val Gln Leu Val Glu Ser Gly Gly Gly Leu Val Lys Pro Gly Gly
          1               5                   10                  15

Ser Leu Arg Leu Ser Cys Ala Ala Ser Gly Phe Thr Phe Ser Asp Tyr
                          20                  25                  30

Tyr Met Ser Trp Ile Arg Gln Ala Pro Gly Lys Gly Leu Glu Trp Val
                          35                  40                  45

Ser Tyr Ile Ser Ser Ser Gly Ser Thr Ile Tyr Tyr Ala Asp Ser Val
                  50                  55                  60

Lys Gly Arg Phe Thr Ile Ser Arg Asp Asn Ala Lys Asn Ser Leu Tyr
          65                  70                  75                  80

Leu Gln Met Asn Ser Leu Arg Ala Glu Asp Thr Ala Val Tyr Tyr Cys
                          85                  90                  95

Ala Arg Val Val Ala Ala Arg Glu Asp Tyr Trp Gly Gln Gly Thr Leu
                          100                 105                 110

Val Thr Val Ser Ser
                  115

<210> SEQ ID NO 70
          <211> LENGTH: 108
          <212> TYPE: PRT
          <213> ORGANISM: Artificial Sequence
          <220> FEATURE:
          <223> OTHER INFORMATION: Clone GX242_Variable light chain

<400> SEQUENCE: 70

Glu Ile Val Leu Thr Gln Ser Pro Ala Thr Leu Ser Leu Ser Pro Gly
          1               5                   10                  15

Glu Arg Ala Thr Leu Ser Cys Arg Ala Thr Gln Ser Val Gly Ser Tyr
                          20                  25                  30

Leu Ala Trp Tyr Gln Gln Lys Pro Gly Gln Ala Pro Arg Leu Leu Ile
                          35                  40                  45

Tyr Asp Ala Phe Asn Arg Ala Thr Gly Ile Pro Asp Arg Phe Ser Gly
                  50                  55                  60

Ser Gly Ser Gly Thr Asp Phe Thr Leu Thr Ile Ser Ser Leu Glu Pro
```

```
            65                  70                  75                  80
        Glu Asp Phe Ala Val Tyr Tyr Cys Gln Gln Arg Ser Asn Trp Pro Leu
                        85                  90                  95

Thr Phe Gly Gly Gly Thr Lys Val Glu Ile Lys Arg
                    100                 105

<210> SEQ ID NO 71
<211> LENGTH: 116
<212> TYPE: PRT
<213> ORGANISM: Artificial Sequence
<220> FEATURE:
<223> OTHER INFORMATION: Clone GX245_Variable heavy chain

<400> SEQUENCE: 71

Gln Val Gln Leu Val Glu Ser Gly Gly Gly Leu Val Lys Pro Gly Gly
        1               5                   10                  15

Ser Leu Arg Leu Ser Cys Ala Ala Ser Gly Phe Thr Phe Ser Asp Tyr
                    20                  25                  30

Tyr Met Ser Trp Ile Arg Gln Ala Pro Gly Lys Gly Leu Glu Trp Val
                    35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
        65                  70                  75                  80

Leu Gln Met Asn Ser Leu Arg Ala Glu Asp Thr Ala Val Tyr Tyr Cys
                        85                  90                  95

Ala Arg Val Ser Asp Asp Ser Pro Tyr Trp Gly Gln Gly Thr Leu Val
                    100                 105                 110

Thr Val Ser Ser
                    115

<210> SEQ ID NO 72
<211> LENGTH: 109
<212> TYPE: PRT
<213> ORGANISM: Artificial Sequence
<220> FEATURE:
<223> OTHER INFORMATION: Clone GX245_Variable light chain

<400> SEQUENCE: 72

Val Ile Trp Met Thr Gln Ser Pro Ser Ser Leu Ser Ala Ser Val Gly
        1               5                   10                  15

Asp Arg Val Thr Ile Thr Cys Gln Ala Ser Gln Asp Ile Ser Asn Tyr
                    20                  25                  30

Leu Asn Trp Tyr Gln Gln Lys Pro Gly Lys Ala Pro Lys Leu Leu Ile
                    35                  40                  45

Tyr Asp Ala Ser Asn Leu Glu Thr Gly Val Pro Ser Arg Phe Ser Gly
            50                  55                  60

Ser Gly Ser Gly Thr Asp Phe Thr Phe Thr Ile Ser Ser Leu Gln Pro
        65                  70                  75                  80

Glu Asp Ile Ala Thr Tyr Tyr Cys Gln Gln Tyr Asp Asn Leu Leu Ala
                        85                  90                  95

Leu Thr Phe Gly Gly Gly Thr Lys Leu Glu Ile Lys Arg
                    100                 105

<210> SEQ ID NO 73
<211> LENGTH: 124
<212> TYPE: PRT
<213> ORGANISM: Artificial Sequence
<220> FEATURE:
```

<223> OTHER INFORMATION: Clone GX247_Variable heavy chain

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Arg Lys Gly Ser Gly Tyr Ser Tyr Gly Tyr Gly Met Asp
            100                 105                 110

Val Trp Gly Gln Gly Thr Thr Val Thr Val Ser Ser
        115                 120

<210> SEQ ID NO 74
<211> LENGTH: 106
<212> TYPE: PRT
<213> ORGANISM: Artificial Sequence
<220> FEATURE:
<223> OTHER INFORMATION: Clone GX247_Variable light chain

<400> SEQUENCE: 74

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Tyr Val
            20                  25                  30

Ser Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Gly Tyr Tyr Cys Gln Thr Trp Asp Ser Ser Val Val Phe
                85                  90                  95

Gly Gly Gly Thr Lys Leu Thr Val Leu Gly
            100                 105

<210> SEQ ID NO 75
<211> LENGTH: 122
<212> TYPE: PRT
<213> ORGANISM: Artificial Sequence
<220> FEATURE:
<223> OTHER INFORMATION: Clone GX248_Variable heavy chain

<400> SEQUENCE: 75

Gln Met Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe

```
                50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Val Arg Gly Thr Gly Pro Arg Gly Thr Phe Asp Tyr Trp
                100                 105                 110

Gly Gln Gly Thr Leu Val Thr Val Ser Ser
            115                 120

<210> SEQ ID NO 76
<211> LENGTH: 111
<212> TYPE: PRT
<213> ORGANISM: Artificial Sequence
<220> FEATURE:
<223> OTHER INFORMATION: Clone GX248_Variable light chain

<400> SEQUENCE: 76

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                    85                  90                  95

Ser Ala Trp Val Phe Gly Gly Gly Thr Lys Leu Thr Val Leu Gly
                100                 105                 110

<210> SEQ ID NO 77
<211> LENGTH: 116
<212> TYPE: PRT
<213> ORGANISM: Artificial Sequence
<220> FEATURE:
<223> OTHER INFORMATION: Clone GX253_Variable heavy chain

<400> SEQUENCE: 77

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Thr Thr Ile Tyr Tyr Ala Asp Ser Val
        50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
                    85                  90                  95

Ala Arg Val Arg Asp Ser Ser Gly Phe Trp Gly Arg Gly Thr Leu Val
                100                 105                 110

Thr Val Ser Ser
            115
```

<210> SEQ ID NO 78
<211> LENGTH: 111
<212> TYPE: PRT
<213> ORGANISM: Artificial Sequence
<220> FEATURE:
<223> OTHER INFORMATION: Clone GX253_Variable light chain

<400> SEQUENCE: 78

```
Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Val Gly Gly Thr Lys Leu Thr Val Leu Gly
            100                 105                 110
```

<210> SEQ ID NO 79
<211> LENGTH: 116
<212> TYPE: PRT
<213> ORGANISM: Artificial Sequence
<220> FEATURE:
<223> OTHER INFORMATION: Clone GX259_Variable heavy chain

<400> SEQUENCE: 79

```
Gln Val Gln Leu Val Gln Ser Gly Ala Glu Val Lys Lys Pro Gly Glu
1               5                   10                  15

Ser Leu Arg Ile Ser Cys Lys Ala Ser Gly Tyr Lys Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Leu
    50                  55                  60

Gln Gly Gln Val Thr Ile Ser Ala Asp Lys Ser Ile Thr Thr Ala Tyr
65                  70                  75                  80

Leu Gln Trp Ser Ser Leu Arg Ala Ser Asp Thr Ala Met Tyr Tyr Cys
                85                  90                  95

Ala Thr Ile Gly Leu Arg Glu Gly Arg Trp Gly Gln Gly Thr Leu Val
            100                 105                 110

Thr Val Ser Ser
        115
```

<210> SEQ ID NO 80
<211> LENGTH: 106
<212> TYPE: PRT
<213> ORGANISM: Artificial Sequence
<220> FEATURE:
<223> OTHER INFORMATION: Clone GX259_Variable light chain

<400> SEQUENCE: 80

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
```

```
                20                  25                  30
Leu Ala Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Phe
                85                  90                  95

Gly Gln Gly Thr Lys Leu Glu Ile Lys Arg
            100                 105
```

<210> SEQ ID NO 81
<211> LENGTH: 120
<212> TYPE: PRT
<213> ORGANISM: Artificial Sequence
<220> FEATURE:
<223> OTHER INFORMATION: Clone GX263_Variable heavy chain

<400> SEQUENCE: 81

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Val Thr Pro Tyr Tyr Tyr Gly Met Asp Val Trp Gly Gln
            100                 105                 110

Gly Thr Thr Val Thr Val Ser Ser
        115                 120
```

<210> SEQ ID NO 82
<211> LENGTH: 111
<212> TYPE: PRT
<213> ORGANISM: Artificial Sequence
<220> FEATURE:
<223> OTHER INFORMATION: Clone GX263_Variable light chain

<400> SEQUENCE: 82

```
Gln Ser Val Val Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Ser Asn Lys Arg Pro Pro Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Ala Trp Asp Ser Ser Leu
                85                  90                  95
```

```
Ser Ala Val Val Phe Gly Gly Gly Thr Lys Leu Thr Val Leu Gly
            100                 105                 110
```

```
<210> SEQ ID NO 83
<211> LENGTH: 129
<212> TYPE: PRT
<213> ORGANISM: Artificial Sequence
<220> FEATURE:
<223> OTHER INFORMATION: Clone GX264_Variable heavy chain

<400> SEQUENCE: 83

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Arg Trp Tyr Ser Tyr Gly Tyr Phe Asp Val Arg Gly
            100                 105                 110

Gly Tyr Tyr Phe Asp Tyr Trp Gly Arg Gly Thr Leu Val Thr Val Ser
        115                 120                 125

Ser
```

```
<210> SEQ ID NO 84
<211> LENGTH: 111
<212> TYPE: PRT
<213> ORGANISM: Artificial Sequence
<220> FEATURE:
<223> OTHER INFORMATION: Clone GX264_Variable light chain

<400> SEQUENCE: 84

Gln Ser Val Leu Thr Gln Pro Pro Ser Val Ser Ala Ala Ser Gly Gln
1               5                   10                  15

Lys Val Thr Val Ser Cys Ser Gly Ser Ser Ser Asn Ile Gly Lys Asn
            20                  25                  30

Gly Val Ser Trp His Gln Gln Leu Pro Gly Thr Ala Pro Lys Leu Leu
        35                  40                  45

Ile Tyr Glu Asn Asn Arg Arg Pro Ser Glu Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Ser Ser Leu
                85                  90                  95

Asn Ala Gly Val Phe Gly Thr Gly Thr Lys Val Thr Val Leu Gly
            100                 105                 110
```

```
<210> SEQ ID NO 85
<211> LENGTH: 114
<212> TYPE: PRT
<213> ORGANISM: Artificial Sequence
<220> FEATURE:
<223> OTHER INFORMATION: Clone GX265_Variable heavy chain

<400> SEQUENCE: 85
```

```
Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val His Leu Asp Tyr Trp Gly Gln Gly Thr Leu Val Thr Val
                100                 105                 110

Ser Ser
```

<210> SEQ ID NO 86
<211> LENGTH: 114
<212> TYPE: PRT
<213> ORGANISM: Artificial Sequence
<220> FEATURE:
<223> OTHER INFORMATION: Clone GX265_Variable light chain

<400> SEQUENCE: 86

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
                100                 105                 110

Lys Arg
```

<210> SEQ ID NO 87
<211> LENGTH: 120
<212> TYPE: PRT
<213> ORGANISM: Artificial Sequence
<220> FEATURE:
<223> OTHER INFORMATION: Clone GX268_Variable heavy chain

<400> SEQUENCE: 87

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Ser Trp Asn Tyr Tyr Gly Met Asp Val Trp Gly Gln
            100                 105                 110

Gly Thr Thr Val Thr Val Ser Ser
            115                 120
```

<210> SEQ ID NO 88
<211> LENGTH: 107
<212> TYPE: PRT
<213> ORGANISM: Artificial Sequence
<220> FEATURE:
<223> OTHER INFORMATION: Clone GX268_Variable light chain

<400> SEQUENCE: 88

```
Asn Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Thr
                 85                  90                  95

Phe Gly Gln Gly Thr Arg Leu Glu Ile Lys Arg
            100                 105
```

<210> SEQ ID NO 89
<211> LENGTH: 117
<212> TYPE: PRT
<213> ORGANISM: Artificial Sequence
<220> FEATURE:
<223> OTHER INFORMATION: Clone GX270_Variable heavy chain

<400> SEQUENCE: 89

```
Gln Val Gln Leu Val Gln Ser Gly Ala Glu Val Lys Lys Pro Gly Ala
  1               5                  10                  15

Ser Val Lys Val Ser Cys Lys Thr Ser Gly Tyr Thr Phe Thr Ser Ser
             20                  25                  30

Tyr Met His Trp Val Arg Gln Ala Pro Gly Gln Gly Leu Glu Trp Met
         35                  40                  45

Gly Ile Ile Asn Pro Asn Ser Arg Gly Thr Asn Tyr Ala Gln Lys Phe
 50                  55                  60

Gln Gly Arg Val Thr Met Thr Ser Asp Thr Ser Ile Ser Thr Ala Tyr
 65                  70                  75                  80

Met Glu Leu Ser Ser Leu Ile Ser Asp Thr Ala Val Tyr Tyr Cys
                 85                  90                  95

Ala Ser Ser Gly Asp Tyr Pro Asp Tyr Trp Gly Gln Gly Thr Leu
            100                 105                 110

Val Thr Val Ser Ser
            115
```

<210> SEQ ID NO 90

<211> LENGTH: 109
<212> TYPE: PRT
<213> ORGANISM: Artificial Sequence
<220> FEATURE:
<223> OTHER INFORMATION: Clone GX270_Variable light chain

<400> SEQUENCE: 90

```
Ser Tyr Glu Leu Thr Gln Pro Pro Ser Val Ser Val Ser Pro Gly Gln
1               5                   10                  15

Thr Ala Arg Ile Ala Cys Ser Gly Asp Ala Leu Pro Lys His Tyr Ala
            20                  25                  30

Tyr Trp Tyr Gln Gln Lys Ser Gly Gln Ala Pro Val Leu Val Val Tyr
        35                  40                  45

Glu Asp Lys Lys Arg Pro Ala Gly Ile Pro Glu Arg Phe Ser Gly Ser
    50                  55                  60

Ser Ser Gly Thr Val Ala Thr Leu Thr Ile Ser Gly Ala Gln Val Glu
65                  70                  75                  80

Asp Glu Ala His Tyr Tyr Cys Tyr Ser Thr Asp Thr Ser Gly Asn His
                85                  90                  95

Arg Val Phe Gly Gly Gly Thr Lys Leu Thr Val Leu Gly
            100                 105
```

<210> SEQ ID NO 91
<211> LENGTH: 125
<212> TYPE: PRT
<213> ORGANISM: Artificial Sequence
<220> FEATURE:
<223> OTHER INFORMATION: Clone GS001_Variable heavy chain

<400> SEQUENCE: 91

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Gly Ile Ser Pro Ser Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Leu Gly Cys Lys Ser Ala Tyr Cys Tyr Tyr Ala Met
            100                 105                 110

Asp Val Trp Gly Gln Gly Thr Leu Val Thr Val Ser Ser
        115                 120                 125
```

<210> SEQ ID NO 92
<211> LENGTH: 111
<212> TYPE: PRT
<213> ORGANISM: Artificial Sequence
<220> FEATURE:
<223> OTHER INFORMATION: Clone GS001_Variable light chain

<400> SEQUENCE: 92

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30
```

Ala Val Asn Trp Tyr Gln Gln Leu Pro Gly Thr Ala Pro Lys Leu Leu
                35                  40                  45

Ile Tyr Ala Asp Ser Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ser Ser Leu
                85                  90                  95

Ser Gly Tyr Val Phe Gly Gly Gly Thr Lys Leu Thr Val Leu Gly
                100                 105                 110

<210> SEQ ID NO 93
<211> LENGTH: 127
<212> TYPE: PRT
<213> ORGANISM: Artificial Sequence
<220> FEATURE:
<223> OTHER INFORMATION: Clone GS002_Variable heavy chain

<400> SEQUENCE: 93

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Gly Tyr
                20                  25                  30

Ser Met Ser Trp Val Arg Gln Ala Pro Gly Lys Gly Leu Glu Trp Val
                35                  40                  45

Ser Ser Ile Ser Pro Gly Gly Ser Ser Thr Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Ser Ser Leu Arg Ala Glu Asp Thr Ala Val Tyr Tyr Cys
                85                  90                  95

Ala Arg Tyr Arg Val Trp His Met Thr Thr Gly Asp Tyr Tyr Ser Asn
                100                 105                 110

Ala Met Asp Val Trp Gly Gln Gly Thr Leu Val Thr Val Ser Ser
                115                 120                 125

<210> SEQ ID NO 94
<211> LENGTH: 111
<212> TYPE: PRT
<213> ORGANISM: Artificial Sequence
<220> FEATURE:
<223> OTHER INFORMATION: Clone GS002_Variable light chain

<400> SEQUENCE: 94

Gln Ser Val Leu Thr Gln Pro Pro Ser Ala Ser Gly Thr Pro Gly Gln
 1               5                   10                  15

Arg Val Thr Ile Ser Cys Thr Gly Ser Ser Ser Asn Ile Gly Ser Asn
                20                  25                  30

Ala Val Ser Trp Tyr Gln Gln Leu Pro Gly Thr Ala Pro Lys Leu Leu
                35                  40                  45

Ile Tyr Asp Asp Asn Lys Arg Pro Ser Gly Val Leu Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Asp Ser Leu
                85                  90                  95

Ser Gly Tyr Val Phe Gly Gly Gly Thr Lys Leu Thr Val Leu Gly
                100                 105                 110

<210> SEQ ID NO 95
<211> LENGTH: 127
<212> TYPE: PRT
<213> ORGANISM: Artificial Sequence
<220> FEATURE:
<223> OTHER INFORMATION: Clone GS003_Variable heavy chain

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

Ser Val Ile Ser Pro Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Val Met Arg Ser Pro His Asn Pro Tyr Tyr Ser Tyr
            100                 105                 110

Gly Met Asp Val Trp Gly Gln Gly Thr Leu Val Thr Val Ser Ser
        115                 120                 125

<210> SEQ ID NO 96
<211> LENGTH: 111
<212> TYPE: PRT
<213> ORGANISM: Artificial Sequence
<220> FEATURE:
<223> OTHER INFORMATION: Clone GS003_Variable light chain

<400> SEQUENCE: 96

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Asp Val Asn Trp Tyr Gln Gln Leu Pro Gly Thr Ala Pro Lys Leu Leu
        35                  40                  45

Ile Tyr Ser Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Ser Gly Tyr Val Phe Gly Gly Gly Thr Lys Leu Thr Val Leu Gly
            100                 105                 110

<210> SEQ ID NO 97
<211> LENGTH: 127
<212> TYPE: PRT
<213> ORGANISM: Artificial Sequence
<220> FEATURE:
<223> OTHER INFORMATION: Clone GS004_Variable heavy chain

<400> SEQUENCE: 97

Glu Val Gln Leu Leu Glu Ser Gly Gly Gly Leu Val Gln Pro Gly Gly
1               5                   10                  15

```
Ser Leu Arg Leu Ser Cys Ala Val Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

Ser Ala Ile Ser Pro Gly Ser Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Val Trp Ala His Ser Ala Ser Ser Tyr Ser Asn
                100                 105                 110

Ala Met Asp Val Trp Gly Gln Gly Thr Leu Val Thr Val Ser Ser
                115                 120                 125

<210> SEQ ID NO 98
<211> LENGTH: 111
<212> TYPE: PRT
<213> ORGANISM: Artificial Sequence
<220> FEATURE:
<223> OTHER INFORMATION: Clone GS004_Variable light chain

<400> SEQUENCE: 98

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ser Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Asp Ser Leu
                85                  90                  95

Asn Gly Tyr Val Phe Gly Gly Gly Thr Lys Leu Thr Val Leu Gly
                100                 105                 110

<210> SEQ ID NO 99
<211> LENGTH: 127
<212> TYPE: PRT
<213> ORGANISM: Artificial Sequence
<220> FEATURE:
<223> OTHER INFORMATION: Clone GS005_Variable heavy chain

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Asp Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Ala Ala Val Arg Arg Tyr Gly Pro Ser Pro Tyr Tyr Tyr
            100                 105                 110

Ala Met Asp Val Trp Gly Gln Gly Thr Leu Val Thr Val Ser Ser
            115                 120                 125

<210> SEQ ID NO 100
<211> LENGTH: 111
<212> TYPE: PRT
<213> ORGANISM: Artificial Sequence
<220> FEATURE:
<223> OTHER INFORMATION: Clone GS005_Variable light chain

<400> SEQUENCE: 100

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 101
<211> LENGTH: 127
<212> TYPE: PRT
<213> ORGANISM: Artificial Sequence
<220> FEATURE:
<223> OTHER INFORMATION: Clone GS006_Variable heavy chain

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
                20                  25                  30

Ser Met Ser Trp Val Arg Gln Ala Pro Gly Lys Gly Leu Glu Trp Val
            35                  40                  45

Ser Ala Ile Ser Pro Gly Gly Ser Lys Tyr Tyr Ala Asp Ser Val
        50                  55                  60

Arg Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Val Gln Lys Ser Ala Lys Asn Val Tyr Ser Ser Asn
            100                 105                 110

Gly Met Asp Val Trp Gly Gln Gly Thr Leu Val Thr Val Ser Ser
            115                 120                 125

<210> SEQ ID NO 102
<211> LENGTH: 111
<212> TYPE: PRT
<213> ORGANISM: Artificial Sequence
<220> FEATURE:
<223> OTHER INFORMATION: Clone GS006_Variable light chain

<400> SEQUENCE: 102

Gln Ser Val Leu Thr Gln Pro Pro Ala Ser Gly Thr Pro Gly Gln
1               5                   10                  15

Arg Val Thr Ile Ser Cys Ser Gly Ser Ser Asn Ile Gly Asn Asn
                20                  25                  30

Ala Val Asn Trp Tyr Gln Gln Leu Pro Gly Thr Ala Pro Lys Leu Leu
            35                  40                  45

Ile Tyr Tyr Asp Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Ala Tyr Val Phe Gly Gly Gly Thr Lys Leu Thr Val Leu Gly
            100                 105                 110

<210> SEQ ID NO 103
<211> LENGTH: 127
<212> TYPE: PRT
<213> ORGANISM: Artificial Sequence
<220> FEATURE:
<223> OTHER INFORMATION: Clone GS007_Variable heavy chain

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Ser Met Ser Trp Val Arg Gln Ala Pro Gly Lys Gly Leu Glu Trp Val
            35                  40                  45

Ser Val Ile Ser His Asp Gly Arg Ser Lys Tyr Tyr Ala Asp Ser Val
50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Val Trp Lys Arg Thr Asn Ala His Ser Tyr Ala Asn
            100                 105                 110

Ala Met Asp Val Trp Gly Gln Gly Thr Leu Val Thr Val Ser Ser
        115                 120                 125

<210> SEQ ID NO 104
<211> LENGTH: 111
<212> TYPE: PRT
<213> ORGANISM: Artificial Sequence
<220> FEATURE:
<223> OTHER INFORMATION: Clone GS007_Variable light chain

<400> SEQUENCE: 104

Gln Ser Val Leu Thr Gln Pro Pro Ser Ala Ser Gly Thr Pro Gly Gln
1               5                   10                  15

Arg Ala Thr Ile Ser Cys Thr Gly Ser Ser Ser Asn Ile Gly Ser Asn
                20                  25                  30

Ser Val Ser Trp Tyr Gln Gln Leu Pro Gly Thr Ala Pro Lys Leu Leu
            35                  40                  45

Ile Tyr Ala Asn Ser Asn Arg Pro Ser Gly Val Pro Asp Arg Phe Ser
50                  55                  60

-continued

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ala Ser Leu
                85                  90                  95

Ser Ala Tyr Val Phe Gly Gly Gly Thr Lys Leu Thr Val Leu Gly
            100                 105                 110

<210> SEQ ID NO 105
<211> LENGTH: 126
<212> TYPE: PRT
<213> ORGANISM: Artificial Sequence
<220> FEATURE:
<223> OTHER INFORMATION: Clone GS008_Variable heavy chain

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Asp Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Val His Cys Arg Arg Asp Gln Cys Tyr Ser Tyr Gly
            100                 105                 110

Met Asp Val Trp Gly Gln Gly Thr Leu Val Thr Val Ser Ser
        115                 120                 125

<210> SEQ ID NO 106
<211> LENGTH: 111
<212> TYPE: PRT
<213> ORGANISM: Artificial Sequence
<220> FEATURE:
<223> OTHER INFORMATION: Clone GS008_Variable light chain

<400> SEQUENCE: 106

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asn Val Thr Trp Tyr Gln Gln Leu Pro Gly Thr Ala Pro Lys Leu Leu
        35                  40                  45

Ile Tyr Ala Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Asn Gly Tyr Val Phe Gly Gly Gly Thr Lys Leu Thr Val Leu Gly
            100                 105                 110

<210> SEQ ID NO 107
<211> LENGTH: 127
<212> TYPE: PRT

<213> ORGANISM: Artificial Sequence
<220> FEATURE:
<223> OTHER INFORMATION: Clone GS009_Variable heavy chain

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Ser Trp Val Arg Leu Ala Pro Gly Lys Gly Leu Glu Trp Val
        35                  40                  45

Ser Val Ile Ser Pro Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu His Thr Ala Val Tyr Tyr Cys
                85                  90                  95

Ala Arg Tyr Arg Val Lys Gln Met Leu Asn Gln Arg Ser Tyr Ser Asn
            100                 105                 110

Ala Met Asp Val Trp Gly Gln Gly Thr Leu Val Thr Val Ser Ser
        115                 120                 125

<210> SEQ ID NO 108
<211> LENGTH: 111
<212> TYPE: PRT
<213> ORGANISM: Artificial Sequence
<220> FEATURE:
<223> OTHER INFORMATION: Clone GS009_Variable light chain

<400> SEQUENCE: 108

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Ser Gly Tyr Val Phe Gly Gly Gly Thr Lys Leu Thr Val Leu Gly
            100                 105                 110

<210> SEQ ID NO 109
<211> LENGTH: 127
<212> TYPE: PRT
<213> ORGANISM: Artificial Sequence
<220> FEATURE:
<223> OTHER INFORMATION: Clone GS010_Variable heavy chain

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

```
Ser Val Ile Ser Pro Ser Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Val Arg Gln Leu Lys His Thr Arg Ser Tyr Ala Asp
            100                 105                 110

Ala Met Asp Val Trp Gly Gln Gly Thr Leu Val Thr Val Ser Ser
            115                 120                 125

<210> SEQ ID NO 110
<211> LENGTH: 111
<212> TYPE: PRT
<213> ORGANISM: Artificial Sequence
<220> FEATURE:
<223> OTHER INFORMATION: Clone GS010_Variable light chain

<400> SEQUENCE: 110

Gln Ser Val Leu Thr Gln Pro Pro Ser Ala Ser Gly Ala Pro Gly Gln
1               5                   10                  15

Arg Val Thr Ile Ser Cys Ser Gly Ser Ser Ser Asn Ile Gly Ser Asn
            20                  25                  30

Ala Val Ser Trp Tyr Gln Gln Leu Pro Gly Thr Ala Pro Lys Leu Leu
        35                  40                  45

Ile Tyr Ala Asn Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Thr Asp Tyr Tyr Cys Ala Ser Trp Asp Ser Ser Leu
                85                  90                  95

Ser Gly Tyr Val Phe Gly Gly Gly Thr Lys Leu Thr Val Leu Gly
            100                 105                 110

<210> SEQ ID NO 111
<211> LENGTH: 127
<212> TYPE: PRT
<213> ORGANISM: Artificial Sequence
<220> FEATURE:
<223> OTHER INFORMATION: Clone GS011_Variable heavy chain

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser Pro Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ala Val Tyr Phe Leu Arg Ser His Gly Ser Tyr Asp Tyr
            100                 105                 110

Gly Met Asp Val Trp Gly Gln Gly Thr Leu Val Thr Val Ser Ser
```

<210> SEQ ID NO 112
<211> LENGTH: 111
<212> TYPE: PRT
<213> ORGANISM: Artificial Sequence
<220> FEATURE:
<223> OTHER INFORMATION: Clone GS011_Variable light chain

<400> SEQUENCE: 112

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Asp Val Thr Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Tyr Ser Leu
                85                  90                  95

Asn Ala Tyr Val Phe Gly Gly Gly Thr Lys Leu Thr Val Leu Gly
            100                 105                 110

<210> SEQ ID NO 113
<211> LENGTH: 116
<212> TYPE: PRT
<213> ORGANISM: Artificial Sequence
<220> FEATURE:
<223> OTHER INFORMATION: Clone GS012_Variable heavy chain

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
            35                  40                  45

Ser Gly Ile Ser Pro Gly Ser Gly Ser Lys Tyr Tyr Ala Asp Ser Val
        50                  55                  60

Arg Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Arg Arg Phe Asp Tyr Trp Gly Gln Gly Thr Leu Val
            100                 105                 110

Thr Val Ser Ser
        115

<210> SEQ ID NO 114
<211> LENGTH: 111
<212> TYPE: PRT
<213> ORGANISM: Artificial Sequence
<220> FEATURE:
<223> OTHER INFORMATION: Clone GS012_Variable light chain

<400> SEQUENCE: 114

Gln Ser Val Leu Thr Gln Pro Pro Ser Ala Ser Gly Thr Pro Gly Gln
1               5                   10                  15

```
Arg Val Thr Ile Ser Cys Thr Gly Ser Ser Ser Asn Ile Gly Asn Asn
             20                  25                  30

Ala Val Thr Trp Tyr Gln Gln Leu Pro Gly Thr Ala Pro Lys Leu Leu
         35                  40                  45

Ile Tyr Ser Asn Ser Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ser Ser Leu
                 85                  90                  95

Asn Gly Tyr Val Phe Gly Gly Gly Thr Lys Leu Thr Val Leu Gly
            100                 105                 110

<210> SEQ ID NO 115
<211> LENGTH: 116
<212> TYPE: PRT
<213> ORGANISM: Artificial Sequence
<220> FEATURE:
<223> OTHER INFORMATION: Clone GS013_Variable heavy chain

<400> SEQUENCE: 115

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Ala Met Ser Trp Val Arg Gln Ala Pro Gly Lys Gly Leu Glu Trp Val
         35                  40                  45

Ser Ser Ile Ser Ser Gly Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Lys Lys Ser Gln Phe Asp Tyr Trp Gly Gln Gly Thr Leu Val
            100                 105                 110

Thr Val Ser Ser
        115

<210> SEQ ID NO 116
<211> LENGTH: 111
<212> TYPE: PRT
<213> ORGANISM: Artificial Sequence
<220> FEATURE:
<223> OTHER INFORMATION: Clone GS013_Variable light chain

<400> SEQUENCE: 116

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ala Asn Ser Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Asp Thr Trp Asp Tyr Ser Leu
```

```
                    85                  90                  95

Ser Gly Tyr Val Phe Gly Gly Gly Thr Lys Leu Thr Val Leu Gly
            100                 105                 110

<210> SEQ ID NO 117
<211> LENGTH: 128
<212> TYPE: PRT
<213> ORGANISM: Artificial Sequence
<220> FEATURE:
<223> OTHER INFORMATION: Clone GS014_Variable heavy chain

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Asn Ser Gly Ser Asn Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Pro Arg Ile Leu Arg Arg Val Asp His Ser Tyr Ser
            100                 105                 110

Tyr Ala Met Asp Val Trp Gly Gln Gly Thr Leu Val Thr Val Ser Ser
        115                 120                 125

<210> SEQ ID NO 118
<211> LENGTH: 111
<212> TYPE: PRT
<213> ORGANISM: Artificial Sequence
<220> FEATURE:
<223> OTHER INFORMATION: Clone GS014_Variable light chain

<400> SEQUENCE: 118

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ser Asn Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu Gly
            100                 105                 110

<210> SEQ ID NO 119
<211> LENGTH: 127
<212> TYPE: PRT
<213> ORGANISM: Artificial Sequence
<220> FEATURE:
<223> OTHER INFORMATION: Clone GS015_Variable heavy chain

<400> SEQUENCE: 119
```

Glu Val Gln Leu Leu Glu Ser Gly Gly Gly Leu Ala Gln Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Val Arg Gln Ala Pro Gly Lys Gly Leu Glu Trp Val
        35                  40                  45

Ser Ala Ile Ser Pro Asp Gly Gly Ser Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Val Ile Lys Leu Arg Ala Gly Trp Tyr Ser Ala Asn
            100                 105                 110

Gly Met Asp Val Trp Gly Gln Gly Thr Leu Val Thr Val Ser Ser
        115                 120                 125

<210> SEQ ID NO 120
<211> LENGTH: 111
<212> TYPE: PRT
<213> ORGANISM: Artificial Sequence
<220> FEATURE:
<223> OTHER INFORMATION: Clone GS015_Variable light chain

<400> SEQUENCE: 120

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Tyr Asn Ser Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Asn Gly Tyr Val Phe Gly Gly Gly Thr Lys Leu Thr Val Leu Gly
            100                 105                 110

<210> SEQ ID NO 121
<211> LENGTH: 127
<212> TYPE: PRT
<213> ORGANISM: Artificial Sequence
<220> FEATURE:
<223> OTHER INFORMATION: Clone GS016_Variable heavy chain

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Tyr Ser Gly Asn Gly Asn Thr Tyr Tyr Ala Asp Ser Val
50                  55                  60

Lys Gly Arg Phe Thr Ile Ser Arg Asp Asn Ser Lys Asn Thr Leu Tyr

```
                        65                  70                  75                  80
Leu Gln Met Asn Ser Leu Arg Ala Glu Asp Thr Ala Val Tyr Tyr Cys
                    85                  90                  95

Ala Arg Ala Leu Ser Ser Cys Pro Arg Gly Pro Cys Tyr Tyr Asp Asp
                100                 105                 110

Gly Met Asp Val Trp Gly Gln Gly Thr Leu Val Thr Val Ser Ser
            115                 120                 125

<210> SEQ ID NO 122
<211> LENGTH: 111
<212> TYPE: PRT
<213> ORGANISM: Artificial Sequence
<220> FEATURE:
<223> OTHER INFORMATION: Clone GS016_Variable light chain
<220> FEATURE:
<221> NAME/KEY: misc_feature
<222> LOCATION: (75)..(75)
<223> OTHER INFORMATION: Xaa can be any naturally occurring amino acid

<400> SEQUENCE: 122

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Asp Val Thr Trp Tyr Gln Gln Leu Pro Gly Thr Ala Pro Lys Leu Leu
            35                  40                  45

Ile Tyr Asp Asn Ser Lys Arg Pro Ser Gly Val Pro Asp Arg Phe Ser
        50                  55                  60

Gly Ser Lys Ser Gly Thr Ser Ala Ser Leu Xaa Ile Ser Gly Leu Arg
65                  70                  75                  80

Ser Gly Asp Glu Ala Asp Tyr Tyr Cys Gly Thr Trp Asp Ala Ser Leu
                85                  90                  95

Ser Ala Tyr Val Phe Gly Gly Gly Thr Lys Leu Thr Val Leu Gly
            100                 105                 110

<210> SEQ ID NO 123
<211> LENGTH: 127
<212> TYPE: PRT
<213> ORGANISM: Artificial Sequence
<220> FEATURE:
<223> OTHER INFORMATION: Clone GS017_Variable heavy chain

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
                20                  25                  30

Ala Met Ser Trp Val Arg Gln Ala Pro Gly Lys Gly Leu Glu Trp Val
            35                  40                  45

Ser Gly Ile Ser Pro Gly Asp Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Arg Met Cys Gln Gly Trp Arg Cys Ser Tyr Ala Asp
            100                 105                 110

Gly Met Asp Val Trp Gly Gln Gly Thr Leu Val Thr Val Ser Ser
            115                 120                 125
```

<210> SEQ ID NO 124
<211> LENGTH: 111
<212> TYPE: PRT
<213> ORGANISM: Artificial Sequence
<220> FEATURE:
<223> OTHER INFORMATION: Clone GS017_Variable light chain

<400> SEQUENCE: 124

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Ser Val Tyr Trp Tyr Gln Gln Leu Pro Gly Thr Ala Pro Lys Leu Leu
        35                  40                  45

Ile Tyr Ser Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ser Ser Leu
                85                  90                  95

Ser Gly Tyr Val Phe Gly Gly Gly Thr Lys Leu Thr Val Leu Gly
            100                 105                 110

<210> SEQ ID NO 125
<211> LENGTH: 127
<212> TYPE: PRT
<213> ORGANISM: Artificial Sequence
<220> FEATURE:
<223> OTHER INFORMATION: Clone GS018_Variable heavy chain

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser Pro Gly Ser Gly Ser Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Val Ile Lys Ile Asn Arg Gln Thr Tyr Tyr Asp Tyr
            100                 105                 110

Gly Met Asp Val Trp Gly Gln Gly Thr Leu Val Thr Val Ser Ser
        115                 120                 125

<210> SEQ ID NO 126
<211> LENGTH: 111
<212> TYPE: PRT
<213> ORGANISM: Artificial Sequence
<220> FEATURE:
<223> OTHER INFORMATION: Clone GS018_Variable light chain

<400> SEQUENCE: 126

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Ser Trp Tyr Gln Gln Leu Pro Gly Thr Ala Pro Lys Leu Leu
        35                  40                  45

Ile Tyr Ser Asp Asn Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ser Leu
            85                  90                  95

Ser Ala Tyr Val Phe Gly Gly Gly Thr Lys Leu Thr Val Leu Gly
            100                 105                 110

<210> SEQ ID NO 127
<211> LENGTH: 113
<212> TYPE: PRT
<213> ORGANISM: Artificial Sequence
<220> FEATURE:
<223> OTHER INFORMATION: Clone GN328_Variable heavy chain

<400> SEQUENCE: 127

Glu Val Gln Leu Val Glu Ser Gly Gly Gly Leu Val Gln Pro Gly Gly
 1               5                  10                  15

Ser Leu Arg Val Ser Cys Ala Ala Ser Gly Phe Thr Phe Ser Thr Ala
            20                  25                  30

Trp Met Asp Trp Val Arg Gln Ala Pro Gly Lys Gly Leu Glu Trp Val
        35                  40                  45

Ala Asn Ile Asn Pro Asp Gly Ser Glu Lys His Tyr Val Asp Ser Val
 50                  55                  60

Lys Gly Arg Phe Thr Val Ser Arg Asp Asn Ala Lys Asn Ser Val Tyr
 65                  70                  75                  80

Leu His Met Asn Asn Leu Arg Ala Glu Asp Thr Ala Val Tyr Tyr Cys
            85                  90                  95

Ser Lys Ala Leu Asp Tyr Trp Gly Gln Gly Thr Thr Val Thr Val Ser
            100                 105                 110

Ser

<210> SEQ ID NO 128
<211> LENGTH: 108
<212> TYPE: PRT
<213> ORGANISM: Artificial Sequence
<220> FEATURE:
<223> OTHER INFORMATION: Clone GN328_Variable light chain

<400> SEQUENCE: 128

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Asn Ile Asn Thr Trp
            20                  25                  30

Leu Ala Trp Tyr Gln Gln Lys Pro Gly Lys Ala Pro Glu Val Leu Ile
        35                  40                  45

Tyr Glu Ala Ser Ser Leu Glu Ser Gly Val Pro Pro Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Ser Ala Thr Tyr Tyr Cys Gln Gln Tyr Asn Thr Tyr Ser Pro
            85                  90                  95

Thr Phe Gly Gln Gly Thr Lys Leu Glu Ile Lys Arg
            100                 105

<210> SEQ ID NO 129
<211> LENGTH: 141
<212> TYPE: PRT
<213> ORGANISM: Artificial Sequence
<220> FEATURE:
<223> OTHER INFORMATION: Clone GN337_Variable heavy chain

<400> SEQUENCE: 129

Glu Val Gln Leu Val Glu Ser Gly Pro Gly Leu Val Lys Pro Ser Gln
1               5                   10                  15

Thr Leu Ser Leu Thr Cys Thr Val Ser Gly Gly Ser Val Ser Ser Gly
            20                  25                  30

Gly Tyr His Trp Asn Trp Ile Arg Gln His Pro Gly Lys Gly Leu Glu
        35                  40                  45

Trp Ile Gly Tyr Ile Phe Asn Ser Gly Asn Thr Asp Tyr Asn Pro Ser
    50                  55                  60

Leu Arg Ser Arg Leu Thr Ile Ser Gln Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Arg Ser Arg Leu Leu Arg Trp Phe Asp Tyr Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly
    130                 135                 140

<210> SEQ ID NO 130
<211> LENGTH: 108
<212> TYPE: PRT
<213> ORGANISM: Artificial Sequence
<220> FEATURE:
<223> OTHER INFORMATION: Clone GN337_Variable light chain

<400> SEQUENCE: 130

Asp Val Val Leu Thr Gln Ser Pro Ser Ser Leu Ser Ala Phe Val Gly
1               5                   10                  15

Asp Arg Val Thr Ile Thr Cys Gln Ala Ser Gln Asp Ile Arg Lys Tyr
            20                  25                  30

Leu Asn Trp Phe Gln Gln Lys Pro Gly Lys Ala Pro Lys Leu Leu Ile
        35                  40                  45

Tyr Asp Ala Ser Thr Leu Glu Thr Gly Val Ser Ser Arg Phe Ser Gly
    50                  55                  60

Ser Gly Ser Gly Thr His Phe Asn Leu Val Ile Ser Ser Leu Glu Pro
65                  70                  75                  80

Glu Asp Ser Ala Thr Tyr Tyr Cys Gln Gln His Asp Phe Val Pro Arg
                85                  90                  95

Thr Phe Gly Gln Gly Thr Lys Leu Glu Ile Lys Arg
            100                 105

<210> SEQ ID NO 131
<211> LENGTH: 121
<212> TYPE: PRT
<213> ORGANISM: Artificial Sequence
<220> FEATURE:
<223> OTHER INFORMATION: Clone GN414_Variable heavy chain

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
            20                  25                  30

Gly Ile Thr Trp Val Arg Gln Ala Pro Gly Gln Gly Leu Glu Trp Met
        35                  40                  45

Gly Arg Ile Thr Pro Asn Asn Gly Val Thr Asp Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Ser Ala Val Tyr Tyr Cys
                85                  90                  95

Ala Arg Glu Ile Gly Ser Ser Ser Trp Lys Leu Leu Asp Pro Trp Gly
            100                 105                 110

Gln Gly Thr Met Val Thr Val Ser Ser
        115                 120

<210> SEQ ID NO 132
<211> LENGTH: 111
<212> TYPE: PRT
<213> ORGANISM: Artificial Sequence
<220> FEATURE:
<223> OTHER INFORMATION: Clone GN414_Variable light chain

<400> SEQUENCE: 132

Gln Ala Val Leu Thr Gln Pro Ser Ser Val Ser Val Ser Pro Gly Gln
1               5                   10                  15

Thr Ala Ser Ile Thr Cys Thr Gly Asn Ser Asn Asn Val Gly Tyr Glu
            20                  25                  30

Gly Ala Ala Trp Val Gln Gln Tyr Gln Gly His Pro Pro Lys Leu Leu
        35                  40                  45

Ser Asp Arg Asn His Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Ser Glu Asp Glu Ala Asp Tyr Tyr Cys Ser Ala Trp Asp Ser Ser Leu
                85                  90                  95

Ser Glu Trp Val Ser Gly Gly Thr Lys Leu Thr Val Leu Gly
            100                 105                 110

<210> SEQ ID NO 133
<211> LENGTH: 5
<212> TYPE: PRT
<213> ORGANISM: Artificial Sequence
<220> FEATURE:
<223> OTHER INFORMATION: clone GX090_Variable heavy chain CDR1

<400> SEQUENCE: 133

Ser Tyr Gly Ile Ser
1               5

<210> SEQ ID NO 134
<211> LENGTH: 17
<212> TYPE: PRT
<213> ORGANISM: Artificial Sequence
<220> FEATURE:
<223> OTHER INFORMATION: clone GX090_Variable heavy chain CDR2

<400> SEQUENCE: 134

```
Trp Ile Ser Ala Tyr Asn Gly Asn Thr Asn Tyr Ala Gln Lys Leu Gln
1               5                   10                  15
Gly
```

<210> SEQ ID NO 135
<211> LENGTH: 9
<212> TYPE: PRT
<213> ORGANISM: Artificial Sequence
<220> FEATURE:
<223> OTHER INFORMATION: clone GX090_Variable heavy chain CDR3

<400> SEQUENCE: 135

```
Gly Ser Ser Phe Ser Gly Phe Asp Pro
1               5
```

<210> SEQ ID NO 136
<211> LENGTH: 13
<212> TYPE: PRT
<213> ORGANISM: Artificial Sequence
<220> FEATURE:
<223> OTHER INFORMATION: clone GX090_Variable light chain CDR1

<400> SEQUENCE: 136

```
Ser Gly Ser Ser Ser Asn Ile Gly Lys Asn His Val Ser
1               5                   10
```

<210> SEQ ID NO 137
<211> LENGTH: 7
<212> TYPE: PRT
<213> ORGANISM: Artificial Sequence
<220> FEATURE:
<223> OTHER INFORMATION: clone GX090_Variable light chain CDR2

<400> SEQUENCE: 137

```
Asp Asn His Arg Arg Pro Ser
1               5
```

<210> SEQ ID NO 138
<211> LENGTH: 9
<212> TYPE: PRT
<213> ORGANISM: Artificial Sequence
<220> FEATURE:
<223> OTHER INFORMATION: clone GX090_Variable light chain CDR3

<400> SEQUENCE: 138

```
Gly Thr Trp Asp Ser Ser Leu Ser Ala
1               5
```

<210> SEQ ID NO 139
<211> LENGTH: 8
<212> TYPE: PRT
<213> ORGANISM: Artificial Sequence
<220> FEATURE:
<223> OTHER INFORMATION: clone GX092_Variable heavy chain CDR3

<400> SEQUENCE: 139

```
Ala Asp Trp Gly Phe Phe Asp Tyr
1               5
```

<210> SEQ ID NO 140
<211> LENGTH: 13
<212> TYPE: PRT
<213> ORGANISM: Artificial Sequence
<220> FEATURE:
<223> OTHER INFORMATION: clone GX092_Variable light chain CDR1

```
<400> SEQUENCE: 140

Ser Gly Ser Ser Ser Asn Ile Gly Ser Asn Thr Val Thr
1               5                   10

<210> SEQ ID NO 141
<211> LENGTH: 7
<212> TYPE: PRT
<213> ORGANISM: Artificial Sequence
<220> FEATURE:
<223> OTHER INFORMATION: clone GX092_Variable light chain CDR2

<400> SEQUENCE: 141

Ala Asn Asn Gln Arg Pro Ser
1               5

<210> SEQ ID NO 142
<211> LENGTH: 9
<212> TYPE: PRT
<213> ORGANISM: Artificial Sequence
<220> FEATURE:
<223> OTHER INFORMATION: clone GX092_Variable light chain CDR3

<400> SEQUENCE: 142

Ala Ala Trp Asp Asp Ser Leu Asn Gly
1               5

<210> SEQ ID NO 143
<211> LENGTH: 5
<212> TYPE: PRT
<213> ORGANISM: Artificial Sequence
<220> FEATURE:
<223> OTHER INFORMATION: clone GX099_Variable heavy chain CDR1

<400> SEQUENCE: 143

Ser Tyr Tyr Met His
1               5

<210> SEQ ID NO 144
<211> LENGTH: 17
<212> TYPE: PRT
<213> ORGANISM: Artificial Sequence
<220> FEATURE:
<223> OTHER INFORMATION: clone GX099_Variable heavy chain CDR2

<400> SEQUENCE: 144

Ile Ile Asn Pro Ser Gly Gly Ser Thr Ser Tyr Ala Gln Lys Phe Gln
1               5                   10                  15

Gly

<210> SEQ ID NO 145
<211> LENGTH: 10
<212> TYPE: PRT
<213> ORGANISM: Artificial Sequence
<220> FEATURE:
<223> OTHER INFORMATION: clone GX099_Variable heavy chain CDR3

<400> SEQUENCE: 145

Tyr Ser Ser Ser Pro Ala Lys Ile Asp Tyr
1               5                   10

<210> SEQ ID NO 146
<211> LENGTH: 12
<212> TYPE: PRT
<213> ORGANISM: Artificial Sequence
<220> FEATURE:
<223> OTHER INFORMATION: clone GX099_Variable light chain CDR1
```

```
<400> SEQUENCE: 146

Gly Ser Ser Ser Asn Ile Gly Lys Tyr Tyr Val Ser
1               5                   10

<210> SEQ ID NO 147
<211> LENGTH: 7
<212> TYPE: PRT
<213> ORGANISM: Artificial Sequence
<220> FEATURE:
<223> OTHER INFORMATION: clone GX099_Variable light chain CDR2

<400> SEQUENCE: 147

Asp Asn Asn Lys Arg Pro Ser
1               5

<210> SEQ ID NO 148
<211> LENGTH: 9
<212> TYPE: PRT
<213> ORGANISM: Artificial Sequence
<220> FEATURE:
<223> OTHER INFORMATION: clone GX099_Variable light chain CDR3

<400> SEQUENCE: 148

Gly Thr Trp Asp Ser Ser Leu Asn Ala
1               5

<210> SEQ ID NO 149
<211> LENGTH: 5
<212> TYPE: PRT
<213> ORGANISM: Artificial Sequence
<220> FEATURE:
<223> OTHER INFORMATION: clone GX102_Variable heavy chain CDR1

<400> SEQUENCE: 149

Gly Tyr Tyr Met His
1               5

<210> SEQ ID NO 150
<211> LENGTH: 17
<212> TYPE: PRT
<213> ORGANISM: Artificial Sequence
<220> FEATURE:
<223> OTHER INFORMATION: clone GX102_Variable heavy chain CDR2

<400> SEQUENCE: 150

Trp Ile Asn Pro Asn Ser Gly Gly Thr Asn Tyr Ala Gln Lys Phe Gln
1               5                   10                  15

Gly

<210> SEQ ID NO 151
<211> LENGTH: 9
<212> TYPE: PRT
<213> ORGANISM: Artificial Sequence
<220> FEATURE:
<223> OTHER INFORMATION: clone GX102_Variable heavy chain CDR3

<400> SEQUENCE: 151

Arg Gly Leu Arg Gly Asp Phe Asp Tyr
1               5

<210> SEQ ID NO 152
<211> LENGTH: 13
<212> TYPE: PRT
<213> ORGANISM: Artificial Sequence
<220> FEATURE:
```

<223> OTHER INFORMATION: clone GX102_Variable light chain CDR1

<400> SEQUENCE: 152

Ser Gly Ser Ser Ser Asn Ile Gly Thr Asn His Val Phe
1               5                   10

<210> SEQ ID NO 153
<211> LENGTH: 7
<212> TYPE: PRT
<213> ORGANISM: Artificial Sequence
<220> FEATURE:
<223> OTHER INFORMATION: clone GX102_Variable light chain CDR2

<400> SEQUENCE: 153

Arg Asn Asn Leu Arg Pro Ser
1               5

<210> SEQ ID NO 154
<211> LENGTH: 8
<212> TYPE: PRT
<213> ORGANISM: Artificial Sequence
<220> FEATURE:
<223> OTHER INFORMATION: clone GX102_Variable light chain CDR3

<400> SEQUENCE: 154

Ala Ala Trp Asp Asp Ser Leu Ser
1               5

<210> SEQ ID NO 155
<211> LENGTH: 9
<212> TYPE: PRT
<213> ORGANISM: Artificial Sequence
<220> FEATURE:
<223> OTHER INFORMATION: clone GX107_Variable heavy chain CDR3

<400> SEQUENCE: 155

Ser His Gly Asp Tyr Pro Glu Asp Tyr
1               5

<210> SEQ ID NO 156
<211> LENGTH: 11
<212> TYPE: PRT
<213> ORGANISM: Artificial Sequence
<220> FEATURE:
<223> OTHER INFORMATION: clone GX107_Variable light chain CDR1

<400> SEQUENCE: 156

Ser Gly Asp Ala Leu Pro Lys His Tyr Ala Tyr
1               5                   10

<210> SEQ ID NO 157
<211> LENGTH: 7
<212> TYPE: PRT
<213> ORGANISM: Artificial Sequence
<220> FEATURE:
<223> OTHER INFORMATION: clone GX107_Variable light chain CDR2

<400> SEQUENCE: 157

Glu Asp Lys Lys Arg Pro Ala
1               5

<210> SEQ ID NO 158
<211> LENGTH: 9
<212> TYPE: PRT
<213> ORGANISM: Artificial Sequence
<220> FEATURE:
<223> OTHER INFORMATION: clone GX107_Variable light chain CDR3

```
<400> SEQUENCE: 158

Tyr Ser Thr Asp Thr Ser Gly Asn His
1               5

<210> SEQ ID NO 159
<211> LENGTH: 5
<212> TYPE: PRT
<213> ORGANISM: Artificial Sequence
<220> FEATURE:
<223> OTHER INFORMATION: clone GX114_Variable heavy chain CDR1

<400> SEQUENCE: 159

Asp Tyr Tyr Met Ser
1               5

<210> SEQ ID NO 160
<211> LENGTH: 17
<212> TYPE: PRT
<213> ORGANISM: Artificial Sequence
<220> FEATURE:
<223> OTHER INFORMATION: clone GX114_Variable heavy chain CDR2

<400> SEQUENCE: 160

Tyr Ile Ser Ser Ser Gly Ser Thr Ile Tyr Tyr Ala Asp Ser Val Lys
1               5                   10                  15

Gly

<210> SEQ ID NO 161
<211> LENGTH: 7
<212> TYPE: PRT
<213> ORGANISM: Artificial Sequence
<220> FEATURE:
<223> OTHER INFORMATION: clone GX114_Variable heavy chain CDR3

<400> SEQUENCE: 161

Val Val Asp Ser Ser Asp Tyr
1               5

<210> SEQ ID NO 162
<211> LENGTH: 11
<212> TYPE: PRT
<213> ORGANISM: Artificial Sequence
<220> FEATURE:
<223> OTHER INFORMATION: clone GX114_Variable light chain CDR1

<400> SEQUENCE: 162

Gln Ala Ser Gln Asp Ile Ser Asn Tyr Leu Asn
1               5                   10

<210> SEQ ID NO 163
<211> LENGTH: 7
<212> TYPE: PRT
<213> ORGANISM: Artificial Sequence
<220> FEATURE:
<223> OTHER INFORMATION: clone GX114_Variable light chain CDR2

<400> SEQUENCE: 163

Asp Ala Ser Asn Leu Glu Thr
1               5

<210> SEQ ID NO 164
<211> LENGTH: 7
<212> TYPE: PRT
<213> ORGANISM: Artificial Sequence
<220> FEATURE:
```

<223> OTHER INFORMATION: clone GX114_Variable light chain CDR3

<400> SEQUENCE: 164

Gln Gln Tyr Asp Asn Leu Pro
1               5

<210> SEQ ID NO 165
<211> LENGTH: 11
<212> TYPE: PRT
<213> ORGANISM: Artificial Sequence
<220> FEATURE:
<223> OTHER INFORMATION: clone GX116_Variable heavy chain CDR3

<400> SEQUENCE: 165

Val Met Val Arg Gly Val Ser Thr Phe Gly Tyr
1               5                   10

<210> SEQ ID NO 166
<211> LENGTH: 13
<212> TYPE: PRT
<213> ORGANISM: Artificial Sequence
<220> FEATURE:
<223> OTHER INFORMATION: clone GX116_Variable light chain CDR1

<400> SEQUENCE: 166

Ser Gly Ser Ser Ser Asn Ile Gly Lys Asn Phe Leu Ser
1               5                   10

<210> SEQ ID NO 167
<211> LENGTH: 7
<212> TYPE: PRT
<213> ORGANISM: Artificial Sequence
<220> FEATURE:
<223> OTHER INFORMATION: clone GX116_Variable light chain CDR2

<400> SEQUENCE: 167

Arg Asn Asn Arg Arg Pro Ser
1               5

<210> SEQ ID NO 168
<211> LENGTH: 9
<212> TYPE: PRT
<213> ORGANISM: Artificial Sequence
<220> FEATURE:
<223> OTHER INFORMATION: clone GX116_Variable light chain CDR3

<400> SEQUENCE: 168

Gly Ala Trp Asp Ser Arg Leu Ser Gly
1               5

<210> SEQ ID NO 169
<211> LENGTH: 7
<212> TYPE: PRT
<213> ORGANISM: Artificial Sequence
<220> FEATURE:
<223> OTHER INFORMATION: clone GX118_Variable heavy chain CDR1

<400> SEQUENCE: 169

Ser Ser Ser Tyr Tyr Trp Gly
1               5

<210> SEQ ID NO 170
<211> LENGTH: 16
<212> TYPE: PRT
<213> ORGANISM: Artificial Sequence
<220> FEATURE:
<223> OTHER INFORMATION: clone GX118_Variable heavy chain CDR2

```
<400> SEQUENCE: 170

Ser Ile Tyr Tyr Ser Gly Ser Thr Tyr Tyr Asn Pro Ser Leu Lys Ser
1               5                   10                  15

<210> SEQ ID NO 171
<211> LENGTH: 9
<212> TYPE: PRT
<213> ORGANISM: Artificial Sequence
<220> FEATURE:
<223> OTHER INFORMATION: clone GX118_Variable heavy chain CDR3

<400> SEQUENCE: 171

Leu Arg Ser Phe Ala Asp Asn Tyr Val
1               5

<210> SEQ ID NO 172
<211> LENGTH: 13
<212> TYPE: PRT
<213> ORGANISM: Artificial Sequence
<220> FEATURE:
<223> OTHER INFORMATION: clone GX118_Variable light chain CDR1

<400> SEQUENCE: 172

Ser Gly Ser Ser Ser Asn Ile Gly Asn Asn Phe Val Ser
1               5                   10

<210> SEQ ID NO 173
<211> LENGTH: 9
<212> TYPE: PRT
<213> ORGANISM: Artificial Sequence
<220> FEATURE:
<223> OTHER INFORMATION: clone GX118_Variable light chain CDR3

<400> SEQUENCE: 173

Gly Thr Trp Asp Asn Ser Leu Gly Thr
1               5

<210> SEQ ID NO 174
<211> LENGTH: 5
<212> TYPE: PRT
<213> ORGANISM: Artificial Sequence
<220> FEATURE:
<223> OTHER INFORMATION: clone GX119_Variable heavy chain CDR1

<400> SEQUENCE: 174

Ser Tyr Gly Met His
1               5

<210> SEQ ID NO 175
<211> LENGTH: 17
<212> TYPE: PRT
<213> ORGANISM: Artificial Sequence
<220> FEATURE:
<223> OTHER INFORMATION: clone GX119_Variable heavy chain CDR2

<400> SEQUENCE: 175

Val Ile Trp Tyr Asp Gly Ser Asn Lys Tyr Tyr Ala Asp Ser Val Lys
1               5                   10                  15
Gly

<210> SEQ ID NO 176
<211> LENGTH: 11
<212> TYPE: PRT
<213> ORGANISM: Artificial Sequence
<220> FEATURE:
```

<223> OTHER INFORMATION: clone GX119_Variable heavy chain CDR3

<400> SEQUENCE: 176

Asp Arg Ser Trp Asn Tyr Tyr Gly Met Asp Val
1               5                   10

<210> SEQ ID NO 177
<211> LENGTH: 11
<212> TYPE: PRT
<213> ORGANISM: Artificial Sequence
<220> FEATURE:
<223> OTHER INFORMATION: clone GX119_Variable light chain CDR1

<400> SEQUENCE: 177

Arg Ala Ser Gln Ser Ile Ser Ser Tyr Leu Asn
1               5                   10

<210> SEQ ID NO 178
<211> LENGTH: 7
<212> TYPE: PRT
<213> ORGANISM: Artificial Sequence
<220> FEATURE:
<223> OTHER INFORMATION: clone GX119_Variable light chain CDR2

<400> SEQUENCE: 178

Ala Ala Ser Ser Leu Gln Ser
1               5

<210> SEQ ID NO 179
<211> LENGTH: 7
<212> TYPE: PRT
<213> ORGANISM: Artificial Sequence
<220> FEATURE:
<223> OTHER INFORMATION: clone GX119_Variable light chain CDR3

<400> SEQUENCE: 179

Gln Gln Ser Tyr Ser Thr Pro
1               5

<210> SEQ ID NO 180
<211> LENGTH: 8
<212> TYPE: PRT
<213> ORGANISM: Artificial Sequence
<220> FEATURE:
<223> OTHER INFORMATION: clone GX122_Variable heavy chain CDR3

<400> SEQUENCE: 180

Asp Gly Gly Ser Ser Pro Asp Ile
1               5

<210> SEQ ID NO 181
<211> LENGTH: 11
<212> TYPE: PRT
<213> ORGANISM: Artificial Sequence
<220> FEATURE:
<223> OTHER INFORMATION: clone GX122_Variable light chain CDR1

<400> SEQUENCE: 181

Ser Gly Asp Ala Leu Pro Lys Lys Tyr Ala Tyr
1               5                   10

<210> SEQ ID NO 182
<211> LENGTH: 9
<212> TYPE: PRT
<213> ORGANISM: Artificial Sequence
<220> FEATURE:
<223> OTHER INFORMATION: clone GX122_Variable light chain CDR2

```
<400> SEQUENCE: 182

Glu Asp Lys Lys Arg Pro Ser Glu Ile
1               5

<210> SEQ ID NO 183
<211> LENGTH: 9
<212> TYPE: PRT
<213> ORGANISM: Artificial Sequence
<220> FEATURE:
<223> OTHER INFORMATION: clone GX122_Variable light chain CDR3

<400> SEQUENCE: 183

Tyr Ser Ile Asp Arg Ser Gly Ser Arg
1               5

<210> SEQ ID NO 184
<211> LENGTH: 7
<212> TYPE: PRT
<213> ORGANISM: Artificial Sequence
<220> FEATURE:
<223> OTHER INFORMATION: clone GX184_Variable heavy chain CDR1

<400> SEQUENCE: 184

Ser Ser Asn Asn Tyr Trp Gly
1               5

<210> SEQ ID NO 185
<211> LENGTH: 16
<212> TYPE: PRT
<213> ORGANISM: Artificial Sequence
<220> FEATURE:
<223> OTHER INFORMATION: clone GX184_Variable heavy chain CDR2

<400> SEQUENCE: 185

Ser Ile Phe Tyr Ser Gly Ser Thr Tyr Tyr Asn Pro Ser Leu Lys Ser
1               5                   10                  15

<210> SEQ ID NO 186
<211> LENGTH: 12
<212> TYPE: PRT
<213> ORGANISM: Artificial Sequence
<220> FEATURE:
<223> OTHER INFORMATION: clone GX184_Variable heavy chain CDR3

<400> SEQUENCE: 186

Leu Pro Thr Gly Thr Pro Gly Phe Tyr Phe Asp Tyr
1               5                   10

<210> SEQ ID NO 187
<211> LENGTH: 13
<212> TYPE: PRT
<213> ORGANISM: Artificial Sequence
<220> FEATURE:
<223> OTHER INFORMATION: clone GX184_Variable light chain CDR1

<400> SEQUENCE: 187

Thr Gly Asn Ser Asn Asn Val Gly Asn Gln Gly Ala Ala
1               5                   10

<210> SEQ ID NO 188
<211> LENGTH: 9
<212> TYPE: PRT
<213> ORGANISM: Artificial Sequence
<220> FEATURE:
<223> OTHER INFORMATION: clone GX184_Variable light chain CDR3
```

```
<400> SEQUENCE: 188

Ser Ala Trp Asp Ser Ser Leu Ser Ala
1               5

<210> SEQ ID NO 189
<211> LENGTH: 4
<212> TYPE: PRT
<213> ORGANISM: Artificial Sequence
<220> FEATURE:
<223> OTHER INFORMATION: clone GX186_Variable heavy chain CDR3

<400> SEQUENCE: 189

Leu Gln Gly Tyr
1

<210> SEQ ID NO 190
<211> LENGTH: 17
<212> TYPE: PRT
<213> ORGANISM: Artificial Sequence
<220> FEATURE:
<223> OTHER INFORMATION: clone GX186_Variable light chain CDR1

<400> SEQUENCE: 190

Lys Ser Ser Gln Ser Val Leu Tyr Ser Ser Asn Asn Lys Asn Tyr Leu
1               5                   10                  15

Ala

<210> SEQ ID NO 191
<211> LENGTH: 7
<212> TYPE: PRT
<213> ORGANISM: Artificial Sequence
<220> FEATURE:
<223> OTHER INFORMATION: clone GX186_Variable light chain CDR2

<400> SEQUENCE: 191

Trp Ala Ser Thr Arg Glu Ser
1               5

<210> SEQ ID NO 192
<211> LENGTH: 7
<212> TYPE: PRT
<213> ORGANISM: Artificial Sequence
<220> FEATURE:
<223> OTHER INFORMATION: clone GX186_Variable light chain CDR3

<400> SEQUENCE: 192

Gln Gln Tyr Tyr Ser Thr Pro
1               5

<210> SEQ ID NO 193
<211> LENGTH: 13
<212> TYPE: PRT
<213> ORGANISM: Artificial Sequence
<220> FEATURE:
<223> OTHER INFORMATION: clone GX189_Variable light chain CDR1

<400> SEQUENCE: 193

Thr Gly Asn Ser Ser Asn Val Gly Asn Gln Gly Ala Ala
1               5                   10

<210> SEQ ID NO 194
<211> LENGTH: 5
<212> TYPE: PRT
<213> ORGANISM: Artificial Sequence
<220> FEATURE:
<223> OTHER INFORMATION: clone GX196_Variable heavy chain CDR3
```

```
<400> SEQUENCE: 194

Val Thr Gly Asp Tyr
1               5

<210> SEQ ID NO 195
<211> LENGTH: 8
<212> TYPE: PRT
<213> ORGANISM: Artificial Sequence
<220> FEATURE:
<223> OTHER INFORMATION: clone GX197_Variable heavy chain CDR3

<400> SEQUENCE: 195

Gln Gly Ser Gly Trp Leu Asp Tyr
1               5

<210> SEQ ID NO 196
<211> LENGTH: 13
<212> TYPE: PRT
<213> ORGANISM: Artificial Sequence
<220> FEATURE:
<223> OTHER INFORMATION: clone GX197_Variable light chain CDR1

<400> SEQUENCE: 196

Thr Gly Ser Gly Gly Asn Ile Ala Ser Asn Tyr Val Gln
1               5                   10

<210> SEQ ID NO 197
<211> LENGTH: 7
<212> TYPE: PRT
<213> ORGANISM: Artificial Sequence
<220> FEATURE:
<223> OTHER INFORMATION: clone GX197_Variable light chain CDR2

<400> SEQUENCE: 197

Asp Asp Val Gln Arg Pro Ser
1               5

<210> SEQ ID NO 198
<211> LENGTH: 8
<212> TYPE: PRT
<213> ORGANISM: Artificial Sequence
<220> FEATURE:
<223> OTHER INFORMATION: clone GX197_Variable light chain CDR3

<400> SEQUENCE: 198

Gln Ser Tyr Asp Arg Thr Tyr Arg
1               5

<210> SEQ ID NO 199
<211> LENGTH: 5
<212> TYPE: PRT
<213> ORGANISM: Artificial Sequence
<220> FEATURE:
<223> OTHER INFORMATION: clone GX201_Variable heavy chain CDR1

<400> SEQUENCE: 199

Asn Tyr Gly Met Asn
1               5

<210> SEQ ID NO 200
<211> LENGTH: 17
<212> TYPE: PRT
<213> ORGANISM: Artificial Sequence
<220> FEATURE:
<223> OTHER INFORMATION: clone GX201_Variable heavy chain CDR2
```

-continued

```
<400> SEQUENCE: 200

Ser Ile Ser Thr Arg Ser Gly Tyr Ile Phe Tyr Ala Asp Ser Val Lys
1               5                   10                  15

Gly

<210> SEQ ID NO 201
<211> LENGTH: 10
<212> TYPE: PRT
<213> ORGANISM: Artificial Sequence
<220> FEATURE:
<223> OTHER INFORMATION: clone GX201_Variable heavy chain CDR3

<400> SEQUENCE: 201

Asp Arg Pro Asn Arg Ser Gly Met Asp Val
1               5                   10

<210> SEQ ID NO 202
<211> LENGTH: 14
<212> TYPE: PRT
<213> ORGANISM: Artificial Sequence
<220> FEATURE:
<223> OTHER INFORMATION: clone GX201_Variable light chain CDR1

<400> SEQUENCE: 202

Thr Gly Thr Ser Ser Asp Val Gly Gly Tyr Asn Tyr Val Ser
1               5                   10

<210> SEQ ID NO 203
<211> LENGTH: 7
<212> TYPE: PRT
<213> ORGANISM: Artificial Sequence
<220> FEATURE:
<223> OTHER INFORMATION: clone GX201_Variable light chain CDR2

<400> SEQUENCE: 203

Asp Val Ser Asn Arg Pro Ser
1               5

<210> SEQ ID NO 204
<211> LENGTH: 8
<212> TYPE: PRT
<213> ORGANISM: Artificial Sequence
<220> FEATURE:
<223> OTHER INFORMATION: clone GX201_Variable light chain CDR3

<400> SEQUENCE: 204

Ser Ser Tyr Thr Ser Ser Asp Thr
1               5

<210> SEQ ID NO 205
<211> LENGTH: 5
<212> TYPE: PRT
<213> ORGANISM: Artificial Sequence
<220> FEATURE:
<223> OTHER INFORMATION: clone GX205_Variable heavy chain CDR3

<400> SEQUENCE: 205

Val Leu Leu Asp Tyr
1               5

<210> SEQ ID NO 206
<211> LENGTH: 8
<212> TYPE: PRT
<213> ORGANISM: Artificial Sequence
<220> FEATURE:
<223> OTHER INFORMATION: clone GX205_Variable light chain CDR3
```

```
<400> SEQUENCE: 206

Gln Gln Tyr Asp Asn Leu Leu Ala
1               5

<210> SEQ ID NO 207
<211> LENGTH: 13
<212> TYPE: PRT
<213> ORGANISM: Artificial Sequence
<220> FEATURE:
<223> OTHER INFORMATION: clone GX206_Variable heavy chain CDR3

<400> SEQUENCE: 207

Leu Gly Asp Tyr Gly Gly Asn Gly Tyr Tyr Phe Asp Tyr
1               5                   10

<210> SEQ ID NO 208
<211> LENGTH: 13
<212> TYPE: PRT
<213> ORGANISM: Artificial Sequence
<220> FEATURE:
<223> OTHER INFORMATION: clone GX206_Variable light chain CDR1

<400> SEQUENCE: 208

Ser Gly Ser Ser Ser Asn Ile Gly Lys Asn Gly Val Ser
1               5                   10

<210> SEQ ID NO 209
<211> LENGTH: 7
<212> TYPE: PRT
<213> ORGANISM: Artificial Sequence
<220> FEATURE:
<223> OTHER INFORMATION: clone GX206_Variable light chain CDR2

<400> SEQUENCE: 209

Glu Asn Asn Arg Arg Pro Ser
1               5

<210> SEQ ID NO 210
<211> LENGTH: 14
<212> TYPE: PRT
<213> ORGANISM: Artificial Sequence
<220> FEATURE:
<223> OTHER INFORMATION: clone GX207_Variable heavy chain CDR3

<400> SEQUENCE: 210

Glu Gly Ile Ala Ala Ala Gly Tyr Tyr Tyr Gly Met Asp Val
1               5                   10

<210> SEQ ID NO 211
<211> LENGTH: 14
<212> TYPE: PRT
<213> ORGANISM: Artificial Sequence
<220> FEATURE:
<223> OTHER INFORMATION: clone GX207_Variable light chain CDR1

<400> SEQUENCE: 211

Thr Gly Thr Ser Ser Asp Val Gly Gly Tyr Asn Arg Val Ser
1               5                   10

<210> SEQ ID NO 212
<211> LENGTH: 7
<212> TYPE: PRT
<213> ORGANISM: Artificial Sequence
<220> FEATURE:
<223> OTHER INFORMATION: clone GX207_Variable light chain CDR2
```

<400> SEQUENCE: 212

Glu Val Ser Asn Arg Pro Ser
1               5

<210> SEQ ID NO 213
<211> LENGTH: 9
<212> TYPE: PRT
<213> ORGANISM: Artificial Sequence
<220> FEATURE:
<223> OTHER INFORMATION: clone GX207_Variable light chain CDR3

<400> SEQUENCE: 213

Ser Ser Tyr Thr Ser Ser Thr Thr Tyr
1               5

<210> SEQ ID NO 214
<211> LENGTH: 8
<212> TYPE: PRT
<213> ORGANISM: Artificial Sequence
<220> FEATURE:
<223> OTHER INFORMATION: clone GX209_Variable heavy chain CDR3

<400> SEQUENCE: 214

Gly Tyr Tyr Tyr Gly Met Asp Val
1               5

<210> SEQ ID NO 215
<211> LENGTH: 11
<212> TYPE: PRT
<213> ORGANISM: Artificial Sequence
<220> FEATURE:
<223> OTHER INFORMATION: clone GX209_Variable light chain CDR1

<400> SEQUENCE: 215

Ser Gly Asp Lys Leu Gly Asp Lys Tyr Val Phe
1               5                   10

<210> SEQ ID NO 216
<211> LENGTH: 7
<212> TYPE: PRT
<213> ORGANISM: Artificial Sequence
<220> FEATURE:
<223> OTHER INFORMATION: clone GX209_Variable light chain CDR2

<400> SEQUENCE: 216

Gln Asp Asn Lys Arg Pro Ser
1               5

<210> SEQ ID NO 217
<211> LENGTH: 7
<212> TYPE: PRT
<213> ORGANISM: Artificial Sequence
<220> FEATURE:
<223> OTHER INFORMATION: clone GX209_Variable light chain CDR3

<400> SEQUENCE: 217

Gln Thr Trp Asp Ser Ser Thr
1               5

<210> SEQ ID NO 218
<211> LENGTH: 10
<212> TYPE: PRT
<213> ORGANISM: Artificial Sequence
<220> FEATURE:
<223> OTHER INFORMATION: clone GX213_Variable heavy chain CDR3

<400> SEQUENCE: 218

```
Leu Phe Trp Gln Gln Leu Thr Phe Asp Tyr
1               5                   10

<210> SEQ ID NO 219
<211> LENGTH: 13
<212> TYPE: PRT
<213> ORGANISM: Artificial Sequence
<220> FEATURE:
<223> OTHER INFORMATION: clone GX213_Variable light chain CDR1

<400> SEQUENCE: 219

Ser Gly Ser Ser Ser Asn Ile Gly Lys Asn His Val Ile
1               5                   10

<210> SEQ ID NO 220
<211> LENGTH: 7
<212> TYPE: PRT
<213> ORGANISM: Artificial Sequence
<220> FEATURE:
<223> OTHER INFORMATION: clone GX213_Variable light chain CDR2

<400> SEQUENCE: 220

Glu Asn Asn Lys Arg Pro Ser
1               5

<210> SEQ ID NO 221
<211> LENGTH: 9
<212> TYPE: PRT
<213> ORGANISM: Artificial Sequence
<220> FEATURE:
<223> OTHER INFORMATION: clone GX213_Variable light chain CDR3

<400> SEQUENCE: 221

Gly Thr Trp Asp Asn Ser Leu Ser Ala
1               5

<210> SEQ ID NO 222
<211> LENGTH: 4
<212> TYPE: PRT
<213> ORGANISM: Artificial Sequence
<220> FEATURE:
<223> OTHER INFORMATION: clone GX214_Variable heavy chain CDR3

<400> SEQUENCE: 222

Leu Tyr Asp Phe
1

<210> SEQ ID NO 223
<211> LENGTH: 11
<212> TYPE: PRT
<213> ORGANISM: Artificial Sequence
<220> FEATURE:
<223> OTHER INFORMATION: clone GX214_Variable light chain CDR1

<400> SEQUENCE: 223

Gln Ala Ser Gln Asp Ile Thr Asn Phe Leu Asn
1               5                   10

<210> SEQ ID NO 224
<211> LENGTH: 11
<212> TYPE: PRT
<213> ORGANISM: Artificial Sequence
<220> FEATURE:
<223> OTHER INFORMATION: clone GX216_Variable light chain CDR1

<400> SEQUENCE: 224
```

Arg Ala Ser Gln Ser Val Ser Ser Tyr Leu Ala
1               5                   10

<210> SEQ ID NO 225
<211> LENGTH: 7
<212> TYPE: PRT
<213> ORGANISM: Artificial Sequence
<220> FEATURE:
<223> OTHER INFORMATION: clone GX216_Variable light chain CDR2

<400> SEQUENCE: 225

Asp Ala Ser Asn Arg Ala Thr
1               5

<210> SEQ ID NO 226
<211> LENGTH: 10
<212> TYPE: PRT
<213> ORGANISM: Artificial Sequence
<220> FEATURE:
<223> OTHER INFORMATION: clone GX216_Variable light chain CDR3

<400> SEQUENCE: 226

Gln Gln Arg Ser Asn Trp Pro Pro Val Ala
1               5                   10

<210> SEQ ID NO 227
<211> LENGTH: 7
<212> TYPE: PRT
<213> ORGANISM: Artificial Sequence
<220> FEATURE:
<223> OTHER INFORMATION: clone GX217_Variable heavy chain CDR3

<400> SEQUENCE: 227

Val Ser Gly Asp Pro Lys Asp
1               5

<210> SEQ ID NO 228
<211> LENGTH: 11
<212> TYPE: PRT
<213> ORGANISM: Artificial Sequence
<220> FEATURE:
<223> OTHER INFORMATION: clone GX217_Variable light chain CDR1

<400> SEQUENCE: 228

Arg Ala Ser Gln Ser Val Ser Ser Asn Leu Ala
1               5                   10

<210> SEQ ID NO 229
<211> LENGTH: 7
<212> TYPE: PRT
<213> ORGANISM: Artificial Sequence
<220> FEATURE:
<223> OTHER INFORMATION: clone GX217_Variable light chain CDR2

<400> SEQUENCE: 229

Gly Ala Ser Thr Arg Ala Thr
1               5

<210> SEQ ID NO 230
<211> LENGTH: 8
<212> TYPE: PRT
<213> ORGANISM: Artificial Sequence
<220> FEATURE:
<223> OTHER INFORMATION: clone GX217_Variable light chain CDR3

<400> SEQUENCE: 230

Gln Gln Tyr Asn Asn Trp Pro Arg

```
<210> SEQ ID NO 231
<211> LENGTH: 17
<212> TYPE: PRT
<213> ORGANISM: Artificial Sequence
<220> FEATURE:
<223> OTHER INFORMATION: clone GX219_Variable heavy chain CDR2

<400> SEQUENCE: 231

Arg Ile Asn Pro Asn Ser Gly Gly Thr Asn Tyr Ala Gln Lys Phe Gln
1               5                   10                  15
Gly

<210> SEQ ID NO 232
<211> LENGTH: 17
<212> TYPE: PRT
<213> ORGANISM: Artificial Sequence
<220> FEATURE:
<223> OTHER INFORMATION: clone GX219_Variable heavy chain CDR3

<400> SEQUENCE: 232

Val Ala Arg Tyr Cys Ser Ser Thr Ser Cys Arg Thr Gly Gly Met Asp
1               5                   10                  15
Val

<210> SEQ ID NO 233
<211> LENGTH: 13
<212> TYPE: PRT
<213> ORGANISM: Artificial Sequence
<220> FEATURE:
<223> OTHER INFORMATION: clone GX219_Variable light chain CDR1

<400> SEQUENCE: 233

Ser Gly Arg Ser Ser Asn Ile Gly Ser Arg Tyr Val Tyr
1               5                   10

<210> SEQ ID NO 234
<211> LENGTH: 7
<212> TYPE: PRT
<213> ORGANISM: Artificial Sequence
<220> FEATURE:
<223> OTHER INFORMATION: clone GX219_Variable light chain CDR2

<400> SEQUENCE: 234

Arg Asn Asp Gln Arg Pro Ser
1               5

<210> SEQ ID NO 235
<211> LENGTH: 9
<212> TYPE: PRT
<213> ORGANISM: Artificial Sequence
<220> FEATURE:
<223> OTHER INFORMATION: clone GX219_Variable light chain CDR3

<400> SEQUENCE: 235

Ala Thr Trp Asp Asp Ser Leu Ser Ala
1               5

<210> SEQ ID NO 236
<211> LENGTH: 7
<212> TYPE: PRT
<213> ORGANISM: Artificial Sequence
<220> FEATURE:
<223> OTHER INFORMATION: clone GX221_Variable light chain CDR2
```

```
<400> SEQUENCE: 236

Arg Asn Asn Lys Arg Pro Ser
1               5

<210> SEQ ID NO 237
<211> LENGTH: 5
<212> TYPE: PRT
<213> ORGANISM: Artificial Sequence
<220> FEATURE:
<223> OTHER INFORMATION: clone GX222_Variable heavy chain CDR3

<400> SEQUENCE: 237

Val Thr Leu Asp Tyr
1               5

<210> SEQ ID NO 238
<211> LENGTH: 7
<212> TYPE: PRT
<213> ORGANISM: Artificial Sequence
<220> FEATURE:
<223> OTHER INFORMATION: clone GX222_Variable light chain CDR3

<400> SEQUENCE: 238

Gln Gln Tyr Asp Ser Leu Pro
1               5

<210> SEQ ID NO 239
<211> LENGTH: 10
<212> TYPE: PRT
<213> ORGANISM: Artificial Sequence
<220> FEATURE:
<223> OTHER INFORMATION: clone GX224_Variable heavy chain CDR3

<400> SEQUENCE: 239

Ser Arg Pro Arg Ser Ser Ser Phe Asp Tyr
1               5                   10

<210> SEQ ID NO 240
<211> LENGTH: 13
<212> TYPE: PRT
<213> ORGANISM: Artificial Sequence
<220> FEATURE:
<223> OTHER INFORMATION: clone GX224_Variable light chain CDR1

<400> SEQUENCE: 240

Thr Val Ser Ser Gly Ser Ile Ala Lys Asn Tyr Val His
1               5                   10

<210> SEQ ID NO 241
<211> LENGTH: 7
<212> TYPE: PRT
<213> ORGANISM: Artificial Sequence
<220> FEATURE:
<223> OTHER INFORMATION: clone GX224_Variable light chain CDR2

<400> SEQUENCE: 241

Glu Asp Asn Arg Arg Pro Ser
1               5

<210> SEQ ID NO 242
<211> LENGTH: 9
<212> TYPE: PRT
<213> ORGANISM: Artificial Sequence
<220> FEATURE:
<223> OTHER INFORMATION: clone GX224_Variable light chain CDR3

<400> SEQUENCE: 242
```

```
Gln Ser Tyr Asp Asp Ser Gly Asp Arg
1               5

<210> SEQ ID NO 243
<211> LENGTH: 10
<212> TYPE: PRT
<213> ORGANISM: Artificial Sequence
<220> FEATURE:
<223> OTHER INFORMATION: clone GX225_Variable heavy chain CDR3

<400> SEQUENCE: 243

Glu Ser Gly Pro Ser Gly Gly Met Asp Val
1               5                   10

<210> SEQ ID NO 244
<211> LENGTH: 11
<212> TYPE: PRT
<213> ORGANISM: Artificial Sequence
<220> FEATURE:
<223> OTHER INFORMATION: clone GX225_Variable light chain CDR1

<400> SEQUENCE: 244

Ser Gly Asp Ala Leu Pro Lys Gln Tyr Ala Tyr
1               5                   10

<210> SEQ ID NO 245
<211> LENGTH: 7
<212> TYPE: PRT
<213> ORGANISM: Artificial Sequence
<220> FEATURE:
<223> OTHER INFORMATION: clone GX225_Variable light chain CDR2

<400> SEQUENCE: 245

Lys Asp Ser Glu Arg Pro Ser
1               5

<210> SEQ ID NO 246
<211> LENGTH: 9
<212> TYPE: PRT
<213> ORGANISM: Artificial Sequence
<220> FEATURE:
<223> OTHER INFORMATION: clone GX225_Variable light chain CDR3

<400> SEQUENCE: 246

Ser Ser Tyr Thr Ser Ser Ser Thr Arg
1               5

<210> SEQ ID NO 247
<211> LENGTH: 5
<212> TYPE: PRT
<213> ORGANISM: Artificial Sequence
<220> FEATURE:
<223> OTHER INFORMATION: clone GX229_Variable heavy chain CDR3

<400> SEQUENCE: 247

Val Leu Leu Asp Tyr
1               5

<210> SEQ ID NO 248
<211> LENGTH: 7
<212> TYPE: PRT
<213> ORGANISM: Artificial Sequence
<220> FEATURE:
<223> OTHER INFORMATION: clone GX229_Variable light chain CDR3

<400> SEQUENCE: 248
```

```
Gln Gln Tyr Asp Asn Leu Trp
1               5

<210> SEQ ID NO 249
<211> LENGTH: 7
<212> TYPE: PRT
<213> ORGANISM: Artificial Sequence
<220> FEATURE:
<223> OTHER INFORMATION: clone GX233_Variable light chain CDR3

<400> SEQUENCE: 249

Met Glu Val Arg Tyr Trp Pro
1               5

<210> SEQ ID NO 250
<211> LENGTH: 20
<212> TYPE: PRT
<213> ORGANISM: Artificial Sequence
<220> FEATURE:
<223> OTHER INFORMATION: clone GX234_Variable heavy chain CDR3

<400> SEQUENCE: 250

Val Gly Leu Gly Asp Phe Trp Ser Gly Asp Tyr Tyr Tyr Tyr Tyr
1               5                   10                  15

Gly Met Asp Val
            20

<210> SEQ ID NO 251
<211> LENGTH: 11
<212> TYPE: PRT
<213> ORGANISM: Artificial Sequence
<220> FEATURE:
<223> OTHER INFORMATION: clone GX234_Variable light chain CDR1

<400> SEQUENCE: 251

Gln Gly Asp Ser Leu Arg Ser Ser Tyr Ala Ser
1               5                   10

<210> SEQ ID NO 252
<211> LENGTH: 7
<212> TYPE: PRT
<213> ORGANISM: Artificial Sequence
<220> FEATURE:
<223> OTHER INFORMATION: clone GX234_Variable light chain CDR2

<400> SEQUENCE: 252

Gly Lys Asn Asn Arg Pro Ser
1               5

<210> SEQ ID NO 253
<211> LENGTH: 11
<212> TYPE: PRT
<213> ORGANISM: Artificial Sequence
<220> FEATURE:
<223> OTHER INFORMATION: clone GX234_Variable light chain CDR3

<400> SEQUENCE: 253

His Ser Arg Asp Ser Thr Gly Ser His Pro Asn
1               5                   10

<210> SEQ ID NO 254
<211> LENGTH: 8
<212> TYPE: PRT
<213> ORGANISM: Artificial Sequence
<220> FEATURE:
<223> OTHER INFORMATION: clone GX242_Variable heavy chain CDR3
```

```
<400> SEQUENCE: 254

Val Val Ala Ala Arg Glu Asp Tyr
1               5

<210> SEQ ID NO 255
<211> LENGTH: 11
<212> TYPE: PRT
<213> ORGANISM: Artificial Sequence
<220> FEATURE:
<223> OTHER INFORMATION: clone GX242_Variable light chain CDR1

<400> SEQUENCE: 255

Arg Ala Thr Gln Ser Val Gly Ser Tyr Leu Ala
1               5                   10

<210> SEQ ID NO 256
<211> LENGTH: 7
<212> TYPE: PRT
<213> ORGANISM: Artificial Sequence
<220> FEATURE:
<223> OTHER INFORMATION: clone GX242_Variable light chain CDR2

<400> SEQUENCE: 256

Asp Ala Phe Asn Arg Ala Thr
1               5

<210> SEQ ID NO 257
<211> LENGTH: 7
<212> TYPE: PRT
<213> ORGANISM: Artificial Sequence
<220> FEATURE:
<223> OTHER INFORMATION: clone GX242_Variable light chain CDR3

<400> SEQUENCE: 257

Gln Gln Arg Ser Asn Trp Pro
1               5

<210> SEQ ID NO 258
<211> LENGTH: 7
<212> TYPE: PRT
<213> ORGANISM: Artificial Sequence
<220> FEATURE:
<223> OTHER INFORMATION: clone GX245_Variable heavy chain CDR3

<400> SEQUENCE: 258

Val Ser Asp Asp Ser Pro Tyr
1               5

<210> SEQ ID NO 259
<211> LENGTH: 15
<212> TYPE: PRT
<213> ORGANISM: Artificial Sequence
<220> FEATURE:
<223> OTHER INFORMATION: clone GX247_Variable heavy chain CDR3

<400> SEQUENCE: 259

Thr Arg Lys Gly Ser Gly Tyr Ser Tyr Gly Tyr Gly Met Asp Val
1               5                   10                  15

<210> SEQ ID NO 260
<211> LENGTH: 11
<212> TYPE: PRT
<213> ORGANISM: Artificial Sequence
<220> FEATURE:
<223> OTHER INFORMATION: clone GX247_Variable light chain CDR1

<400> SEQUENCE: 260
```

```
Ser Gly Asp Lys Leu Gly Asn Lys Tyr Val Ser
1               5                   10

<210> SEQ ID NO 261
<211> LENGTH: 6
<212> TYPE: PRT
<213> ORGANISM: Artificial Sequence
<220> FEATURE:
<223> OTHER INFORMATION: clone GX247_Variable light chain CDR3

<400> SEQUENCE: 261

Gln Thr Trp Asp Ser Ser
1               5

<210> SEQ ID NO 262
<211> LENGTH: 5
<212> TYPE: PRT
<213> ORGANISM: Artificial Sequence
<220> FEATURE:
<223> OTHER INFORMATION: clone GX248_Variable heavy chain CDR1

<400> SEQUENCE: 262

Ser Tyr Ala Ile Ser
1               5

<210> SEQ ID NO 263
<211> LENGTH: 17
<212> TYPE: PRT
<213> ORGANISM: Artificial Sequence
<220> FEATURE:
<223> OTHER INFORMATION: clone GX248_Variable heavy chain CDR2

<400> SEQUENCE: 263

Gly Ile Ile Pro Ile Phe Gly Thr Ala Asn Tyr Ala Gln Lys Phe Gln
1               5                   10                  15

Gly

<210> SEQ ID NO 264
<211> LENGTH: 13
<212> TYPE: PRT
<213> ORGANISM: Artificial Sequence
<220> FEATURE:
<223> OTHER INFORMATION: clone GX248_Variable heavy chain CDR3

<400> SEQUENCE: 264

Val Arg Gly Thr Gly Pro Arg Gly Gly Thr Phe Asp Tyr
1               5                   10

<210> SEQ ID NO 265
<211> LENGTH: 13
<212> TYPE: PRT
<213> ORGANISM: Artificial Sequence
<220> FEATURE:
<223> OTHER INFORMATION: clone GX248_Variable light chain CDR1

<400> SEQUENCE: 265

Ser Gly Ser Ser Ser Asn Ile Gly Asn Asn Tyr Val Ser
1               5                   10

<210> SEQ ID NO 266
<211> LENGTH: 17
<212> TYPE: PRT
<213> ORGANISM: Artificial Sequence
<220> FEATURE:
<223> OTHER INFORMATION: clone GX253_Variable heavy chain CDR2
```

```
<400> SEQUENCE: 266

Tyr Ile Ser Ser Ser Gly Thr Thr Ile Tyr Tyr Ala Asp Ser Val Lys
1               5                   10                  15

Gly

<210> SEQ ID NO 267
<211> LENGTH: 7
<212> TYPE: PRT
<213> ORGANISM: Artificial Sequence
<220> FEATURE:
<223> OTHER INFORMATION: clone GX253_Variable heavy chain CDR3

<400> SEQUENCE: 267

Val Arg Asp Ser Ser Gly Phe
1               5

<210> SEQ ID NO 268
<211> LENGTH: 4
<212> TYPE: PRT
<213> ORGANISM: Artificial Sequence
<220> FEATURE:
<223> OTHER INFORMATION: clone GX259_Variable heavy chain CDR1

<400> SEQUENCE: 268

Asn Tyr Trp Ile
1

<210> SEQ ID NO 269
<211> LENGTH: 17
<212> TYPE: PRT
<213> ORGANISM: Artificial Sequence
<220> FEATURE:
<223> OTHER INFORMATION: clone GX259_Variable heavy chain CDR2

<400> SEQUENCE: 269

Ile Ile Tyr Pro Gly Asp Ser Asp Thr Arg Tyr Ser Pro Ser Leu Gln
1               5                   10                  15

Gly

<210> SEQ ID NO 270
<211> LENGTH: 7
<212> TYPE: PRT
<213> ORGANISM: Artificial Sequence
<220> FEATURE:
<223> OTHER INFORMATION: clone GX259_Variable heavy chain CDR3

<400> SEQUENCE: 270

Ile Gly Leu Arg Glu Gly Arg
1               5

<210> SEQ ID NO 271
<211> LENGTH: 11
<212> TYPE: PRT
<213> ORGANISM: Artificial Sequence
<220> FEATURE:
<223> OTHER INFORMATION: clone GX259_Variable light chain CDR1

<400> SEQUENCE: 271

Arg Ala Ser Gln Gly Ile Ser Asn Tyr Leu Ala
1               5                   10

<210> SEQ ID NO 272
<211> LENGTH: 5
<212> TYPE: PRT
<213> ORGANISM: Artificial Sequence
```

```
<220> FEATURE:
<223> OTHER INFORMATION: clone GX259_Variable light chain CDR3

<400> SEQUENCE: 272

Gln Gln Tyr Asp Asn
1               5

<210> SEQ ID NO 273
<211> LENGTH: 5
<212> TYPE: PRT
<213> ORGANISM: Artificial Sequence
<220> FEATURE:
<223> OTHER INFORMATION: clone GX263_Variable heavy chain CDR1

<400> SEQUENCE: 273

Ser Tyr Ser Met Asn
1               5

<210> SEQ ID NO 274
<211> LENGTH: 17
<212> TYPE: PRT
<213> ORGANISM: Artificial Sequence
<220> FEATURE:
<223> OTHER INFORMATION: clone GX263_Variable heavy chain CDR2

<400> SEQUENCE: 274

Ser Ile Ser Ser Ser Ser Ser Tyr Ile Tyr Tyr Ala Asp Ser Val Lys
1               5                   10                  15

Gly

<210> SEQ ID NO 275
<211> LENGTH: 11
<212> TYPE: PRT
<213> ORGANISM: Artificial Sequence
<220> FEATURE:
<223> OTHER INFORMATION: clone GX263_Variable heavy chain CDR3

<400> SEQUENCE: 275

Val Thr Pro Tyr Tyr Tyr Tyr Gly Met Asp Val
1               5                   10

<210> SEQ ID NO 276
<211> LENGTH: 7
<212> TYPE: PRT
<213> ORGANISM: Artificial Sequence
<220> FEATURE:
<223> OTHER INFORMATION: clone GX263_Variable light chain CDR2

<400> SEQUENCE: 276

Asp Ser Asn Lys Arg Pro Pro
1               5

<210> SEQ ID NO 277
<211> LENGTH: 9
<212> TYPE: PRT
<213> ORGANISM: Artificial Sequence
<220> FEATURE:
<223> OTHER INFORMATION: clone GX263_Variable light chain CDR3

<400> SEQUENCE: 277

Gly Ala Trp Asp Ser Ser Leu Ser Ala
1               5

<210> SEQ ID NO 278
<211> LENGTH: 19
<212> TYPE: PRT
```

```
<213> ORGANISM: Artificial Sequence
<220> FEATURE:
<223> OTHER INFORMATION: clone GX264_Variable heavy chain CDR3

<400> SEQUENCE: 278

Leu Arg Trp Tyr Ser Tyr Gly Tyr Phe Asp Val Arg Gly Gly Tyr Tyr
1               5                   10                  15
Phe Asp Tyr

<210> SEQ ID NO 279
<211> LENGTH: 5
<212> TYPE: PRT
<213> ORGANISM: Artificial Sequence
<220> FEATURE:
<223> OTHER INFORMATION: clone GX265_Variable heavy chain CDR3

<400> SEQUENCE: 279

Val His Leu Asp Tyr
1               5

<210> SEQ ID NO 280
<211> LENGTH: 6
<212> TYPE: PRT
<213> ORGANISM: Artificial Sequence
<220> FEATURE:
<223> OTHER INFORMATION: clone GX268_Variable light chain CDR3

<400> SEQUENCE: 280

Gln Gln Ser Tyr Ser Thr
1               5

<210> SEQ ID NO 281
<211> LENGTH: 5
<212> TYPE: PRT
<213> ORGANISM: Artificial Sequence
<220> FEATURE:
<223> OTHER INFORMATION: clone GX270_Variable heavy chain CDR1

<400> SEQUENCE: 281

Ser Ser Tyr Met His
1               5

<210> SEQ ID NO 282
<211> LENGTH: 17
<212> TYPE: PRT
<213> ORGANISM: Artificial Sequence
<220> FEATURE:
<223> OTHER INFORMATION: clone GX270_Variable heavy chain CDR2

<400> SEQUENCE: 282

Ile Ile Asn Pro Asn Ser Arg Gly Thr Asn Tyr Ala Gln Lys Phe Gln
1               5                   10                  15
Gly

<210> SEQ ID NO 283
<211> LENGTH: 8
<212> TYPE: PRT
<213> ORGANISM: Artificial Sequence
<220> FEATURE:
<223> OTHER INFORMATION: clone GX270_Variable heavy chain CDR3

<400> SEQUENCE: 283

Ser Ser Gly Asp Tyr Pro Asp Tyr
1               5
```

```
<210> SEQ ID NO 284
<211> LENGTH: 8
<212> TYPE: PRT
<213> ORGANISM: Artificial Sequence
<220> FEATURE:
<223> OTHER INFORMATION: clone GX270_Variable light chain CDR2

<400> SEQUENCE: 284

Tyr Glu Asp Lys Lys Arg Pro Ala
1               5

<210> SEQ ID NO 285
<211> LENGTH: 5
<212> TYPE: PRT
<213> ORGANISM: Artificial Sequence
<220> FEATURE:
<223> OTHER INFORMATION: clone GS001_Variable heavy chain CDR1

<400> SEQUENCE: 285

Ser Tyr Ser Met Ser
1               5

<210> SEQ ID NO 286
<211> LENGTH: 17
<212> TYPE: PRT
<213> ORGANISM: Artificial Sequence
<220> FEATURE:
<223> OTHER INFORMATION: clone GS001_Variable heavy chain CDR2

<400> SEQUENCE: 286

Gly Ile Ser Pro Ser Gly Gly Asn Lys Tyr Tyr Ala Asp Ser Val Lys
1               5                   10                  15

Gly

<210> SEQ ID NO 287
<211> LENGTH: 16
<212> TYPE: PRT
<213> ORGANISM: Artificial Sequence
<220> FEATURE:
<223> OTHER INFORMATION: clone GS001_Variable heavy chain CDR3

<400> SEQUENCE: 287

Ala Leu Leu Gly Cys Lys Ser Ala Tyr Cys Tyr Tyr Ala Met Asp Val
1               5                   10                  15

<210> SEQ ID NO 288
<211> LENGTH: 13
<212> TYPE: PRT
<213> ORGANISM: Artificial Sequence
<220> FEATURE:
<223> OTHER INFORMATION: clone GS001_Variable light chain CDR1

<400> SEQUENCE: 288

Thr Gly Ser Ser Ser Asn Ile Gly Ser Asn Ala Val Asn
1               5                   10

<210> SEQ ID NO 289
<211> LENGTH: 7
<212> TYPE: PRT
<213> ORGANISM: Artificial Sequence
<220> FEATURE:
<223> OTHER INFORMATION: clone GS001_Variable light chain CDR2

<400> SEQUENCE: 289

Ala Asp Ser Lys Arg Pro Ser
1               5
```

<210> SEQ ID NO 290
<211> LENGTH: 9
<212> TYPE: PRT
<213> ORGANISM: Artificial Sequence
<220> FEATURE:
<223> OTHER INFORMATION: clone GS001_Variable light chain CDR3

<400> SEQUENCE: 290

Gly Ser Trp Asp Ser Ser Leu Ser Gly
1               5

<210> SEQ ID NO 291
<211> LENGTH: 5
<212> TYPE: PRT
<213> ORGANISM: Artificial Sequence
<220> FEATURE:
<223> OTHER INFORMATION: clone GS002_Variable heavy chain CDR1

<400> SEQUENCE: 291

Gly Tyr Ser Met Ser
1               5

<210> SEQ ID NO 292
<211> LENGTH: 17
<212> TYPE: PRT
<213> ORGANISM: Artificial Sequence
<220> FEATURE:
<223> OTHER INFORMATION: clone GS002_Variable heavy chain CDR2

<400> SEQUENCE: 292

Ser Ile Ser Pro Gly Gly Ser Ser Thr Tyr Tyr Ala Asp Ser Val Lys
1               5                   10                  15

Gly

<210> SEQ ID NO 293
<211> LENGTH: 18
<212> TYPE: PRT
<213> ORGANISM: Artificial Sequence
<220> FEATURE:
<223> OTHER INFORMATION: clone GS002_Variable heavy chain CDR3

<400> SEQUENCE: 293

Tyr Arg Val Trp His Met Thr Thr Gly Asp Tyr Tyr Ser Asn Ala Met
1               5                   10                  15

Asp Val

<210> SEQ ID NO 294
<211> LENGTH: 13
<212> TYPE: PRT
<213> ORGANISM: Artificial Sequence
<220> FEATURE:
<223> OTHER INFORMATION: clone GS002_Variable light chain CDR1

<400> SEQUENCE: 294

Thr Gly Ser Ser Ser Asn Ile Gly Ser Asn Ala Val Ser
1               5                   10

<210> SEQ ID NO 295
<211> LENGTH: 7
<212> TYPE: PRT
<213> ORGANISM: Artificial Sequence
<220> FEATURE:
<223> OTHER INFORMATION: clone GS002_Variable light chain CDR2

<400> SEQUENCE: 295

Asp Asp Asn Lys Arg Pro Ser
1               5

<210> SEQ ID NO 296
<211> LENGTH: 9
<212> TYPE: PRT
<213> ORGANISM: Artificial Sequence
<220> FEATURE:
<223> OTHER INFORMATION: clone GS002_Variable light chain CDR3

<400> SEQUENCE: 296

Gly Thr Trp Asp Asp Ser Leu Ser Gly
1               5

<210> SEQ ID NO 297
<211> LENGTH: 5
<212> TYPE: PRT
<213> ORGANISM: Artificial Sequence
<220> FEATURE:
<223> OTHER INFORMATION: clone GS003_Variable heavy chain CDR1

<400> SEQUENCE: 297

Asn Tyr Ser Met Ser
1               5

<210> SEQ ID NO 298
<211> LENGTH: 17
<212> TYPE: PRT
<213> ORGANISM: Artificial Sequence
<220> FEATURE:
<223> OTHER INFORMATION: clone GS003_Variable heavy chain CDR2

<400> SEQUENCE: 298

Val Ile Ser Pro Gly Ser Gly Ser Thr Tyr Tyr Ala Asp Ser Val Lys
1               5                   10                  15

Gly

<210> SEQ ID NO 299
<211> LENGTH: 18
<212> TYPE: PRT
<213> ORGANISM: Artificial Sequence
<220> FEATURE:
<223> OTHER INFORMATION: clone GS003_Variable heavy chain CDR3

<400> SEQUENCE: 299

Tyr Arg Val Met Arg Ser Pro His Asn Pro Tyr Tyr Ser Tyr Gly Met
1               5                   10                  15

Asp Val

<210> SEQ ID NO 300
<211> LENGTH: 13
<212> TYPE: PRT
<213> ORGANISM: Artificial Sequence
<220> FEATURE:
<223> OTHER INFORMATION: clone GS003_Variable light chain CDR1

<400> SEQUENCE: 300

Ser Gly Ser Ser Ser Asn Ile Gly Ser Asn Asp Val Asn
1               5                   10

<210> SEQ ID NO 301
<211> LENGTH: 7
<212> TYPE: PRT
<213> ORGANISM: Artificial Sequence
<220> FEATURE:
<223> OTHER INFORMATION: clone GS003_Variable light chain CDR2

```
<400> SEQUENCE: 301

Ser Asn Ser Gln Arg Pro Ser
1               5

<210> SEQ ID NO 302
<211> LENGTH: 9
<212> TYPE: PRT
<213> ORGANISM: Artificial Sequence
<220> FEATURE:
<223> OTHER INFORMATION: clone GS003_Variable light chain CDR3

<400> SEQUENCE: 302

Gly Ser Trp Asp Ala Ser Leu Ser Gly
1               5

<210> SEQ ID NO 303
<211> LENGTH: 17
<212> TYPE: PRT
<213> ORGANISM: Artificial Sequence
<220> FEATURE:
<223> OTHER INFORMATION: clone GS004_Variable heavy chain CDR2

<400> SEQUENCE: 303

Ala Ile Ser Pro Gly Ser Ser Asn Lys Tyr Tyr Ala Asp Ser Val Lys
1               5                   10                  15

Gly

<210> SEQ ID NO 304
<211> LENGTH: 18
<212> TYPE: PRT
<213> ORGANISM: Artificial Sequence
<220> FEATURE:
<223> OTHER INFORMATION: clone GS004_Variable heavy chain CDR3

<400> SEQUENCE: 304

Tyr Arg Val Trp Ala His Ser Ala Ser Ser Tyr Ser Asn Ala Met
1               5                   10                  15

Asp Val

<210> SEQ ID NO 305
<211> LENGTH: 13
<212> TYPE: PRT
<213> ORGANISM: Artificial Sequence
<220> FEATURE:
<223> OTHER INFORMATION: clone GS004_Variable light chain CDR1

<400> SEQUENCE: 305

Ser Gly Ser Ser Ser Asn Ile Gly Asn Asn Asp Val Ser
1               5                   10

<210> SEQ ID NO 306
<211> LENGTH: 7
<212> TYPE: PRT
<213> ORGANISM: Artificial Sequence
<220> FEATURE:
<223> OTHER INFORMATION: clone GS004_Variable light chain CDR2

<400> SEQUENCE: 306

Ser Asp Ser Gln Arg Pro Ser
1               5

<210> SEQ ID NO 307
<211> LENGTH: 9
<212> TYPE: PRT
```

```
<213> ORGANISM: Artificial Sequence
<220> FEATURE:
<223> OTHER INFORMATION: clone GS004_Variable light chain CDR3

<400> SEQUENCE: 307

Gly Ser Trp Asp Asp Ser Leu Asn Gly
1               5

<210> SEQ ID NO 308
<211> LENGTH: 5
<212> TYPE: PRT
<213> ORGANISM: Artificial Sequence
<220> FEATURE:
<223> OTHER INFORMATION: clone GS005_Variable heavy chain CDR1

<400> SEQUENCE: 308

Asn Tyr Ala Met Ser
1               5

<210> SEQ ID NO 309
<211> LENGTH: 17
<212> TYPE: PRT
<213> ORGANISM: Artificial Sequence
<220> FEATURE:
<223> OTHER INFORMATION: clone GS005_Variable heavy chain CDR2

<400> SEQUENCE: 309

Val Ile Ser Pro Asp Ser Ser Ser Lys Tyr Tyr Ala Asp Ser Val Lys
1               5                   10                  15

Gly

<210> SEQ ID NO 310
<211> LENGTH: 18
<212> TYPE: PRT
<213> ORGANISM: Artificial Sequence
<220> FEATURE:
<223> OTHER INFORMATION: clone GS005_Variable heavy chain CDR3

<400> SEQUENCE: 310

Ala Ala Val Arg Arg Tyr Gly Pro Ser Pro Tyr Tyr Tyr Tyr Ala Met
1               5                   10                  15

Asp Val

<210> SEQ ID NO 311
<211> LENGTH: 13
<212> TYPE: PRT
<213> ORGANISM: Artificial Sequence
<220> FEATURE:
<223> OTHER INFORMATION: clone GS005_Variable light chain CDR1

<400> SEQUENCE: 311

Thr Gly Ser Ser Ser Asn Ile Gly Asn Asn Tyr Val Ser
1               5                   10

<210> SEQ ID NO 312
<211> LENGTH: 7
<212> TYPE: PRT
<213> ORGANISM: Artificial Sequence
<220> FEATURE:
<223> OTHER INFORMATION: clone GS005_Variable light chain CDR2

<400> SEQUENCE: 312

Ala Asp Ser His Arg Pro Ser
1               5
```

```
<210> SEQ ID NO 313
<211> LENGTH: 9
<212> TYPE: PRT
<213> ORGANISM: Artificial Sequence
<220> FEATURE:
<223> OTHER INFORMATION: clone GS005_Variable light chain CDR3

<400> SEQUENCE: 313

Ala Thr Trp Asp Tyr Ser Leu Ser Gly
1               5

<210> SEQ ID NO 314
<211> LENGTH: 17
<212> TYPE: PRT
<213> ORGANISM: Artificial Sequence
<220> FEATURE:
<223> OTHER INFORMATION: clone GS006_Variable heavy chain CDR2

<400> SEQUENCE: 314

Ala Ile Ser Pro Gly Gly Gly Ser Lys Tyr Tyr Ala Asp Ser Val Arg
1               5                   10                  15

Gly

<210> SEQ ID NO 315
<211> LENGTH: 18
<212> TYPE: PRT
<213> ORGANISM: Artificial Sequence
<220> FEATURE:
<223> OTHER INFORMATION: clone GS006_Variable heavy chain CDR3

<400> SEQUENCE: 315

Tyr Arg Val Gln Lys Ser Ala Lys Asn Val Tyr Ser Ser Asn Gly Met
1               5                   10                  15

Asp Val

<210> SEQ ID NO 316
<211> LENGTH: 13
<212> TYPE: PRT
<213> ORGANISM: Artificial Sequence
<220> FEATURE:
<223> OTHER INFORMATION: clone GS006_Variable light chain CDR1

<400> SEQUENCE: 316

Ser Gly Ser Ser Ser Asn Ile Gly Asn Asn Ala Val Asn
1               5                   10

<210> SEQ ID NO 317
<211> LENGTH: 7
<212> TYPE: PRT
<213> ORGANISM: Artificial Sequence
<220> FEATURE:
<223> OTHER INFORMATION: clone GS006_Variable light chain CDR2

<400> SEQUENCE: 317

Tyr Asp Ser Asn Arg Pro Ser
1               5

<210> SEQ ID NO 318
<211> LENGTH: 17
<212> TYPE: PRT
<213> ORGANISM: Artificial Sequence
<220> FEATURE:
<223> OTHER INFORMATION: clone GS007_Variable heavy chain CDR2

<400> SEQUENCE: 318

Val Ile Ser His Asp Gly Arg Ser Lys Tyr Tyr Ala Asp Ser Val Lys
```

Gly

<210> SEQ ID NO 319
<211> LENGTH: 18
<212> TYPE: PRT
<213> ORGANISM: Artificial Sequence
<220> FEATURE:
<223> OTHER INFORMATION: clone GS007_Variable heavy chain CDR3

<400> SEQUENCE: 319

Phe Arg Val Trp Lys Arg Thr Asn Ala His Ser Tyr Ala Asn Ala Met
1               5                   10                  15

Asp Val

<210> SEQ ID NO 320
<211> LENGTH: 13
<212> TYPE: PRT
<213> ORGANISM: Artificial Sequence
<220> FEATURE:
<223> OTHER INFORMATION: clone GS007_Variable light chain CDR1

<400> SEQUENCE: 320

Thr Gly Ser Ser Ser Asn Ile Gly Ser Asn Ser Val Ser
1               5                   10

<210> SEQ ID NO 321
<211> LENGTH: 7
<212> TYPE: PRT
<213> ORGANISM: Artificial Sequence
<220> FEATURE:
<223> OTHER INFORMATION: clone GS007_Variable light chain CDR2

<400> SEQUENCE: 321

Ala Asn Ser Asn Arg Pro Ser
1               5

<210> SEQ ID NO 322
<211> LENGTH: 9
<212> TYPE: PRT
<213> ORGANISM: Artificial Sequence
<220> FEATURE:
<223> OTHER INFORMATION: clone GS007_Variable light chain CDR3

<400> SEQUENCE: 322

Gly Thr Trp Asp Ala Ser Leu Ser Ala
1               5

<210> SEQ ID NO 323
<211> LENGTH: 17
<212> TYPE: PRT
<213> ORGANISM: Artificial Sequence
<220> FEATURE:
<223> OTHER INFORMATION: clone GS008_Variable heavy chain CDR2

<400> SEQUENCE: 323

Val Ile Ser Pro Asp Asn Gly Ser Thr Tyr Tyr Ala Asp Ser Val Lys
1               5                   10                  15

Gly

<210> SEQ ID NO 324
<211> LENGTH: 17
<212> TYPE: PRT
<213> ORGANISM: Artificial Sequence
<220> FEATURE:

```
<223> OTHER INFORMATION: clone GS008_Variable heavy chain CDR3

<400> SEQUENCE: 324

Ala Arg Val His Cys Arg Arg Asp Gln Cys Tyr Ser Tyr Gly Met Asp
1               5                   10                  15

Val

<210> SEQ ID NO 325
<211> LENGTH: 13
<212> TYPE: PRT
<213> ORGANISM: Artificial Sequence
<220> FEATURE:
<223> OTHER INFORMATION: clone GS008_Variable light chain CDR1

<400> SEQUENCE: 325

Thr Gly Ser Ser Ser Asn Ile Gly Ser Asn Asn Val Thr
1               5                   10

<210> SEQ ID NO 326
<211> LENGTH: 7
<212> TYPE: PRT
<213> ORGANISM: Artificial Sequence
<220> FEATURE:
<223> OTHER INFORMATION: clone GS008_Variable light chain CDR2

<400> SEQUENCE: 326

Ala Asn Ser Gln Arg Pro Ser
1               5

<210> SEQ ID NO 327
<211> LENGTH: 9
<212> TYPE: PRT
<213> ORGANISM: Artificial Sequence
<220> FEATURE:
<223> OTHER INFORMATION: clone GS008_Variable light chain CDR3

<400> SEQUENCE: 327

Gly Ala Trp Asp Ser Ser Leu Asn Gly
1               5

<210> SEQ ID NO 328
<211> LENGTH: 17
<212> TYPE: PRT
<213> ORGANISM: Artificial Sequence
<220> FEATURE:
<223> OTHER INFORMATION: clone GS009_Variable heavy chain CDR2

<400> SEQUENCE: 328

Val Ile Ser Pro Ser Gly Gly Asn Thr Tyr Tyr Ala Asp Ser Val Lys
1               5                   10                  15

Gly

<210> SEQ ID NO 329
<211> LENGTH: 18
<212> TYPE: PRT
<213> ORGANISM: Artificial Sequence
<220> FEATURE:
<223> OTHER INFORMATION: clone GS009_Variable heavy chain CDR3

<400> SEQUENCE: 329

Tyr Arg Val Lys Gln Met Leu Asn Gln Arg Ser Tyr Ser Asn Ala Met
1               5                   10                  15

Asp Val
```

```
<210> SEQ ID NO 330
<211> LENGTH: 7
<212> TYPE: PRT
<213> ORGANISM: Artificial Sequence
<220> FEATURE:
<223> OTHER INFORMATION: clone GS009_Variable light chain CDR2

<400> SEQUENCE: 330

Asp Asp Ser Gln Arg Pro Ser
1               5

<210> SEQ ID NO 331
<211> LENGTH: 17
<212> TYPE: PRT
<213> ORGANISM: Artificial Sequence
<220> FEATURE:
<223> OTHER INFORMATION: clone GS010_Variable heavy chain CDR2

<400> SEQUENCE: 331

Val Ile Ser Pro Ser Ser Gly Ser Ile Tyr Tyr Ala Asp Ser Val Lys
1               5                   10                  15

Gly

<210> SEQ ID NO 332
<211> LENGTH: 18
<212> TYPE: PRT
<213> ORGANISM: Artificial Sequence
<220> FEATURE:
<223> OTHER INFORMATION: clone GS010_Variable heavy chain CDR3

<400> SEQUENCE: 332

Tyr Arg Val Arg Gln Leu Lys His Thr Arg Ser Tyr Ala Asp Ala Met
1               5                   10                  15

Asp Val

<210> SEQ ID NO 333
<211> LENGTH: 13
<212> TYPE: PRT
<213> ORGANISM: Artificial Sequence
<220> FEATURE:
<223> OTHER INFORMATION: clone GS010_Variable light chain CDR1

<400> SEQUENCE: 333

Ser Gly Ser Ser Ser Asn Ile Gly Ser Asn Ala Val Ser
1               5                   10

<210> SEQ ID NO 334
<211> LENGTH: 7
<212> TYPE: PRT
<213> ORGANISM: Artificial Sequence
<220> FEATURE:
<223> OTHER INFORMATION: clone GS010_Variable light chain CDR2

<400> SEQUENCE: 334

Ala Asn Ser His Arg Pro Ser
1               5

<210> SEQ ID NO 335
<211> LENGTH: 9
<212> TYPE: PRT
<213> ORGANISM: Artificial Sequence
<220> FEATURE:
<223> OTHER INFORMATION: clone GS010_Variable light chain CDR3

<400> SEQUENCE: 335

Ala Ser Trp Asp Ser Ser Leu Ser Gly
```

```
<210> SEQ ID NO 336
<211> LENGTH: 17
<212> TYPE: PRT
<213> ORGANISM: Artificial Sequence
<220> FEATURE:
<223> OTHER INFORMATION: clone GS011_Variable heavy chain CDR2

<400> SEQUENCE: 336

Gly Ile Ser Pro Gly Gly Ser Ser Ile Tyr Tyr Ala Asp Ser Val Lys
1               5                   10                  15
Gly

<210> SEQ ID NO 337
<211> LENGTH: 18
<212> TYPE: PRT
<213> ORGANISM: Artificial Sequence
<220> FEATURE:
<223> OTHER INFORMATION: clone GS011_Variable heavy chain CDR3

<400> SEQUENCE: 337

Tyr Ala Val Tyr Phe Leu Arg Ser His Gly Ser Tyr Asp Tyr Gly Met
1               5                   10                  15
Asp Val

<210> SEQ ID NO 338
<211> LENGTH: 13
<212> TYPE: PRT
<213> ORGANISM: Artificial Sequence
<220> FEATURE:
<223> OTHER INFORMATION: clone GS011_Variable light chain CDR1

<400> SEQUENCE: 338

Thr Gly Ser Ser Ser Asn Ile Gly Ser Asn Asp Val Thr
1               5                   10

<210> SEQ ID NO 339
<211> LENGTH: 7
<212> TYPE: PRT
<213> ORGANISM: Artificial Sequence
<220> FEATURE:
<223> OTHER INFORMATION: clone GS011_Variable light chain CDR2

<400> SEQUENCE: 339

Ser Asn Asn Gln Arg Pro Ser
1               5

<210> SEQ ID NO 340
<211> LENGTH: 9
<212> TYPE: PRT
<213> ORGANISM: Artificial Sequence
<220> FEATURE:
<223> OTHER INFORMATION: clone GS011_Variable light chain CDR3

<400> SEQUENCE: 340

Gly Ala Trp Asp Tyr Ser Leu Asn Ala
1               5

<210> SEQ ID NO 341
<211> LENGTH: 17
<212> TYPE: PRT
<213> ORGANISM: Artificial Sequence
<220> FEATURE:
<223> OTHER INFORMATION: clone GS012_Variable heavy chain CDR2
```

<400> SEQUENCE: 341

Gly Ile Ser Pro Gly Ser Gly Ser Lys Tyr Tyr Ala Asp Ser Val Arg
1               5                   10                  15

Gly

<210> SEQ ID NO 342
<211> LENGTH: 7
<212> TYPE: PRT
<213> ORGANISM: Artificial Sequence
<220> FEATURE:
<223> OTHER INFORMATION: clone GS012_Variable heavy chain CDR3

<400> SEQUENCE: 342

Arg Ala Arg Arg Phe Asp Tyr
1               5

<210> SEQ ID NO 343
<211> LENGTH: 13
<212> TYPE: PRT
<213> ORGANISM: Artificial Sequence
<220> FEATURE:
<223> OTHER INFORMATION: clone GS012_Variable light chain CDR1

<400> SEQUENCE: 343

Thr Gly Ser Ser Ser Asn Ile Gly Asn Asn Ala Val Thr
1               5                   10

<210> SEQ ID NO 344
<211> LENGTH: 9
<212> TYPE: PRT
<213> ORGANISM: Artificial Sequence
<220> FEATURE:
<223> OTHER INFORMATION: clone GS012_Variable light chain CDR3

<400> SEQUENCE: 344

Gly Ser Trp Asp Ser Ser Leu Asn Gly
1               5

<210> SEQ ID NO 345
<211> LENGTH: 17
<212> TYPE: PRT
<213> ORGANISM: Artificial Sequence
<220> FEATURE:
<223> OTHER INFORMATION: clone GS013_Variable heavy chain CDR2

<400> SEQUENCE: 345

Ser Ile Ser Ser Gly Gly Gly Ser Thr Tyr Tyr Ala Asp Ser Val Lys
1               5                   10                  15

Gly

<210> SEQ ID NO 346
<211> LENGTH: 7
<212> TYPE: PRT
<213> ORGANISM: Artificial Sequence
<220> FEATURE:
<223> OTHER INFORMATION: clone GS013_Variable heavy chain CDR3

<400> SEQUENCE: 346

Lys Lys Ser Gln Phe Asp Tyr
1               5

<210> SEQ ID NO 347
<211> LENGTH: 13
<212> TYPE: PRT
<213> ORGANISM: Artificial Sequence

```
<220> FEATURE:
<223> OTHER INFORMATION: clone GS013_Variable light chain CDR1

<400> SEQUENCE: 347

Ser Gly Ser Ser Ser Asn Ile Gly Ser Asn Thr Val Asn
1               5                   10

<210> SEQ ID NO 348
<211> LENGTH: 9
<212> TYPE: PRT
<213> ORGANISM: Artificial Sequence
<220> FEATURE:
<223> OTHER INFORMATION: clone GS013_Variable light chain CDR3

<400> SEQUENCE: 348

Asp Thr Trp Asp Tyr Ser Leu Ser Gly
1               5

<210> SEQ ID NO 349
<211> LENGTH: 18
<212> TYPE: PRT
<213> ORGANISM: Artificial Sequence
<220> FEATURE:
<223> OTHER INFORMATION: clone GS014_Variable heavy chain CDR2

<400> SEQUENCE: 349

Val Ile Ser Pro Asn Ser Gly Ser Asn Thr Tyr Tyr Ala Asp Ser Val
1               5                   10                  15

Lys Gly

<210> SEQ ID NO 350
<211> LENGTH: 18
<212> TYPE: PRT
<213> ORGANISM: Artificial Sequence
<220> FEATURE:
<223> OTHER INFORMATION: clone GS014_Variable heavy chain CDR3

<400> SEQUENCE: 350

Pro Arg Ile Leu Arg Arg Arg Val Asp His Ser Tyr Ser Tyr Ala Met
1               5                   10                  15

Asp Val

<210> SEQ ID NO 351
<211> LENGTH: 7
<212> TYPE: PRT
<213> ORGANISM: Artificial Sequence
<220> FEATURE:
<223> OTHER INFORMATION: clone GS014_Variable light chain CDR2

<400> SEQUENCE: 351

Ser Asn Ser His Arg Pro Ser
1               5

<210> SEQ ID NO 352
<211> LENGTH: 9
<212> TYPE: PRT
<213> ORGANISM: Artificial Sequence
<220> FEATURE:
<223> OTHER INFORMATION: clone GS014_Variable light chain CDR3

<400> SEQUENCE: 352

Gly Thr Trp Asp Tyr Ser Leu Ser Gly
1               5

<210> SEQ ID NO 353
```

```
<211> LENGTH: 5
<212> TYPE: PRT
<213> ORGANISM: Artificial Sequence
<220> FEATURE:
<223> OTHER INFORMATION: clone GS015_Variable heavy chain CDR1

<400> SEQUENCE: 353

Asp Tyr Ser Met Ser
1               5

<210> SEQ ID NO 354
<211> LENGTH: 18
<212> TYPE: PRT
<213> ORGANISM: Artificial Sequence
<220> FEATURE:
<223> OTHER INFORMATION: clone GS015_Variable heavy chain CDR2

<400> SEQUENCE: 354

Ala Ile Ser Pro Asp Gly Gly Ser Lys Tyr Tyr Ala Asp Ser Val Lys
1               5                   10                  15

Gly Arg

<210> SEQ ID NO 355
<211> LENGTH: 18
<212> TYPE: PRT
<213> ORGANISM: Artificial Sequence
<220> FEATURE:
<223> OTHER INFORMATION: clone GS015_Variable heavy chain CDR3

<400> SEQUENCE: 355

Phe Arg Val Ile Lys Leu Arg Ala Gly Trp Tyr Ser Ala Asn Gly Met
1               5                   10                  15

Asp Val

<210> SEQ ID NO 356
<211> LENGTH: 13
<212> TYPE: PRT
<213> ORGANISM: Artificial Sequence
<220> FEATURE:
<223> OTHER INFORMATION: clone GS015_Variable light chain CDR1

<400> SEQUENCE: 356

Ser Gly Ser Ser Ser Asn Ile Gly Asn Asn Asp Val Ser
1               5                   10

<210> SEQ ID NO 357
<211> LENGTH: 7
<212> TYPE: PRT
<213> ORGANISM: Artificial Sequence
<220> FEATURE:
<223> OTHER INFORMATION: clone GS015_Variable light chain CDR2

<400> SEQUENCE: 357

Tyr Asn Ser Lys Arg Pro Ser
1               5

<210> SEQ ID NO 358
<211> LENGTH: 9
<212> TYPE: PRT
<213> ORGANISM: Artificial Sequence
<220> FEATURE:
<223> OTHER INFORMATION: clone GS015_Variable light chain CDR3

<400> SEQUENCE: 358

Gly Ala Trp Asp Asp Ser Leu Asn Gly
1               5
```

```
<210> SEQ ID NO 359
<211> LENGTH: 17
<212> TYPE: PRT
<213> ORGANISM: Artificial Sequence
<220> FEATURE:
<223> OTHER INFORMATION: clone GS016_Variable heavy chain CDR2

<400> SEQUENCE: 359

Gly Ile Tyr Ser Gly Asn Gly Asn Thr Tyr Tyr Ala Asp Ser Val Lys
1               5                   10                  15

Gly

<210> SEQ ID NO 360
<211> LENGTH: 18
<212> TYPE: PRT
<213> ORGANISM: Artificial Sequence
<220> FEATURE:
<223> OTHER INFORMATION: clone GS016_Variable heavy chain CDR3

<400> SEQUENCE: 360

Ala Leu Ser Ser Cys Pro Arg Gly Pro Cys Tyr Tyr Asp Asp Gly Met
1               5                   10                  15

Asp Val

<210> SEQ ID NO 361
<211> LENGTH: 13
<212> TYPE: PRT
<213> ORGANISM: Artificial Sequence
<220> FEATURE:
<223> OTHER INFORMATION: clone GS016_Variable light chain CDR1

<400> SEQUENCE: 361

Ser Gly Ser Ser Ser Asn Ile Gly Ser Asn Asp Val Thr
1               5                   10

<210> SEQ ID NO 362
<211> LENGTH: 7
<212> TYPE: PRT
<213> ORGANISM: Artificial Sequence
<220> FEATURE:
<223> OTHER INFORMATION: clone GS016_Variable light chain CDR2

<400> SEQUENCE: 362

Asp Asn Ser Lys Arg Pro Ser
1               5

<210> SEQ ID NO 363
<211> LENGTH: 4
<212> TYPE: PRT
<213> ORGANISM: Artificial Sequence
<220> FEATURE:
<223> OTHER INFORMATION: clone GS017_Variable heavy chain CDR1

<400> SEQUENCE: 363

Gly Tyr Ala Met
1

<210> SEQ ID NO 364
<211> LENGTH: 17
<212> TYPE: PRT
<213> ORGANISM: Artificial Sequence
<220> FEATURE:
<223> OTHER INFORMATION: clone GS017_Variable heavy chain CDR2

<400> SEQUENCE: 364
```

```
Gly Ile Ser Pro Gly Asp Gly Ser Thr Tyr Tyr Ala Asp Ser Val Lys
1               5                   10                  15

Gly

<210> SEQ ID NO 365
<211> LENGTH: 18
<212> TYPE: PRT
<213> ORGANISM: Artificial Sequence
<220> FEATURE:
<223> OTHER INFORMATION: clone GS017_Variable heavy chain CDR3

<400> SEQUENCE: 365

Val Ala Arg Met Cys Gln Gly Trp Arg Cys Ser Tyr Ala Asp Gly Met
1               5                   10                  15

Asp Val

<210> SEQ ID NO 366
<211> LENGTH: 13
<212> TYPE: PRT
<213> ORGANISM: Artificial Sequence
<220> FEATURE:
<223> OTHER INFORMATION: clone GS017_Variable light chain CDR1

<400> SEQUENCE: 366

Thr Gly Ser Ser Ser Asn Ile Gly Asn Asn Ser Val Tyr
1               5                   10

<210> SEQ ID NO 367
<211> LENGTH: 7
<212> TYPE: PRT
<213> ORGANISM: Artificial Sequence
<220> FEATURE:
<223> OTHER INFORMATION: clone GS017_Variable light chain CDR2

<400> SEQUENCE: 367

Ser Asp Ser His Arg Pro Ser
1               5

<210> SEQ ID NO 368
<211> LENGTH: 9
<212> TYPE: PRT
<213> ORGANISM: Artificial Sequence
<220> FEATURE:
<223> OTHER INFORMATION: clone GS017_Variable light chain CDR3

<400> SEQUENCE: 368

Gly Thr Trp Asp Ser Ser Leu Ser Gly
1               5

<210> SEQ ID NO 369
<211> LENGTH: 17
<212> TYPE: PRT
<213> ORGANISM: Artificial Sequence
<220> FEATURE:
<223> OTHER INFORMATION: clone GS018_Variable heavy chain CDR2

<400> SEQUENCE: 369

Val Ile Ser Pro Gly Ser Gly Ser Lys Tyr Tyr Ala Asp Ser Val Lys
1               5                   10                  15

Gly

<210> SEQ ID NO 370
<211> LENGTH: 18
<212> TYPE: PRT
```

<213> ORGANISM: Artificial Sequence
<220> FEATURE:
<223> OTHER INFORMATION: clone GS018_Variable heavy chain CDR3

<400> SEQUENCE: 370

His Arg Val Ile Lys Ile Asn Arg Gln Thr Tyr Tyr Asp Tyr Gly Met
1               5                   10                  15
Asp Val

<210> SEQ ID NO 371
<211> LENGTH: 13
<212> TYPE: PRT
<213> ORGANISM: Artificial Sequence
<220> FEATURE:
<223> OTHER INFORMATION: clone GS018_Variable light chain CDR1

<400> SEQUENCE: 371

Ser Gly Ser Ser Ser Asn Ile Gly Ser Asn Thr Val Ser
1               5                   10

<210> SEQ ID NO 372
<211> LENGTH: 7
<212> TYPE: PRT
<213> ORGANISM: Artificial Sequence
<220> FEATURE:
<223> OTHER INFORMATION: clone GS018_Variable light chain CDR2

<400> SEQUENCE: 372

Ser Asp Asn Asn Arg Pro Ser
1               5

<210> SEQ ID NO 373
<211> LENGTH: 9
<212> TYPE: PRT
<213> ORGANISM: Artificial Sequence
<220> FEATURE:
<223> OTHER INFORMATION: clone GS018_Variable light chain CDR3

<400> SEQUENCE: 373

Gly Ala Trp Asp Asp Ser Leu Ser Ala
1               5

<210> SEQ ID NO 374
<211> LENGTH: 5
<212> TYPE: PRT
<213> ORGANISM: Artificial Sequence
<220> FEATURE:
<223> OTHER INFORMATION: clone GN328_Variable heavy chain CDR1

<400> SEQUENCE: 374

Thr Ala Trp Met Asp
1               5

<210> SEQ ID NO 375
<211> LENGTH: 17
<212> TYPE: PRT
<213> ORGANISM: Artificial Sequence
<220> FEATURE:
<223> OTHER INFORMATION: clone GN328_Variable heavy chain CDR2

<400> SEQUENCE: 375

Asn Ile Asn Pro Asp Gly Ser Glu Lys His Tyr Val Asp Ser Val Lys
1               5                   10                  15
Gly

```
<210> SEQ ID NO 376
<211> LENGTH: 4
<212> TYPE: PRT
<213> ORGANISM: Artificial Sequence
<220> FEATURE:
<223> OTHER INFORMATION: clone GN328_Variable heavy chain CDR3

<400> SEQUENCE: 376

Ala Leu Asp Tyr
1

<210> SEQ ID NO 377
<211> LENGTH: 11
<212> TYPE: PRT
<213> ORGANISM: Artificial Sequence
<220> FEATURE:
<223> OTHER INFORMATION: clone GN328_Variable light chain CDR1

<400> SEQUENCE: 377

Arg Ala Ser Gln Asn Ile Asn Thr Trp Leu Ala
1               5                   10

<210> SEQ ID NO 378
<211> LENGTH: 7
<212> TYPE: PRT
<213> ORGANISM: Artificial Sequence
<220> FEATURE:
<223> OTHER INFORMATION: clone GN328_Variable light chain CDR2

<400> SEQUENCE: 378

Glu Ala Ser Ser Leu Glu Ser
1               5

<210> SEQ ID NO 379
<211> LENGTH: 7
<212> TYPE: PRT
<213> ORGANISM: Artificial Sequence
<220> FEATURE:
<223> OTHER INFORMATION: clone GN328_Variable light chain CDR3

<400> SEQUENCE: 379

Gln Gln Tyr Asn Thr Tyr Ser
1               5

<210> SEQ ID NO 380
<211> LENGTH: 7
<212> TYPE: PRT
<213> ORGANISM: Artificial Sequence
<220> FEATURE:
<223> OTHER INFORMATION: clone GN337_Variable heavy chain CDR1

<400> SEQUENCE: 380

Ser Gly Gly Tyr His Trp Asn
1               5

<210> SEQ ID NO 381
<211> LENGTH: 14
<212> TYPE: PRT
<213> ORGANISM: Artificial Sequence
<220> FEATURE:
<223> OTHER INFORMATION: clone GN337_Variable heavy chain CDR2

<400> SEQUENCE: 381

Tyr Ile Phe Asn Ser Gly Asn Thr Asp Tyr Asn Pro Ser Leu
1               5                   10

<210> SEQ ID NO 382
```

```
<211> LENGTH: 11
<212> TYPE: PRT
<213> ORGANISM: Artificial Sequence
<220> FEATURE:
<223> OTHER INFORMATION: clone GN337_Variable heavy chain CDR3

<400> SEQUENCE: 382

His Arg Ser Arg Leu Leu Arg Trp Phe Asp Tyr
1               5                   10

<210> SEQ ID NO 383
<211> LENGTH: 11
<212> TYPE: PRT
<213> ORGANISM: Artificial Sequence
<220> FEATURE:
<223> OTHER INFORMATION: clone GN337_Variable light chain CDR1

<400> SEQUENCE: 383

Gln Ala Ser Gln Asp Ile Arg Lys Tyr Leu Asn
1               5                   10

<210> SEQ ID NO 384
<211> LENGTH: 7
<212> TYPE: PRT
<213> ORGANISM: Artificial Sequence
<220> FEATURE:
<223> OTHER INFORMATION: clone GN337_Variable light chain CDR2

<400> SEQUENCE: 384

Asp Ala Ser Thr Leu Glu Thr
1               5

<210> SEQ ID NO 385
<211> LENGTH: 7
<212> TYPE: PRT
<213> ORGANISM: Artificial Sequence
<220> FEATURE:
<223> OTHER INFORMATION: clone GN337_Variable light chain CDR3

<400> SEQUENCE: 385

Gln Gln His Asp Phe Val Pro
1               5

<210> SEQ ID NO 386
<211> LENGTH: 5
<212> TYPE: PRT
<213> ORGANISM: Artificial Sequence
<220> FEATURE:
<223> OTHER INFORMATION: clone GN414_Variable heavy chain CDR1

<400> SEQUENCE: 386

Thr Tyr Gly Ile Thr
1               5

<210> SEQ ID NO 387
<211> LENGTH: 17
<212> TYPE: PRT
<213> ORGANISM: Artificial Sequence
<220> FEATURE:
<223> OTHER INFORMATION: clone GN414_Variable heavy chain CDR2

<400> SEQUENCE: 387

Arg Ile Thr Pro Asn Asn Gly Val Thr Asp Tyr Ala Gln Lys Phe Gln
1               5                   10                  15

Gly
```

```
<210> SEQ ID NO 388
<211> LENGTH: 12
<212> TYPE: PRT
<213> ORGANISM: Artificial Sequence
<220> FEATURE:
<223> OTHER INFORMATION: clone GN414_Variable heavy chain CDR3

<400> SEQUENCE: 388

Glu Ile Gly Ser Ser Ser Trp Lys Leu Leu Asp Pro
1               5                   10

<210> SEQ ID NO 389
<211> LENGTH: 13
<212> TYPE: PRT
<213> ORGANISM: Artificial Sequence
<220> FEATURE:
<223> OTHER INFORMATION: clone GN414_Variable light chain CDR1

<400> SEQUENCE: 389

Thr Gly Asn Ser Asn Asn Val Gly Tyr Glu Gly Ala Ala
1               5                   10

<210> SEQ ID NO 390
<211> LENGTH: 9
<212> TYPE: PRT
<213> ORGANISM: Artificial Sequence
<220> FEATURE:
<223> OTHER INFORMATION: clone GN414_Variable light chain CDR2

<400> SEQUENCE: 390

Ser Asp Arg Asn His Asn Arg Pro Ser
1               5

<210> SEQ ID NO 391
<211> LENGTH: 9
<212> TYPE: PRT
<213> ORGANISM: Artificial Sequence
<220> FEATURE:
<223> OTHER INFORMATION: clone GN414_Variable light chain CDR3

<400> SEQUENCE: 391

Ser Ala Trp Asp Ser Ser Leu Ser Glu
1               5

<210> SEQ ID NO 392
<211> LENGTH: 7
<212> TYPE: PRT
<213> ORGANISM: Artificial Sequence
<220> FEATURE:
<223> OTHER INFORMATION: clone GX184_Variable light chain CDR2

<400> SEQUENCE: 392

Arg Asn Asn Asn Arg Pro Ser
1               5

<210> SEQ ID NO 393
<211> LENGTH: 580
<212> TYPE: PRT
<213> ORGANISM: Artificial Sequence
<220> FEATURE:
<223> OTHER INFORMATION: Glypican 3 [Homo sapiens]

<400> SEQUENCE: 393

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Asp
            20                  25                  30
```

-continued

```
Ala Thr Cys His Gln Val Arg Ser Phe Phe Gln Arg Leu Gln Pro Gly
         35                  40                  45

Leu Lys Trp Val Pro Glu Thr Pro Val Pro Gly Ser Asp Leu Gln Val
 50                  55                  60

Cys Leu Pro Lys Gly Pro Thr Cys Cys Ser Arg Lys Met Glu Glu Lys
 65              70                  75                  80

Tyr Gln Leu Thr Ala Arg Leu Asn Met Glu Gln Leu Leu Gln Ser Ala
                 85                  90                  95

Ser Met Glu Leu Lys Phe Leu Ile Ile Gln Asn Ala Ala Val Phe Gln
                100                 105                 110

Glu Ala Phe Glu Ile Val Val Arg His Ala Lys Asn Tyr Thr Asn Ala
             115                 120                 125

Met Phe Lys Asn Asn Tyr Pro Ser Leu Thr Pro Gln Ala Phe Glu Phe
         130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Phe Ala Tyr Tyr Pro Glu Asp Leu Phe Ile
        355                 360                 365

Asp Lys Lys Val Leu Lys Val Ala His Val Glu His Glu Glu Thr Leu
370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
        435                 440                 445
```

-continued

```
Glu Leu Lys Met Lys Gly Pro Glu Pro Val Val Ser Gln Ile Ile Asp
    450                 455                 460
Lys Leu Lys His Ile Asn Gln Leu Leu Arg Thr Met Ser Met Pro Lys
465                 470                 475                 480
Gly Arg Val Leu Asp Lys Asn Leu Asp Glu Glu Gly Phe Glu Ser Gly
                485                 490                 495
Asp Cys Gly Asp Asp Glu Asp Glu Cys Ile Gly Gly Ser Gly Asp Gly
                500                 505                 510
Met Ile Lys Val Lys Asn Gln Leu Arg Phe Leu Ala Glu Leu Ala Tyr
            515                 520                 525
Asp Leu Asp Val Asp Asp Ala Pro Gly Asn Ser Gln Gln Ala Thr Pro
    530                 535                 540
Lys Asp Asn Glu Ile Ser Thr Phe His Asn Leu Gly Asn Val His Ser
545                 550                 555                 560
Pro Leu Lys Leu Leu Thr Ser Met Ala Ile Ser Val Val Cys Phe Phe
                565                 570                 575
Phe Leu Val His
            580
```